US011739348B2

(12) United States Patent
Peeples et al.

(10) Patent No.: US 11,739,348 B2
(45) Date of Patent: Aug. 29, 2023

(54) RECOMBINANT VECTORS ENCODING ZIKA VIRUS PROTEIN SUBUNITS

(71) Applicants: Research Institute at Nationwide Children's Hospital, Columbus, OH (US); Ohio State Innovation Foundation, Columbus, OH (US)

(72) Inventors: Mark Peeples, Bexley, OH (US); Jianrong Li, Dublin, OH (US); Prosper N. Boyaka, Columbus, OH (US); Anzhong Li, Columbus, OH (US); Mijia Lu, Columbus, OH (US); Yuanmei Ma, Pittsburgh, PA (US)

(73) Assignees: The Research Institute at Nationwide Children's Hospital, Columbus, OH (US); Ohio State Innovation Foundation, Columbus, OH (US)

( * ) Notice: Subject to any disclaimer, the term of this patent is extended or adjusted under 35 U.S.C. 154(b) by 217 days.

(21) Appl. No.: 16/762,836

(22) PCT Filed: Nov. 9, 2018

(86) PCT No.: PCT/US2018/060137
§ 371 (c)(1),
(2) Date: May 8, 2020

(87) PCT Pub. No.: WO2019/094801
PCT Pub. Date: May 16, 2019

(65) Prior Publication Data
US 2021/0171979 A1 Jun. 10, 2021

Related U.S. Application Data

(60) Provisional application No. 62/584,629, filed on Nov. 10, 2017.

(51) Int. Cl.
C12N 15/86 (2006.01)
A61K 39/12 (2006.01)
A61K 39/00 (2006.01)

(52) U.S. Cl.
CPC .............. C12N 15/86 (2013.01); A61K 39/12 (2013.01); A61K 2039/575 (2013.01); C12N 2760/20243 (2013.01); C12N 2760/20262 (2013.01); C12N 2770/24122 (2013.01); C12N 2770/24134 (2013.01); C12N 2770/24171 (2013.01)

(58) Field of Classification Search
None
See application file for complete search history.

(56) References Cited

U.S. PATENT DOCUMENTS

2017/0014502 A1* 1/2017 Sumathy ............... A61K 39/12
2017/0298119 A1* 10/2017 Wollacott ............... A61P 31/14

FOREIGN PATENT DOCUMENTS

| WO | WO 2007/044483 A2 * | 4/2017 |
|----|----|----|
| WO | WO2017132210 A1 | 8/2017 |
| WO | WO2017136419 A1 | 8/2017 |
| WO | WO2017140905 A1 | 8/2017 |
| WO | WO2017156511 A1 | 9/2017 |
| WO | WO2017184696 A1 | 10/2017 |

OTHER PUBLICATIONS

Whelan et al., PNAS USA, 1995, 92:8388-8392. (Year: 1995).*
Li et al., "A Zika virus vaccine expressing premembrane-envelope-Ns1 polyprotein," Nat. Commun., Aug. 3, 2018, vol. 9, No. 3067, pp. 1-17.
Brault et al., "A Zika Vaccine Targeting NS1 Protein Protects Immunocompetent Adult Mice in a Lethal Challenge Model," Sci. Rep., Nov. 7, 2017, vol. 7, No. 14769, pp. 1-11.
International Search Report and Written Opinion for PCT/US2018/060137, dated Jan. 28, 2019.

* cited by examiner

Primary Examiner — Stacy B Chen
(74) Attorney, Agent, or Firm — Banner & Witcoff, Ltd

(57) ABSTRACT

Embodiments disclosed herein provide compositions, methods, and uses for recombinant vectors encoding Zika virus (ZIKV) protein subunits, and immunogenic compositions thereof. Certain embodiments provide recombinant vectors encoding ZIKV nonstructural protein 1 (NS 1), and optionally, ZIKV envelope (E) protein and premembrane (prM) protein. Other embodiments provide expression cassettes comprising a promoter operably linked to a polynucleotide that encodes the ZIKV NS 1 protein, and optionally ZIKV E and prM proteins. In some embodiments, the disclosed expression cassettes can be incorporated into a vector to produce a recombinant vector. Also provided are immunogenic compositions comprising one or more recombinant vectors described herein, and methods for inducing an immune response against ZIKV in a subject comprising administering to the subject an immunologically effective dose of an immunogenic composition of the present disclosure.

19 Claims, 25 Drawing Sheets
Specification includes a Sequence Listing.

FIG. 9B — IFN-γ+CD4+, TNF-α+CD4+

FIG. 9C — IL-4+CD4+, IL-5+CD4+, IL-10+CD4+

Unst: Unstimulated
G1: DMEM
G2: rVSV-G1670A
G3: rVSV-G1670A-E
G4: rVSV-G1670A-prM-E
G5: rVSV-G1670A-prM-E-NS1

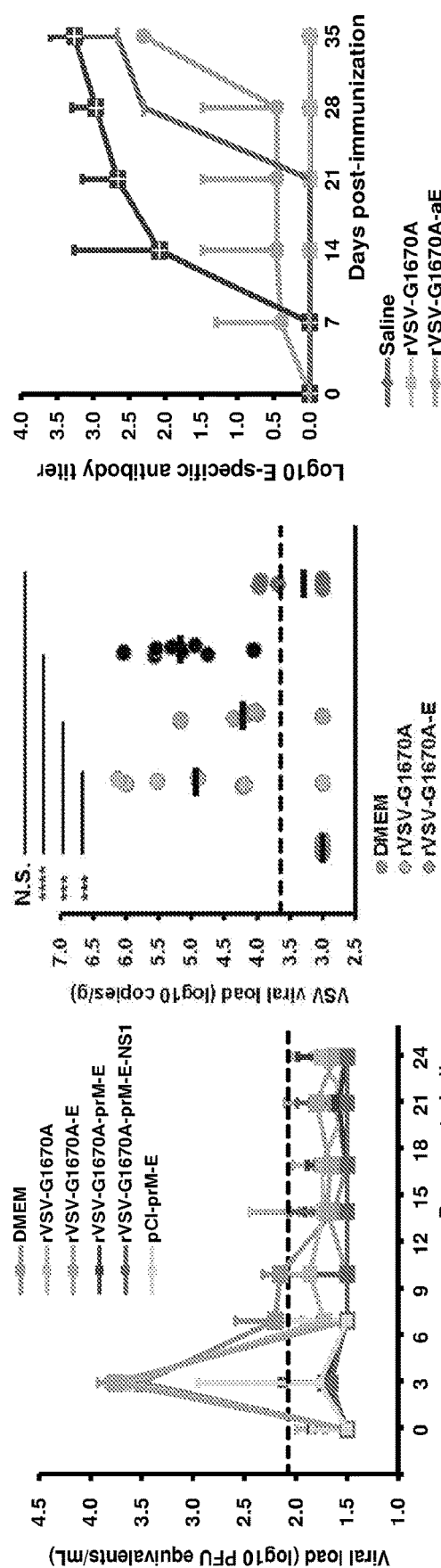
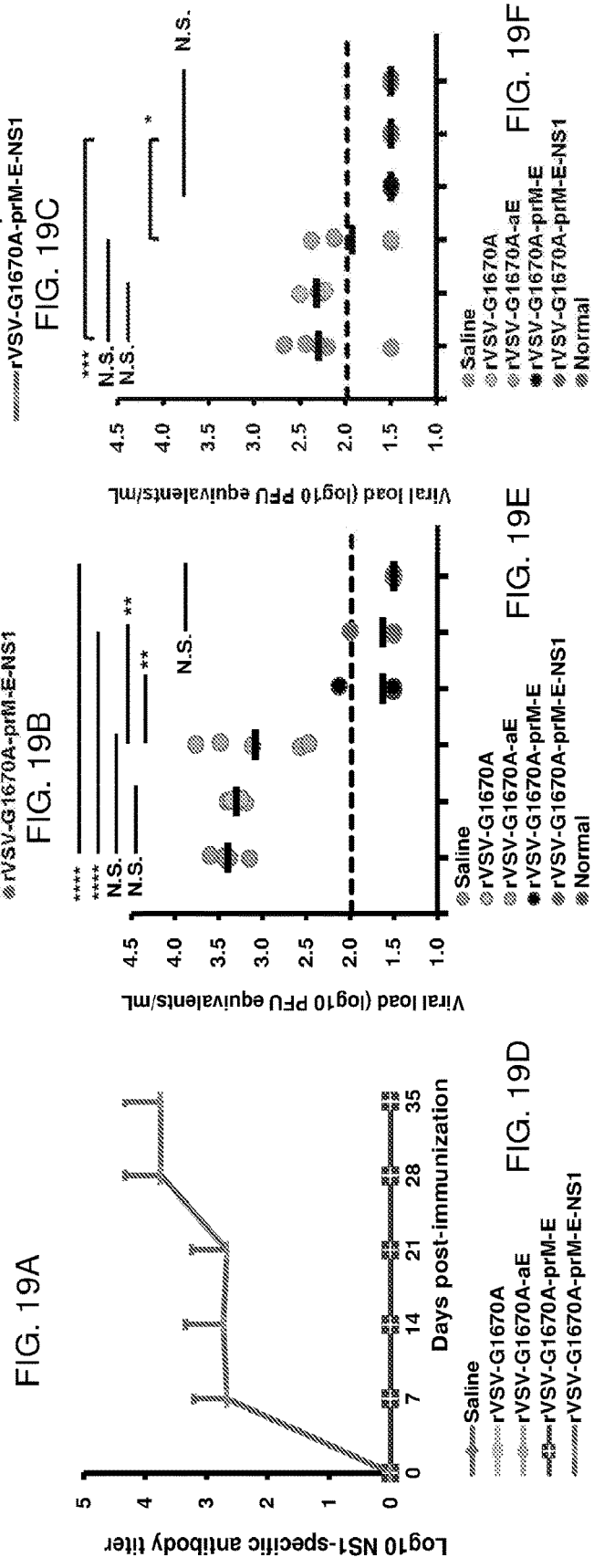
FIG. 19A
FIG. 19B
FIG. 19C
FIG. 19D
FIG. 19E
FIG. 19F

SEQUENCE LISTING

```
<160> NUMBER OF SEQ ID NOS: 25

<210> SEQ ID NO 1
<211> LENGTH: 10807
<212> TYPE: DNA
<213> ORGANISM: Zika virus

<400> SEQUENCE: 1
agttgttgat ctgtgtgaat cagactgcga cagttcgagt ttgaagcgaa agctagcaac      60
agtatcaaca ggttttattt tggatttgga aacgagagtt tctggtcatg aaaaacccaa     120
agaagaaatc cggaggattc cggattgtca atatgctaaa acgcggagta gcccgtgtga     180
gcccctttgg gggcttgaag aggctgccag ccggacttct gctgggtcat gggcccatca     240
ggatggtctt ggcgattcta gccttttga gattcacggc aatcaagcca tcactgggtc     300
```

```
tcatcaatag atgggttca gtggggaaaa aagaggctat ggaaataata aagaagttta      360
agaaagatct ggctgccatg ctgagaataa tcaatgctag gaaggagaag aagagacgag      420
gcacagatac tagtgtcgga attgttggcc tcctgctgac cacagccatg gcagtggagg      480
tcactagacg tgggaatgca tactatatgt acttggacag aagcgatgct ggggaggcca      540
tatcttttcc aaccacaatg gggatgaata agtgttatat acagatcatg gatcttggac      600
acatgtgtga tgccaccatg agctatgaat gccctatgct ggatgagggg gtagaaccag      660
atgacgtcga ttgttggtgc aacacgacgt caacttgggt tgtgtacgga acctgccacc      720
acaaaaaagg tgaagcacgg agatctagaa gagctgtgac gctcccctcc cattccacta      780
ggaagctgca aacgcggtcg cagacctggt tggaatcaag agaatacaca aagcacctga      840
ttagagtcga aaattggata ttcaggaacc ctggcttcgc gttagcagca gctgccatcg      900
cttggctttt gggaagctca acgagccaaa aagtcatata cttggtcatg atactgctga      960
ttgccccggc atacagcatc aggtgcatag gagtcagcaa tagggacttt gtggaaggta     1020
tgtcaggtgg gacttgggtt gatgttgtct tggaacatgg aggttgtgtt accgtaatgg     1080
cacaggacaa accgactgtc gacatagagc tggttacaac aacagtcagc aacatggcgg     1140
aggtaagatc ctactgctat gaggcatcaa tatcggacat ggcttcggac agccgctgcc     1200
caacacaagg tgaagcctac cttgacaagc aatcagacac tcaatatgtc tgcaaaagaa     1260
cgttagtgga cagaggctgg ggaaatggat gtggactttt tggcaagggg agcctggtga     1320
catgcgctaa gtttgcttgc tctaagaaaa tgaccgggaa gagcatccag ccagagaatc     1380
tggagtaccg gataatgctg tcagttcatg gctcccagca cagtgggatg atcgttaatg     1440
atacaggaca tgaaactgat gagaatagag cgaaggttga gataacgccc aattccacca     1500
gagccgaagc caccctgggg ggttttggaa gcctaggact tgattgtgaa ccgaggacag     1560
gccttgactt ttcagatttg tattacttga ctatgaataa caagcactgg ttggttcaca     1620
aggagtggtt ccacgacatt ccattacctt ggcatgctgg ggcagacacc ggaactccac     1680
actggaacaa caaagaagca ctggtagagt tcaaggacgc acatgccaaa aggcagactg     1740
tcgtggttct agggagtcaa gaaggagcag ttcacacggc ccttgctgga gctctggagg     1800
ctgagatgga tggtgcaaag ggaaggctgt cctctggcca cttgaaatgt cgcctgaaaa     1860
tggataaact tagattgaag ggcgtgtcat actccttgtg taccgcagcg ttcacattca     1920
ctaagatccc ggctgaaaca ctgcacggga cagtcacagt ggaggtacag tacgcaggga     1980
cagatggacc ttgcaaggtt ccagctcaga tggcggtgga catgcaaact ctgacccag      2040 ttgggaggtt gataaccgct aaccctgtaa tcactgaaag cactgagaac tccaagatga     2100
tgctggaact ggatccacca tttgggact cttacattgt cataggagtc ggggaaaaga     2160 agatcacccca ccactggcac aggagtggca gcaccattgg aaaagcattt gaagccactg     2220
tgagaggtgc caagagaatg gcagtcttgg gagacacagc ctgggactt ggatcagttg     2280 ggggtgctct caactcactg ggcaagggca tccatcaaat ttttggagca gctttcaaat     2340 cattgttgg aggaatgtcc tggttctcac aaattctcat ggaacgttg ctggtgtggt     2400 tgggtctgaa tacaaagaat ggatctattt cccttatgtg cttggcctta ggggagtgt     2460 tgatcttctt atccacagcc gtctctgctg atgtgggtg ctcggtggac ttctcaaaga     2520
aggaaacgag atgcggtaca ggggtgttcg tctataacga cgttgaagct tgagggaca     2580 ggtacaagta ccatcctgac tcccctcgta gattggcagc agcagtcaag caagcctggg     2640
aagatgggat ctgtgggatc tcctctgttt caagaatgga aaacatcatg tggagatcag     2700
```

```
tagaagggga gctcaacgca atcctggaag agaatggagt tcaactgacg gtcgttgtgg    2760
gatctgtaaa aaaccccatg tggagaggtc cacagagatt gcccgtgcct gtgaacgagc    2820
tgccccatgg ctggaaggct tgggggaaat cgtacttcgt cagggcagca aagacaaata    2880
acagctttgt cgtggatggt gacacactga aggaatgccc actcaaacat agagcatgga    2940
acagctttct tgtggaggat catgggttcg gggtatttca cactagtgtc tggctcaagg    3000
ttagagaaga ttattcatta gagtgtgatc cagccgtcat ggaacagcc  gctaagggaa    3060 aggaggctgt gcacagtgat ctaggctact ggattgagag tgagaagaac gacacatgga    3120
ggctgaagag ggcccacctg atcgagatga aacatgtga atggccaaag tcccacacat    3180
tgtggacaga tggaatagaa gaaagtgatc tgatcatacc caagtcttta gctgggccac    3240
tcagccatca caacaccaga gagggctaca ggacccaaat gaaagggcca tggcatagtg    3300
aagagcttga aattcggttt gaggaatgcc caggcactaa ggtccacgtg gaggaaacat    3360
gtggaacaag aggaccatct ctgagatcaa ccactgcaag cggaagggtg atcgaggaat    3420
ggtgctgcag ggagtgcaca atgcccccac tgtcgttccg ggctaaagat ggttgttggt    3480
atggaatgga gataaggccc aggaaagaac cagaaagtaa cttagtaagg tcaatggtga    3540
ctgcaggatc aactgatcac atggatcact tctcccttgg agtgcttgtg attctgctca    3600
tggtacagga agggctaaag aagagaatga ccacaaagat catcataagc acatcaatgg    3660
cagtgctggt agctatgatc ctgggaggat tttcaatgag tgacctggct aagcttgcaa    3720
ttttgatggg tgccaccttc gcggaaatga acactggagg agatgttgct catctggcgc    3780
tgatagcggc attcaaagtc agacctgcgt tgctggtatc tttcattttc agagctaatt    3840 ggacacccg tgagagcatg ctgctggcct tggcctcgtg tcttctgcaa actgcgatct    3900
ccgccttgga aggcgacctg atggttccca tcaatggttt tgctttggcc tggttggcaa    3960
tacgagcgat ggttgttcca cgcactgaca acatcacctt ggcaatcctg ctgctctga    4020 caccactggc ccggggcaca ctgcttgtgg cgtggagagc aggccttgct acttgcgggg    4080
ggttcatgct cctttctctg aaggggaaag gcagtgtgaa gaagaactta ccatttgtca    4140
tggccctggg actaaccgct gtgaggctgg tcgaccccat caacgtggtg ggactgctgt    4200
tgctcacaag gagtgggaag cggagctggc cccctagtga agtactcaca gctgttggcc    4260
tgatatgcgc attggctgga gggttcgcca aggcggatat agagatggct gggcccatgg    4320
ccgcggtcgg tctgctaatt gtcagttacg tggtctcagg aaagagtgtg gacatgtaca    4380
ttgaaagagc aggtgacatc acatgggaaa agatgcggaa gtcactggac aacagtcccc    4440
ggctcgatgt ggcactagat gagagtggtg atttctccct agtggaggat gatggtcccc    4500
ccatgagaga gatcatactc aaagtggtcc tgatggccat ctgtggcatg aacccaatag    4560
ccataccctt tgcagctgga gcgtggtacg tgtatgtgaa gactggaaaa aggagtggtg    4620
ctctatggga tgtgcctgct cccaaggaag taaaaaaggg ggagaccaca gatgagtgt    4680 acagagtaat gactcgtaga ctgctaggtt caacacaagt tggagtggga gtcatgcaag    4740
agggggtctt ccacactatg tggcacgtca caaaaggatc cgcgctgaga agcggtgaag    4800
ggagacttga tccatactgg ggagatgtca agcaggatct ggtgtcatac tgtggtccat    4860
ggaagctaga tgccgcctgg gacgggcaca gcgaggtgca gctcttggcc gtgccccccg    4920
gagagagagc gaggaacatc cagactctgc ccggaatatt taagacaaag gatgggdaca    4980
ttggagcagt tgcgctggac tacccagcag gaacttcagg atctccaatc ctagataagt    5040
```

```
gtgggagagt gataggactc tatggtaatg gggtcgtgat caaaaatggg agttacgtta    5100
gtgccatcac ccaagggagg agggaggaag agactcctgt tgagtgcttc gagccttcga    5160
tgctgaagaa gaagcagcta actgtcttag acttgcatcc tggagctggg aaaaccagga    5220
gagttcttcc tgaaatagtc cgtgaagcca taaaaacaag actccgcact gtgatcttag    5280
ctccaaccag ggttgtcgct gctgaaatgg aggaagccct tagagggctt ccagtgcgtt    5340
atatgacaac agcagtcaat gtcacccatt ctgggacaga aatcgttgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac tgccacgcca ccaggaaccc    5580
gtgacgcatt cccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaatggc aatgagatcg cagcttgtct gacaaaggct ggaaaacggg    5760
tcatacagct cagcagaaag acttttgaga cagagttcca gaaaacaaaa catcaagagt    5820
gggacttcgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag agggggcgc ataggcagga    6000 accccaacaa acctggagat gagtatctgt atggaggtgg gtgcgcagag actgatgaag    6060
accatgcaca ctggcttgaa gcaagaatgc ttcttgacaa catttacctc caagatggcc    6120
tcatagcctc gctctatcga cctgaggccg acaaagtagc agctattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300
ttgatggcac gaccaacaac accataatgg aagacagtgt gccggcagag gtgtggacca    6360
gatacggaga gaaaagagtg ctcaaaccga ggtggatgga cgccagagtt tgttcagatc    6420
atgcggccct gaagtcattc aaagagtttg ccgctgggaa aagaggagcg cctttggag    6480 tgatggaagc cctgggaaca ctgccaggac atatgacaga gagattccag gaggccattg    6540
acaacctcgc tgtgctcatg cgggcagaga ctggaagcag gccctacaaa gccgcggcgg    6600
cccaattacc ggagacccta gagactatca tgcttttggg gttgctggga acagtctcgc    6660
tgggaatctt tttcgtcttg atgcggaaca agggcatagg gaagatgggc tttggaatgg    6720
tgactcttgg ggccagcgca tggcttatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagtg ggtcttctgg    6900
gcttgattac cgccaatgaa ctcggatggt tggagagaac aaagagtgac ctaagccatc    6960
taatgggaag gagagaggag ggggcaacta taggattctc aatggacatt gacctgcggc    7020
cagcctcagc ttgggctatc tatgctgctc tgacaacttt cattacccca gccgtccaac    7080
atgcagtgac cacttcatac aacaactact ccttaatggc gatggccacg caagctggag    7140
tgttgttcgg tatgggtaaa gggatgccat tctatgcatg gactttggc gtcccgctgc    7200 taatgatagg ttgctactca caattaacac ccctgacccc aatagtggcc atcattttgc    7260
tcgtggcgca ctcatgtac ttgatcccag ggctgcaggc agcagctgcg cgtgctgccc    7320
agaagagaac ggcagctggc atcatgaaga acctgttgt ggatggaata gtggtgactg    7380
acattgacac aatgacaatt gaccccccaag tggagaaaaa gatgggacag gtgctactca    7440
```

```
tagcagtagc tgtctccagc gccatactgt cgcggaccgc ctgggggtgg ggtgaggctg    7500
gggccctgat cacagctgca acttccactt tgtgggaggg ctctccgaac aagtactgga    7560
actcctccac agccacctca ctgtgtaaca tttttagggg aagctacttg gctggagctt    7620
ctctaatcta cacagtaaca agaaacgctg gcttggtcaa gagacgtggg ggtggaacgg    7680
gagagaccct gggagagaaa tggaaggccc gcctgaacca gatgtcggcc ctggagttct    7740
actcctacaa aaagtcaggc atcaccgagg tgtgcagaga agaggcccgc cgcgccctca    7800
aggacggtgt ggcaacggga ggccacgctg tgtcccgagg aagtgcaaag ctgagatggt    7860
tggtggagag gggatacctg cagccctatg gaaaggtcat tgatcttgga tgtggcagag    7920
ggggctggag ttactatgcc gccaccatcc gcaaagttca agaagtgaaa ggatacacaa    7980
aaggaggccc tggtcatgaa gaacccatgt tggtgcaaag ctatgggtgg aacatagtcc    8040
gtcttaagag tggggtggac gtctttcata tggcggctga gccgtgtgac acgttgctgt    8100
gtgatatagg tgagtcatca tctagtcctg aagtggaaga agcacggacg ctcagagtcc    8160
tctccatggt gggggattgg cttgaaaaaa gaccaggagc ctttttgtata aaagtgttgt    8220 gcccatacac cagcactatg atggaaaccc tggagcgact gcagcgtagg tatgggggag    8280
gactggtcag agtgccactc tcccgcaact ctacacatga gatgtactgg gtctctggag    8340
cgaaaagcaa caccataaaa agtgtgtcca ccacgagcca gctccttttg gggcgcatgg    8400
acgggcccag gaggccagtg aaatatgaag aggatgtgaa tctcggctct ggcacgcggg    8460
ctgtggtaag ctgcgctgaa gctcccaaca tgaagatcat tggtaaccgc attgagagga    8520
tccgcagtga gcacgcggaa acgtggttct ttgacgagaa ccacccatat aggacatggg    8580
cttaccatgg aagctacgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaagtggac actagggtgc    8760 cagaccccca agaaggcact cgtcaggtta tgagcatggt ctcttcctgg ttgtggaaag    8820
agttaggcaa acacaaacgg ccacgagtct gtaccaaaga agagttcatc aacaaggttc    8880
gtagcaacgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtacat gtggctaggg gctagatttc    9120
tagagttcga agcccttgga ttcttgaacg aggatcactg gatggggaga gagaattcag    9180
gaggtggtgt tgaagggcta ggattacaaa gactcggata tgtcttagaa gagatgagtc    9240
gcataccagg aggaaggatg tatgcagatg atactgctgg ctgggacacc cgcatcagca    9300
ggtttgatct ggagaatgaa gctctaatca ccaaccaaat ggagaaaggg cacagggcct    9360
tggcattggc cataatcaag tacacatacc aaaacaaagt ggtaaggtc cttagaccag    9420 ctgaaaaagg gaagacagtt atggacatta tttcaagaca agaccaaagg gggagcggac    9480
aagttgtcac ttacgctctt aatacattta ccaacctagt ggtgcagctc attcggaata    9540
tggaggctga ggaagttcta gagatgcaag acttgtggct gctgcggagg tcagagaaag    9600
tgaccaactg gttgcagagc aatggatggg ataggctcaa acgaatggca gtcagtggag    9660
atgattgcgt tgtgaaacca attgatgata ggttgcaca tgctctcagg ttcttgaatg    9720
atatgggaaa agttaggaag gacacacaag agtggaagcc ctcaactgga tgggacaact    9780
```

-continued gggaagaagt tccgttttgc tcccaccact tcaacaagct ccatctcaag gacgggaggt 9840
ccattgtggt tccctgccgc caccaagatg aactgattgg ccgagctcgc gtctcaccgg 9900
gggcgggatg gagcatccgg gagactgctt gcctagcaaa atcatatgcg caaatgtggc 9960
agctccttta tttccacaga agggacctcc gactgatggc caatgccatt tgttcatctg 10020
tgccagttga ctgggttcca actgggagaa ctacctggtc aatccatgga aagggagaat 10080
ggatgaccac tgaagacatg cttgtggtgt ggaacagagt gtggattgag gagaacgacc 10140
acatggaaga caagacccca gttacgaaat ggacagacat tccctatttg ggaaaaaggg 10200
aagacttgtg gtgtgggtct ctcatagggc acagaccgcg caccacctgg gctgagaaca 10260
ttaaaaacac agtcaacatg atgcgtagga tcataggtga tgaagaaaag tacgtggact 10320
acctatccac ccaagttcgc tacttgggcg aagaagggtc cacacctgga gtgctataag 10380
caccaatctt agtgttgtca ggcctgctag tcagccacag cttggggaaa gctgtgcagc 10440
ctgtgacccc cccaggagaa gctgggaaac caagcccata gtcaggccga gaacgccatg 10500
gcacggaaga agccatgctg cctgtgagcc cctcagagga cactgagtca aaaaacccca 10560
cgcgcttgga ggcgcaggat gggaaaagaa ggtggcgacc ttccccaccc tttaatctgg 10620
ggcctgaact ggagatcagc tgtggatctc cagaagaggg actagtggtt agaggagacc 10680
ccccggaaaa cgcaaaacag catattgacg ctgggaaaga ccagagactc catgagtttc 10740
caccacgctg gccgccaggc acagatcgcc gaatagcggc ggccggtgtg gggaaatcca 10800
tgggtct 10807

<210> SEQ ID NO 2
<211> LENGTH: 3423
<212> TYPE: PRT
<213> ORGANISM: Zika virus

<400> SEQUENCE: 2

Met Lys Asn Pro Lys Lys Lys Ser Gly Gly Phe Arg Ile Val Asn Met
1 5 10 15

Leu Lys Arg Gly Val Ala Arg Val Ser Pro Phe Gly Gly Leu Lys Arg
20 25 30

Leu Pro Ala Gly Leu Leu Leu Gly His Gly Pro Ile Arg Met Val Leu
35 40 45

Ala Ile Leu Ala Phe Leu Arg Phe Thr Ala Ile Lys Pro Ser Leu Gly
50 55 60

Leu Ile Asn Arg Trp Gly Ser Val Gly Lys Lys Glu Ala Met Glu Ile
65 70 75 80

Ile Lys Lys Phe Lys Lys Asp Leu Ala Ala Met Leu Arg Ile Ile Asn
85 90 95

Ala Arg Lys Glu Lys Lys Arg Arg Gly Thr Asp Thr Ser Val Gly Ile
100 105 110

Val Gly Leu Leu Leu Thr Thr Ala Met Ala Val Glu Val Thr Arg Arg
115 120 125

Gly Asn Ala Tyr Tyr Met Tyr Leu Asp Arg Ser Asp Ala Gly Glu Ala
130 135 140

Ile Ser Phe Pro Thr Thr Met Gly Met Asn Lys Cys Tyr Ile Gln Ile
145 150 155 160

Met Asp Leu Gly His Met Cys Asp Ala Thr Met Ser Tyr Glu Cys Pro
165 170 175

Met Leu Asp Glu Gly Val Glu Pro Asp Asp Val Asp Cys Trp Cys Asn
180 185 190

```
Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ile Ala Trp Leu Leu Gly Ser Ser Thr
                260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
        290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
                340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
        370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
                500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
        530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605
```

```
Ala Glu Thr Leu His Gly Thr Val Thr Val Glu Val Gln Tyr Ala Gly
610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
            645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
            675                 680                 685

His Trp His Arg Ser Gly Ser Thr Ile Gly Lys Ala Phe Glu Ala Thr
690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Val Trp Leu Gly Leu Asn
    755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Ala Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
    1010                1015                1020

Thr Leu Trp Thr Asp Gly Ile Glu Glu Ser Asp Leu Ile Ile Pro
```

```
           1025                1030                1035
Lys Ser Leu Ala Gly Pro Leu Ser His His Asn Thr Arg Glu Gly
       1040                1045                1050

Tyr Arg Thr Gln Met Lys Gly Pro Trp His Ser Glu Glu Leu Glu
       1055                1060                1065

Ile Arg Phe Glu Glu Cys Pro Gly Thr Lys Val His Val Glu Glu
       1070                1075                1080

Thr Cys Gly Thr Arg Gly Pro Ser Leu Arg Ser Thr Thr Ala Ser
       1085                1090                1095

Gly Arg Val Ile Glu Glu Trp Cys Cys Arg Glu Cys Thr Met Pro
       1100                1105                1110

Pro Leu Ser Phe Arg Ala Lys Asp Gly Cys Trp Tyr Gly Met Glu
       1115                1120                1125

Ile Arg Pro Arg Lys Glu Pro Glu Ser Asn Leu Val Arg Ser Met
       1130                1135                1140

Val Thr Ala Gly Ser Thr Asp His Met Asp His Phe Ser Leu Gly
       1145                1150                1155

Val Leu Val Ile Leu Leu Met Val Gln Glu Gly Leu Lys Lys Arg
       1160                1165                1170

Met Thr Thr Lys Ile Ile Ile Ser Thr Ser Met Ala Val Leu Val
       1175                1180                1185

Ala Met Ile Leu Gly Gly Phe Ser Met Ser Asp Leu Ala Lys Leu
       1190                1195                1200

Ala Ile Leu Met Gly Ala Thr Phe Ala Glu Met Asn Thr Gly Gly
       1205                1210                1215

Asp Val Ala His Leu Ala Leu Ile Ala Ala Phe Lys Val Arg Pro
       1220                1225                1230

Ala Leu Leu Val Ser Phe Ile Phe Arg Ala Asn Trp Thr Pro Arg
       1235                1240                1245

Glu Ser Met Leu Leu Ala Leu Ala Ser Cys Leu Leu Gln Thr Ala
       1250                1255                1260

Ile Ser Ala Leu Glu Gly Asp Leu Met Val Pro Ile Asn Gly Phe
       1265                1270                1275

Ala Leu Ala Trp Leu Ala Ile Arg Ala Met Val Val Pro Arg Thr
       1280                1285                1290

Asp Asn Ile Thr Leu Ala Ile Leu Ala Ala Leu Thr Pro Leu Ala
       1295                1300                1305

Arg Gly Thr Leu Leu Val Ala Trp Arg Ala Gly Leu Ala Thr Cys
       1310                1315                1320

Gly Gly Phe Met Leu Leu Ser Leu Lys Gly Lys Gly Ser Val Lys
       1325                1330                1335

Lys Asn Leu Pro Phe Val Met Ala Leu Gly Leu Thr Ala Val Arg
       1340                1345                1350

Leu Val Asp Pro Ile Asn Val Val Gly Leu Leu Leu Leu Thr Arg
       1355                1360                1365

Ser Gly Lys Arg Ser Trp Pro Pro Ser Glu Val Leu Thr Ala Val
       1370                1375                1380

Gly Leu Ile Cys Ala Leu Ala Gly Gly Phe Ala Lys Ala Asp Ile
       1385                1390                1395

Glu Met Ala Gly Pro Met Ala Ala Val Gly Leu Leu Ile Val Ser
       1400                1405                1410

Tyr Val Val Ser Gly Lys Ser Val Asp Met Tyr Ile Glu Arg Ala
       1415                1420                1425
```

-continued

```
Gly Asp Ile Thr Trp Glu Lys Asp Ala Glu Val Thr Gly Asn Ser
1430                1435                1440

Pro Arg Leu Asp Val Ala Leu Asp Glu Ser Gly Asp Phe Ser Leu
1445                1450                1455

Val Glu Asp Asp Gly Pro Pro Met Arg Glu Ile Ile Leu Lys Val
1460                1465                1470

Val Leu Met Ala Ile Cys Gly Met Asn Pro Ile Ala Ile Pro Phe
1475                1480                1485

Ala Ala Gly Ala Trp Tyr Val Tyr Val Lys Thr Gly Lys Arg Ser
1490                1495                1500

Gly Ala Leu Trp Asp Val Pro Ala Pro Lys Glu Val Lys Lys Gly
1505                1510                1515

Glu Thr Thr Asp Gly Val Tyr Arg Val Met Thr Arg Arg Leu Leu
1520                1525                1530

Gly Ser Thr Gln Val Gly Val Gly Val Met Gln Glu Gly Val Phe
1535                1540                1545

His Thr Met Trp His Val Thr Lys Gly Ser Ala Leu Arg Ser Gly
1550                1555                1560

Glu Gly Arg Leu Asp Pro Tyr Trp Gly Asp Val Lys Gln Asp Leu
1565                1570                1575

Val Ser Tyr Cys Gly Pro Trp Lys Leu Asp Ala Ala Trp Asp Gly
1580                1585                1590

His Ser Glu Val Gln Leu Leu Ala Val Pro Pro Gly Glu Arg Ala
1595                1600                1605

Arg Asn Ile Gln Thr Leu Pro Gly Ile Phe Lys Thr Lys Asp Gly
1610                1615                1620

Asp Ile Gly Ala Val Ala Leu Asp Tyr Pro Ala Gly Thr Ser Gly
1625                1630                1635

Ser Pro Ile Leu Asp Lys Cys Gly Arg Val Ile Gly Leu Tyr Gly
1640                1645                1650

Asn Gly Val Val Ile Lys Asn Gly Ser Tyr Val Ser Ala Ile Thr
1655                1660                1665

Gln Gly Arg Arg Glu Glu Thr Pro Val Glu Cys Phe Glu Pro
1670                1675                1680

Ser Met Leu Lys Lys Lys Gln Leu Thr Val Leu Asp Leu His Pro
1685                1690                1695

Gly Ala Gly Lys Thr Arg Arg Val Leu Pro Glu Ile Val Arg Glu
1700                1705                1710

Ala Ile Lys Thr Arg Leu Arg Thr Val Ile Leu Ala Pro Thr Arg
1715                1720                1725

Val Val Ala Ala Glu Met Glu Glu Ala Leu Arg Gly Leu Pro Val
1730                1735                1740

Arg Tyr Met Thr Thr Ala Val Asn Val Thr His Ser Gly Thr Glu
1745                1750                1755

Ile Val Asp Leu Met Cys His Ala Thr Phe Thr Ser Arg Leu Leu
1760                1765                1770

Gln Pro Ile Arg Val Pro Asn Tyr Asn Leu Tyr Ile Met Asp Glu
1775                1780                1785

Ala His Phe Thr Asp Pro Ser Ser Ile Ala Ala Arg Gly Tyr Ile
1790                1795                1800

Ser Thr Arg Val Glu Met Gly Glu Ala Ala Ile Phe Met Thr
1805                1810                1815
```

-continued

Ala Thr Pro Pro Gly Thr Arg Asp Ala Phe Pro Asp Ser Asn Ser
1820                1825                1830

Pro Ile Met Asp Thr Glu Val Glu Val Pro Glu Arg Ala Trp Ser
1835                1840                1845

Ser Gly Phe Asp Trp Val Thr Asp His Ser Gly Lys Thr Val Trp
1850                1855                1860

Phe Val Pro Ser Val Arg Asn Gly Asn Glu Ile Ala Ala Cys Leu
1865                1870                1875

Thr Lys Ala Gly Lys Arg Val Ile Gln Leu Ser Arg Lys Thr Phe
1880                1885                1890

Glu Thr Glu Phe Gln Lys Thr Lys His Gln Glu Trp Asp Phe Val
1895                1900                1905

Val Thr Thr Asp Ile Ser Glu Met Gly Ala Asn Phe Lys Ala Asp
1910                1915                1920

Arg Val Ile Asp Ser Arg Arg Cys Leu Lys Pro Val Ile Leu Asp
1925                1930                1935

Gly Glu Arg Val Ile Leu Ala Gly Pro Met Pro Val Thr His Ala
1940                1945                1950

Ser Ala Ala Gln Arg Arg Gly Arg Ile Gly Arg Asn Pro Asn Lys
1955                1960                1965

Pro Gly Asp Glu Tyr Leu Tyr Gly Gly Gly Cys Ala Glu Thr Asp
1970                1975                1980

Glu Asp His Ala His Trp Leu Glu Ala Arg Met Leu Leu Asp Asn
1985                1990                1995

Ile Tyr Leu Gln Asp Gly Leu Ile Ala Ser Leu Tyr Arg Pro Glu
2000                2005                2010

Ala Asp Lys Val Ala Ala Ile Glu Gly Glu Phe Lys Leu Arg Thr
2015                2020                2025

Glu Gln Arg Lys Thr Phe Val Glu Leu Met Lys Arg Gly Asp Leu
2030                2035                2040

Pro Val Trp Leu Ala Tyr Gln Val Ala Ser Ala Gly Ile Thr Tyr
2045                2050                2055

Thr Asp Arg Arg Trp Cys Phe Asp Gly Thr Thr Asn Asn Thr Ile
2060                2065                2070

Met Glu Asp Ser Val Pro Ala Glu Val Trp Thr Arg Tyr Gly Glu
2075                2080                2085

Lys Arg Val Leu Lys Pro Arg Trp Met Asp Ala Arg Val Cys Ser
2090                2095                2100

Asp His Ala Ala Leu Lys Ser Phe Lys Glu Phe Ala Ala Gly Lys
2105                2110                2115

Arg Gly Ala Ala Phe Gly Val Met Glu Ala Leu Gly Thr Leu Pro
2120                2125                2130

Gly His Met Thr Glu Arg Phe Gln Glu Ala Ile Asp Asn Leu Ala
2135                2140                2145

Val Leu Met Arg Ala Glu Thr Gly Ser Arg Pro Tyr Lys Ala Ala
2150                2155                2160

Ala Ala Gln Leu Pro Glu Thr Leu Glu Thr Ile Met Leu Leu Gly
2165                2170                2175

Leu Leu Gly Thr Val Ser Leu Gly Ile Phe Phe Val Leu Met Arg
2180                2185                2190

Asn Lys Gly Ile Gly Lys Met Gly Phe Gly Met Val Thr Leu Gly
2195                2200                2205

Ala Ser Ala Trp Leu Met Trp Leu Ser Glu Ile Glu Pro Ala Arg

```
       2210                2215                2220

Ile Ala Cys Val Leu Ile Val Val Phe Leu Leu  Val Val Leu
       2225                2230                2235

Ile Pro Glu Pro Glu Lys Gln Arg Ser Pro Gln Asp  Asn Gln Met
       2240                2245                2250

Ala Ile Ile Ile Met Val Ala Val Gly Leu Leu Gly  Leu Ile Thr
       2255                2260                2265

Ala Asn Glu Leu Gly Trp Leu Glu Arg Thr Lys Ser  Asp Leu Ser
       2270                2275                2280

His Leu Met Gly Arg Arg Glu Glu Gly Ala Thr Ile  Gly Phe Ser
       2285                2290                2295

Met Asp Ile Asp Leu Arg Pro Ala Ser Ala Trp Ala  Ile Tyr Ala
       2300                2305                2310

Ala Leu Thr Thr Phe Ile Thr Pro Ala Val Gln His  Ala Val Thr
       2315                2320                2325

Thr Ser Tyr Asn Asn Tyr Ser Leu Met Ala Met Ala  Thr Gln Ala
       2330                2335                2340

Gly Val Leu Phe Gly Met Gly Lys Gly Met Pro Phe  Tyr Ala Trp
       2345                2350                2355

Asp Phe Gly Val Pro Leu Leu Met Ile Gly Cys Tyr  Ser Gln Leu
       2360                2365                2370

Thr Pro Leu Thr Leu Ile Val Ala Ile Ile Leu Leu  Val Ala His
       2375                2380                2385

Tyr Met Tyr Leu Ile Pro Gly Leu Gln Ala Ala Ala  Ala Arg Ala
       2390                2395                2400

Ala Gln Lys Arg Thr Ala Ala Gly Ile Met Lys Asn  Pro Val Val
       2405                2410                2415

Asp Gly Ile Val Val Thr Asp Ile Asp Thr Met Thr  Ile Asp Pro
       2420                2425                2430

Gln Val Glu Lys Lys Met Gly Gln Val Leu Leu Ile  Ala Val Ala
       2435                2440                2445

Val Ser Ser Ala Ile Leu Ser Arg Thr Ala Trp Gly  Trp Gly Glu
       2450                2455                2460

Ala Gly Ala Leu Ile Thr Ala Ala Thr Ser Thr Leu  Trp Glu Gly
       2465                2470                2475

Ser Pro Asn Lys Tyr Trp Asn Ser Ser Thr Ala Thr  Ser Leu Cys
       2480                2485                2490

Asn Ile Phe Arg Gly Ser Tyr Leu Ala Gly Ala Ser  Leu Ile Tyr
       2495                2500                2505

Thr Val Thr Arg Asn Ala Gly Leu Val Lys Arg Arg  Gly Gly Gly
       2510                2515                2520

Thr Gly Glu Thr Leu Gly Glu Lys Trp Lys Ala Arg  Leu Asn Gln
       2525                2530                2535

Met Ser Ala Leu Glu Phe Tyr Ser Tyr Lys Lys Ser  Gly Ile Thr
       2540                2545                2550

Glu Val Cys Arg Glu Glu Ala Arg Arg Ala Leu Lys  Asp Gly Val
       2555                2560                2565

Ala Thr Gly Gly His Ala Val Ser Arg Gly Ser Ala  Lys Leu Arg
       2570                2575                2580

Trp Leu Val Glu Arg Gly Tyr Leu Gln Pro Tyr Gly  Lys Val Ile
       2585                2590                2595

Asp Leu Gly Cys Gly Arg Gly Gly Trp Ser Tyr Tyr  Ala Ala Thr
       2600                2605                2610
```

-continued

Ile Arg Lys Val Gln Glu Val Lys Gly Tyr Thr Lys Gly Gly Pro
2615             2620                 2625

Gly His Glu Glu Pro Met Leu Val Gln Ser Tyr Gly Trp Asn Ile
2630             2635                 2640

Val Arg Leu Lys Ser Gly Val Asp Val Phe His Met Ala Ala Glu
2645             2650                 2655

Pro Cys Asp Thr Leu Leu Cys Asp Ile Gly Glu Ser Ser Ser Ser
2660             2665                 2670

Pro Glu Val Glu Glu Ala Arg Thr Leu Arg Val Leu Ser Met Val
2675             2680                 2685

Gly Asp Trp Leu Glu Lys Arg Pro Gly Ala Phe Cys Ile Lys Val
2690             2695                 2700

Leu Cys Pro Tyr Thr Ser Thr Met Met Glu Thr Leu Glu Arg Leu
2705             2710                 2715

Gln Arg Arg Tyr Gly Gly Gly Leu Val Arg Val Pro Leu Ser Arg
2720             2725                 2730

Asn Ser Thr His Glu Met Tyr Trp Val Ser Gly Ala Lys Ser Asn
2735             2740                 2745

Thr Ile Lys Ser Val Ser Thr Thr Ser Gln Leu Leu Leu Gly Arg
2750             2755                 2760

Met Asp Gly Pro Arg Arg Pro Val Lys Tyr Glu Glu Asp Val Asn
2765             2770                 2775

Leu Gly Ser Gly Thr Arg Ala Val Val Ser Cys Ala Glu Ala Pro
2780             2785                 2790

Asn Met Lys Ile Ile Gly Asn Arg Ile Glu Arg Ile Arg Ser Glu
2795             2800                 2805

His Ala Glu Thr Trp Phe Phe Asp Glu Asn His Pro Tyr Arg Thr
2810             2815                 2820

Trp Ala Tyr His Gly Ser Tyr Glu Ala Pro Thr Gln Gly Ser Ala
2825             2830                 2835

Ser Ser Leu Ile Asn Gly Val Val Arg Leu Leu Ser Lys Pro Trp
2840             2845                 2850

Asp Val Val Thr Gly Val Thr Gly Ile Ala Met Thr Asp Thr Thr
2855             2860                 2865

Pro Tyr Gly Gln Gln Arg Val Phe Lys Glu Lys Val Asp Thr Arg
2870             2875                 2880

Val Pro Asp Pro Gln Glu Gly Thr Arg Gln Val Met Ser Met Val
2885             2890                 2895

Ser Ser Trp Leu Trp Lys Glu Leu Gly Lys His Lys Arg Pro Arg
2900             2905                 2910

Val Cys Thr Lys Glu Glu Phe Ile Asn Lys Val Arg Ser Asn Ala
2915             2920                 2925

Ala Leu Gly Ala Ile Phe Glu Glu Glu Lys Glu Trp Lys Thr Ala
2930             2935                 2940

Val Glu Ala Val Asn Asp Pro Arg Phe Trp Ala Leu Val Asp Lys
2945             2950                 2955

Glu Arg Glu His His Leu Arg Gly Glu Cys Gln Ser Cys Val Tyr
2960             2965                 2970

Asn Met Met Gly Lys Arg Glu Lys Lys Gln Gly Glu Phe Gly Lys
2975             2980                 2985

Ala Lys Gly Ser Arg Ala Ile Trp Tyr Met Trp Leu Gly Ala Arg
2990             2995                 3000

Phe Leu Glu Phe Glu Ala Leu Gly Phe Leu Asn Glu Asp His Trp
3005                3010                3015

Met Gly Arg Glu Asn Ser Gly Gly Val Glu Gly Leu Gly Leu
3020                3025                3030

Gln Arg Leu Gly Tyr Val Leu Glu Glu Met Ser Arg Ile Pro Gly
3035                3040                3045

Gly Arg Met Tyr Ala Asp Asp Thr Ala Gly Trp Asp Thr Arg Ile
3050                3055                3060

Ser Arg Phe Asp Leu Glu Asn Glu Ala Leu Ile Thr Asn Gln Met
3065                3070                3075

Glu Lys Gly His Arg Ala Leu Ala Leu Ala Ile Ile Lys Tyr Thr
3080                3085                3090

Tyr Gln Asn Lys Val Val Lys Val Leu Arg Pro Ala Glu Lys Gly
3095                3100                3105

Lys Thr Val Met Asp Ile Ile Ser Arg Gln Asp Gln Arg Gly Ser
3110                3115                3120

Gly Gln Val Val Thr Tyr Ala Leu Asn Thr Phe Thr Asn Leu Val
3125                3130                3135

Val Gln Leu Ile Arg Asn Met Glu Ala Glu Glu Val Leu Glu Met
3140                3145                3150

Gln Asp Leu Trp Leu Leu Arg Arg Ser Glu Lys Val Thr Asn Trp
3155                3160                3165

Leu Gln Ser Asn Gly Trp Asp Arg Leu Lys Arg Met Ala Val Ser
3170                3175                3180

Gly Asp Asp Cys Val Val Lys Pro Ile Asp Asp Arg Phe Ala His
3185                3190                3195

Ala Leu Arg Phe Leu Asn Asp Met Gly Lys Val Arg Lys Asp Thr
3200                3205                3210

Gln Glu Trp Lys Pro Ser Thr Gly Trp Asp Asn Trp Glu Glu Val
3215                3220                3225

Pro Phe Cys Ser His His Phe Asn Lys Leu His Leu Lys Asp Gly
3230                3235                3240

Arg Ser Ile Val Val Pro Cys Arg His Gln Asp Glu Leu Ile Gly
3245                3250                3255

Arg Ala Arg Val Ser Pro Gly Ala Gly Trp Ser Ile Arg Glu Thr
3260                3265                3270

Ala Cys Leu Ala Lys Ser Tyr Ala Gln Met Trp Gln Leu Leu Tyr
3275                3280                3285

Phe His Arg Arg Asp Leu Arg Leu Met Ala Asn Ala Ile Cys Ser
3290                3295                3300

Ser Val Pro Val Asp Trp Val Pro Thr Gly Arg Thr Thr Trp Ser
3305                3310                3315

Ile His Gly Lys Gly Glu Trp Met Thr Thr Glu Asp Met Leu Val
3320                3325                3330

Val Trp Asn Arg Val Trp Ile Glu Glu Asn Asp His Met Glu Asp
3335                3340                3345

Lys Thr Pro Val Thr Lys Trp Thr Asp Ile Pro Tyr Leu Gly Lys
3350                3355                3360

Arg Glu Asp Leu Trp Cys Gly Ser Leu Ile Gly His Arg Pro Arg
3365                3370                3375

Thr Thr Trp Ala Glu Asn Ile Lys Asn Thr Val Asn Met Met Arg
3380                3385                3390

Arg Ile Ile Gly Asp Glu Glu Lys Tyr Val Asp Tyr Leu Ser Thr

```
                3395               3400                3405

Gln Val  Arg Tyr Leu Gly Glu  Glu Gly Ser Thr Pro  Gly Val Leu
    3410              3415                3420

<210> SEQ ID NO 3
<211> LENGTH: 1512
<212> TYPE: DNA
<213> ORGANISM: Artificial Sequence
<220> FEATURE:
<223> OTHER INFORMATION: Synthetic sequence

<400> SEQUENCE: 3
atcaggtgca taggagtcag caatagggac tttgtggaag gtatgtcagg tgggacttgg      60
gttgatgttg tcttggaaca tggaggttgt gttaccgtaa tggcacagga caaaccgact     120
gtcgacatag agctggttac aacaacagtc agcaacatgg cggaggtaag atcctactgc     180
tatgaggcat caatatcgga catggcttcg dacagccgct gcccaacaca aggtgaagcc     240
taccttgaca gcaatcaga cactcaatat gtctgcaaaa gaacgttagt ggacagaggc      300
tggggaaatg gatgtggact ttttggcaaa gggagcctgg tgacatgcgc taagtttgct     360
tgctctaaga aaatgaccgg gaagagcatc agccagaga atctggagta ccggataatg      420
ctgtcagttc atggctccca gcacagtggg atgatcgtta atgatacagg acatgaaact     480
gatgagaata gagcgaaggt tgagataacg cccaattcac caagagccga agccaccctg     540
gggggttttg gaagcctagg acttgattgt gaaccgagga caggccttga cttttcagat    600
ttgtattact tgactatgaa taacaagcac tggttggttc acaaggagtg gttccacgac     660
attccattac cttggcacgc tggggcagac accggaactc cacactggaa caacaaagaa     720
gcactggtag agttcaagga cgcacatgcc aaaaggcaga ctgtcgtggt tctagggagt    780
caagaaggag cagttcacac ggcccttgct ggagctctgg aggctgagat ggatggtgca     840
aagggaaggc tgtcctctgg ccacttgaaa tgtcgcctga aaatggacaa acttagattg    900
aagggcgtgt catactcctt gtgtaccgca gcgttcacat tcactaagat cccggctgaa     960
acactgcacg gacagtcac agtggaggta cagtacgcag ggacagatgg accttgcaag   1020
gttccagctc agatggcggt ggacatgcaa actctgaccc cagttgggag gttgataacc    1080
gctaaccctg taatcactga aagcactgag aactccaaga tgatgctgga actggatcca     1140
ccatttgggg actcttacat tgtcatagga gtcgggaaa agaagatcac ccaccactgg   1200
cacaggagtg gcagcaccat tggaaaagca tttgaagcca ctgtgagagg tgccaagaga     1260
atggcagtct tgggagacac agcctgggac tttggatcag ttgggggtgc tctcaactca     1320
ctgggcaagg gcatccatca aattttgga gcagctttca atcattgtt tggaggaatg      1380 tcctggttct cacaaattct cattggaacg ttgctggtgt ggttgggtct gaatacaaag     1440
aatggatcta tttcccttat gtgcttggcc ttaggggag tgttgatctt cttatccaca     1500
gccgtctctg ct                                                         1512

<210> SEQ ID NO 4
<211> LENGTH: 504
<212> TYPE: PRT
<213> ORGANISM: Artificial Sequence
<220> FEATURE:
<223> OTHER INFORMATION: Synthetic sequence

<400> SEQUENCE: 4

Ile Arg Cys Ile Gly Val Ser Asn Arg Asp Phe Val Glu Gly Met Ser
1               5                   10                  15
```

-continued

Gly Gly Thr Trp Val Asp Val Leu Glu His Gly Gly Cys Val Thr
            20              25              30

Val Met Ala Gln Asp Lys Pro Thr Val Asp Ile Glu Leu Val Thr Thr
        35              40              45

Thr Val Ser Asn Met Ala Glu Val Arg Ser Tyr Cys Tyr Glu Ala Ser
50              55              60

Ile Ser Asp Met Ala Ser Asp Ser Arg Cys Pro Thr Gln Gly Glu Ala
65              70              75              80

Tyr Leu Asp Lys Gln Ser Asp Thr Gln Tyr Val Cys Lys Arg Thr Leu
            85              90              95

Val Asp Arg Gly Trp Gly Asn Gly Cys Gly Leu Phe Gly Lys Gly Ser
            100             105             110

Leu Val Thr Cys Ala Lys Phe Ala Cys Ser Lys Lys Met Thr Gly Lys
            115             120             125

Ser Ile Gln Pro Glu Asn Leu Glu Tyr Arg Ile Met Leu Ser Val His
    130             135             140

Gly Ser Gln His Ser Gly Met Ile Val Asn Asp Thr Gly His Glu Thr
145             150             155             160

Asp Glu Asn Arg Ala Lys Val Glu Ile Thr Pro Asn Ser Pro Arg Ala
                165             170             175

Glu Ala Thr Leu Gly Gly Phe Gly Ser Leu Gly Leu Asp Cys Glu Pro
            180             185             190

Arg Thr Gly Leu Asp Phe Ser Asp Leu Tyr Tyr Leu Thr Met Asn Asn
        195             200             205

Lys His Trp Leu Val His Lys Glu Trp Phe His Asp Ile Pro Leu Pro
    210             215             220

Trp His Ala Gly Ala Asp Thr Gly Thr Pro His Trp Asn Asn Lys Glu
225             230             235             240

Ala Leu Val Glu Phe Lys Asp Ala His Ala Lys Arg Gln Thr Val Val
            245             250             255

Val Leu Gly Ser Gln Glu Gly Ala Val His Thr Ala Leu Ala Gly Ala
            260             265             270

Leu Glu Ala Glu Met Asp Gly Ala Lys Gly Arg Leu Ser Ser Gly His
        275             280             285

Leu Lys Cys Arg Leu Lys Met Asp Lys Leu Arg Leu Lys Gly Val Ser
    290             295             300

Tyr Ser Leu Cys Thr Ala Ala Phe Thr Phe Thr Lys Ile Pro Ala Glu
305             310             315             320

Thr Leu His Gly Thr Val Thr Val Glu Val Gln Tyr Ala Gly Thr Asp
            325             330             335

Gly Pro Cys Lys Val Pro Ala Gln Met Ala Val Asp Met Gln Thr Leu
            340             345             350

Thr Pro Val Gly Arg Leu Ile Thr Ala Asn Pro Val Ile Thr Glu Ser
        355             360             365

Thr Glu Asn Ser Lys Met Met Leu Glu Leu Asp Pro Pro Phe Gly Asp
    370             375             380

Ser Tyr Ile Val Ile Gly Val Gly Glu Lys Lys Ile Thr His His Trp
385             390             395             400

His Arg Ser Gly Ser Thr Ile Gly Lys Ala Phe Glu Ala Thr Val Arg
            405             410             415

Gly Ala Lys Arg Met Ala Val Leu Gly Asp Thr Ala Trp Asp Phe Gly
            420             425             430

```
Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Val Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 5
<211> LENGTH: 1245
<212> TYPE: DNA
<213> ORGANISM: Artificial Sequence
<220> FEATURE:
<223> OTHER INFORMATION: Synthetic sequence

<400> SEQUENCE: 5
atcaggtgca taggagtcag caatagggac tttgtggaag gtatgtcagg tgggacttgg      60
gttgatgttg tcttggaaca tggaggttgt gttaccgtaa tggcacagga caaaccgact     120
gtcgacatag agctggttac aacaacagtc agcaacatgg cggaggtaag atcctactgc     180
tatgaggcat caatatcgga catggcttcg gacagccgct gcccaacaca aggtgaagcc     240
taccttgaca agcaatcaga cactcaatat gtctgcaaaa gaacgttagt ggacagaggc     300
tggggaaatg gatgtggact ttttggcaaa gggagcctgg tgacatgcgc taagtttgct     360
tgctctaaga aaatgaccgg gaagagcatc agccagaga atctggagta ccggataatg     420
ctgtcagttc atggctccca gcacagtggg atgatcgtta atgatacagg acatgaaact     480
gatgagaata gagcgaaggt tgagataacg cccaattcac caagagccga agccaccctg     540
gggggttttg gaagcctagg acttgattgt gaaccgagga caggccttga cttttcagat     600
ttgtattact tgactatgaa taacaagcac tggttggttc acaaggagtg gttccacgac     660
attccattac cttggcacgc tggggcagac accggaactc cacactgaa caacaaagaa     720 gcactggtag agttcaagga cgcacatgcc aaaaggcaga ctgtcgtggt tctagggagt     780
caagaaggag cagttcacac ggcccttgct ggagctctgg aggctgagat ggatggtgca     840
aagggaaggc tgtcctctgg ccacttgaaa tgtcgcctga aatgacaa acttagattg     900 aagggcgtgt catactcctt gtgtaccgca gcgttcacat tcactaagat cccggctgaa     960
acactgcacg gacagtcac agtggaggta cagtacgcag gacagatgg accttgcaag    1020 gttccagctc agatggcggt ggacatgcaa actctgaccc cagttgggag gttgataacc    1080
gctaaccctg taatcactga aagcactgag aactccaaga tgatgctgga actggatcca    1140
ccatttgggg actcttacat tgtcataggga gtcgggaaa agaagatcac ccaccactgg    1200
cacaggagtg gcagcaccat tggaaaagca tttgaagcca ctgtg                    1245

<210> SEQ ID NO 6
<211> LENGTH: 415
<212> TYPE: PRT
<213> ORGANISM: Artificial Sequence
<220> FEATURE:
<223> OTHER INFORMATION: Synthetic sequence

<400> SEQUENCE: 6

Ile Arg Cys Ile Gly Val Ser Asn Arg Asp Phe Val Glu Gly Met Ser
1               5                   10                  15
```

Gly Gly Thr Trp Val Asp Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val
                405                 410                 415

<210> SEQ ID NO 7
<211> LENGTH: 1242

```
<212> TYPE: DNA
<213> ORGANISM: Artificial Sequence
<220> FEATURE:
<223> OTHER INFORMATION: Synthetic sequence

<400> SEQUENCE: 7
atcaggtgca taggagtcag caatagggac tttgtggaag gtatgtcagg tgggacttgg      60
gttgatgttg tcttggaaca tggaggttgt gttaccgtaa tggcacagga caaaccgact     120
gtcgacatag agctggttac aacaacagtc agcaacatgg cggaggtaag atcctactgc     180
tatgaggcat caatatcgga catggcttcg acagccgct gcccaacaca aggtgaagcc      240
taccttgaca agcaatcaga cactcaatat gtctgcaaaa gaacgttagt ggacagaggc     300
tggggaaatg gatgtggact ttttggcaaa gggagcctgg tgacatgcgc taagtttgct     360
tgctctaaga aaatgaccgg aagagcatc cagccagaga atctggagta ccggataatg      420
ctgtcagttc atggctccca gcacagtggg atgatcgtta atgatacagg acatgaaact     480
gatgagaata gagcgaaggt tgagataacg cccaattcac caagagccga agccaccctg     540
ggggtttttg aagcctagg acttgattgt gaaccgagga caggccttga cttttcagat      600
ttgtattact tgactatgaa taacaagcac tggttggttc acaaggagtg gttccacgac     660
attccattac cttggcacgc tggggcagac accggaactc cacactggaa caacaaagaa     720
gcactggtag agttcaagga cgcacatgcc aaaaggcaga ctgtcgtggt tctagggagt     780
caagaaggag cagttcacac ggcccttgct ggagctctgg aggctgagat ggatggtgca     840
aagggaaggc tgtcctctgg ccacttgaaa tgtcgcctga aaatgacaa acttagattg      900
aagggcgtgt catactcctt gtgtaccgca gcgttcacat tcactaagat cccggctgaa     960
acactgcacg ggacagtcac agtggaggta cagtacgcag ggacagatgg accttgcaag    1020
gttccagctc agatggcggt ggacatgcaa actctgaccc cagttgggag gttgataacc    1080
gctaaccctg taatcactga aagcactgag aactccaaga tgatgctgga actggatcca    1140
ccatttgggg actcttacat tgtcatagga gtcggggaaa agaagatcac ccaccactgg    1200
cacaggagtg gcagcaccat tggaaaagca tttgaagcca ct                       1242

<210> SEQ ID NO 8
<211> LENGTH: 319
<212> TYPE: PRT
<213> ORGANISM: Artificial Sequence
<220> FEATURE:
<223> OTHER INFORMATION: Synthetic sequence

<400> SEQUENCE: 8

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala
305                 310                 315

<210> SEQ ID NO 9
<211> LENGTH: 1212
<212> TYPE: DNA
<213> ORGANISM: Artificial Sequence
<220> FEATURE:
<223> OTHER INFORMATION: Synthetic sequence

<400> SEQUENCE: 9
atcaggtgca taggagtcag caataggggac tttgtggaag gtatgtcagg tgggacttgg      60
gttgatgttg tcttggaaca tggaggttgt gttaccgtaa tggcacagga caaaccgact     120
gtcgacatag agctggttac aacaacagtc agcaacatgg cggaggtaag atcctactgc     180
tatgaggcat caatatcgga catggcttcg gacagccgct gcccaacaca aggtgaagcc     240
taccttgaca agcaatcaga cactcaatat gtctgcaaaa gaacgttagt ggacagaggc     300
tggggaaatg gatgtggact ttttggcaaa gggagcctgg tgacatgcgc taagtttgct     360
tgctctaaga aaatgaccgg gaagagcatc agccagaga atctggagta ccggataatg     420
ctgtcagttc atggctccca gcacagtggg atgatcgtta atgatacagg acatgaaact     480
gatgagaata gagcgaaggt tgagataacg cccaattcac caagagccga agccaccctg     540
gggggttttg gaagcctagg acttgattgt gaaccgagga caggccttga cttttcagat     600
ttgtattact tgactatgaa taacaagcac tggttggttc acaaggagtg gttccacgac     660
attccattac cttggcacgc tggggcagac accggaactc cacactggaa caacaaagaa     720
gcactggtag agttcaagga cgcacatgcc aaaaggcaga ctgtcgtggt tctagggagt     780
caagaaggag cagttcacac ggcccttgct ggagctctgg aggctgagat ggatggtgca     840
aagggaaggc tgtcctctgg ccacttgaaa tgtcgcctga aaatggacaa acttagattg     900

```
aagggcgtgt catactcctt gtgtaccgca gcgttcacat tcactaagat cccggctgaa    960
acactgcacg ggacagtcac agtggaggta cagtacgcag ggacagatgg accttgcaag   1020
gttccagctc agatggcggt ggacatgcaa actctgaccc cagttgggag gttgataacc   1080
gctaaccctg taatcactga aagcactgag aactccaaga tgatgctgga actggatcca   1140
ccatttgggg actcttacat tgtcatagga gtcggggaaa agaagatcac ccaccactgg   1200
cacaggagtg gc                                                       1212
```

<210> SEQ ID NO 10
<211> LENGTH: 404
<212> TYPE: PRT
<213> ORGANISM: Artificial Sequence
<220> FEATURE:
<223> OTHER INFORMATION: Synthetic sequence

<400> SEQUENCE: 10

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300
```

```
Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
            325                 330                 335

Gly Pro Cys Lys Val Pro Ala Gln Met Ala Val Asp Met Gln Thr Leu
        340                 345                 350

Thr Pro Val Gly Arg Leu Ile Thr Ala Asn Pro Val Ile Thr Glu Ser
    355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly

<210> SEQ ID NO 11
<211> LENGTH: 558
<212> TYPE: DNA
<213> ORGANISM: Artificial Sequence
<220> FEATURE:
<223> OTHER INFORMATION: Synthetic sequence

<400> SEQUENCE: 11
ggcacagata ctagtgtcgg aattgttggc ctcctgctga ccacagccat ggcagtggag    60
gtcactagac gtgggaatgc atactatatg tacttggaca gaagcgatgc tggggaggcc   120
atatcttttc caaccacaat ggggatgaat aagtgttata tacagatcat ggatcttgga   180
cacatgtgtg atgccaccat gagctatgaa tgccctatgc tggatgaggg ggtagaacca   240
gatgacgtcg attgttggtg caacacgacg tcaacttggg ttgtgtacgg aacctgccac   300
cacaaaaaag gtgaagcacg gagatctaga agagctgtga cgctcccctc ccattccact   360
aggaagctgc aaacgcggtc gcagacctgg ttggaatcaa gagaatacac aaagcacctg   420
attagagtcg aaaattggat attcaggaac cctggcttcg cgttagcagc agctgccatc   480
gcttggcttt tgggaagctc aacgagccaa aaagtcatat acttggtcat gatactgctg   540
attgccccgg catacagc                                                 558

<210> SEQ ID NO 12
<211> LENGTH: 186
<212> TYPE: PRT
<213> ORGANISM: Artificial Sequence
<220> FEATURE:
<223> OTHER INFORMATION: Synthetic sequence

<400> SEQUENCE: 12

Gly Thr Asp Thr Ser Val Gly Ile Val Gly Leu Leu Leu Thr Thr Ala
1               5                   10                  15

Met Ala Val Glu Val Thr Arg Arg Gly Asn Ala Tyr Tyr Met Tyr Leu
            20                  25                  30

Asp Arg Ser Asp Ala Gly Glu Ala Ile Ser Phe Pro Thr Thr Met Gly
        35                  40                  45

Met Asn Lys Cys Tyr Ile Gln Ile Met Asp Leu Gly His Met Cys Asp
    50                  55                  60

Ala Thr Met Ser Tyr Glu Cys Pro Met Leu Asp Glu Gly Val Glu Pro
65                  70                  75                  80

Asp Asp Val Asp Cys Trp Cys Asn Thr Thr Ser Thr Trp Val Val Tyr
                85                  90                  95
```

Gly Thr Cys His His Lys Lys Gly Glu Ala Arg Ser Arg Arg Ala
            100                 105                 110

Val Thr Leu Pro Ser His Ser Thr Arg Lys Leu Gln Thr Arg Ser Gln
        115                 120                 125

Thr Trp Leu Glu Ser Arg Glu Tyr Thr Lys His Leu Ile Arg Val Glu
    130                 135                 140

Asn Trp Ile Phe Arg Asn Pro Gly Phe Ala Leu Ala Ala Ala Ala Ile
145                 150                 155                 160

Ala Trp Leu Leu Gly Ser Ser Thr Ser Gln Lys Val Ile Tyr Leu Val
                165                 170                 175

Met Ile Leu Leu Ile Ala Pro Ala Tyr Ser
            180                 185

<210> SEQ ID NO 13
<211> LENGTH: 1056
<212> TYPE: DNA
<213> ORGANISM: Artificial Sequence
<220> FEATURE:
<223> OTHER INFORMATION: Synthetic sequence

<400> SEQUENCE: 13
gatgtggggt gctcggtgga cttctcaaag aaggaaacga gatgcggtac aggggtgttc      60
gtctataacg acgttgaagc ttggagggac aggtacaagt accatcctga ctcccctcgt     120
agattggcag cagcagtcaa gcaagcctgg gaagatggga tctgtgggat ctcctctgtt     180
tcaagaatgg aaaacatcat gtggagatca gtagaagggg agctcaacgc aatcctggaa     240
gagaatggag ttcaactgac ggtcgttgtg ggatctgtaa aaacccccat gtggagaggt     300
ccacagagat tgcccgtgcc tgtgaacgag ctgccccatg gctggaaggc ttggggggaaa    360
tcgtacttcg tcagggcagc aaagacaaat aacagctttg tcgtggatgg tgacacactg     420
aaggaatgcc cactcaaaca tagagcatgg aacagctttc ttgtgaggga tcatgggttc     480
ggggtatttc acactagtgt ctggctcaag gttagaaag attattcatt agagtgtgat      540
ccagccgtca ttggaacagc cgctaaggga aaggaggctg tgcacagtga tctaggctac     600
tggattgaga gtgagaagaa cgacacatgg aggctgaaga gggcccacct gatcgagatg     660
aaaacatgtg aatggccaaa gtcccacaca ttgtggacag atggaataga agaaagtgat     720
ctgatcatac ccagtctttt agctgggcca ctcagccatc acaacaccag agagggctac     780
aggacccaaa tgaaagggcc atggcatagt gaagagcttg aaattcggtt tgaggaatgc     840
ccaggcacta aggtccacgt ggaggaaaca tgtggaacaa gaggaccatc tctgagatca     900
accactgcaa gcggaagggt gatcgaggaa tggtgctgca gggagtgcac aatgccccca     960
ctgtcgttcc gggctaaaga tggttgttgg tatggaatgg agataaggcc caggaaagaa    1020
ccagaaagta acttagtaag gtcaatggtg actgca                              1056

<210> SEQ ID NO 14
<211> LENGTH: 352
<212> TYPE: PRT
<213> ORGANISM: Artificial Sequence
<220> FEATURE:
<223> OTHER INFORMATION: Synthetic sequence

<400> SEQUENCE: 14

Asp Val Gly Cys Ser Val Asp Phe Ser Lys Lys Glu Thr Arg Cys Gly
1               5                   10                  15

Thr Gly Val Phe Val Tyr Asn Asp Val Glu Ala Trp Arg Asp Arg Tyr
            20                  25                  30

Lys Tyr His Pro Asp Ser Pro Arg Leu Ala Ala Ala Val Lys Gln
            35                  40                  45

Ala Trp Glu Asp Gly Ile Cys Gly Ile Ser Ser Val Ser Arg Met Glu
 50                  55                  60

Asn Ile Met Trp Arg Ser Val Glu Gly Glu Leu Asn Ala Ile Leu Glu
 65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
            115                 120                 125

Thr Asn Asn Ser Phe Val Val Asp Gly Asp Thr Leu Lys Glu Cys Pro
            130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Ala Lys Gly Lys Glu
            180                 185                 190

Ala Val His Ser Asp Leu Gly Tyr Trp Ile Glu Ser Glu Lys Asn Asp
            195                 200                 205

Thr Trp Arg Leu Lys Arg Ala His Leu Ile Glu Met Lys Thr Cys Glu
            210                 215                 220

Trp Pro Lys Ser His Thr Leu Trp Thr Asp Gly Ile Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Met Lys Gly Pro Trp His Ser Glu Glu
            260                 265                 270

Leu Glu Ile Arg Phe Glu Glu Cys Pro Gly Thr Lys Val His Val Glu
            275                 280                 285

Glu Thr Cys Gly Thr Arg Gly Pro Ser Leu Arg Ser Thr Thr Ala Ser
            290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

<210> SEQ ID NO 15
<211> LENGTH: 14233
<212> TYPE: DNA
<213> ORGANISM: Artificial Sequence
<220> FEATURE:
<223> OTHER INFORMATION: Sythetic sequence

<400> SEQUENCE: 15
acgaagacaa acaaaccatt attatcatta aaaggctcag gagaaacttt aacagtaatc        60
aaaatgtctg ttacagtcaa gagaatcatt gacaacacag tcatagttcc aaaacttcct       120
gcaaatgagg atccagtgga atacccggca gattacttca gaaaatcaaa ggagattcct       180
ctttacatca atactacaaa aagtttgtca gatctaagag gatatgtcta ccaaggcctc       240

```
aaatccggaa atgtatcaat catacatgtc aacagctact tgtatggagc attaaaggac    300
atccggggta agttggataa agattggtca agtttcggaa taaacatcgg gaaagcaggg    360
gatacaatcg gaatatttga ccttgtatcc ttgaaagccc tggacggcgt acttccagat    420
ggagtatcgg atgcttccag aaccagcgca gatgacaaat ggttgccttt gtatctactt    480
ggcttataca gagtgggcag aacacaaatg cctgaataca gaaaaaagct catggatggg    540
ctgacaaatc aatgcaaaat gatcaatgaa cagtttgaac ctcttgtgcc agaaggtcgt    600 gacattttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca agattgtgc tgcattggca acatttggac acctctgcaa ataaccgga    780 atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960 tggggggcaat tgacagctct tctgctcaga tccaccagag caaggaatgc ccgacagcct   1020
gatgacattg agtatacatc tcttactaca gcaggtttgt tgtacgctta gcagtagga    1080 tcctctgccg acttggcaca acagttttgt gttggagata caaatacac tccagatgat   1140 agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gaccctataa ttctcagatc acctattata tattatgcta catatgaaaa   1380
aaactaacag atatcatgga taatctcaca aaagttcgtg agtatctcaa gtcctactct   1440
cgtctagatc aggcggtagg agagatagat gagatcgaag cacaacgagc tgaaaagtcc   1500
aattatgagt tgttccaaga ggacggagtg gaagagcata ctaggccctc ttattttcag   1560
gcagcagatg attctgacac agaatctgaa ccagaaattg aagacaatca aggcttgtat   1620
gtaccagatc cggaagctga gcaagttgaa ggctttatac aggggccttt agatgactat   1680
gcagatgagg acgtggatgt tgtattcact tcggactgga acagcctga gcttgaatcc   1740 gacgagcatg gaaagacctt acggttgaca ttgccagagg gtttaagtgg agagcagaaa   1800
tcccagtggc ttttgacgat taaagcagtc gttcaaagtg ccaaacactg gaatctggca   1860
gagtgcacat ttgaagcatc gggagaaggg gtcatcataa aaaagcgcca gataactccg   1920
gatgtatata aggtcactcc agtgatgaac acacatccgt accaatcaga agccgtatca   1980
gatgtttggt ctctctcaaa gacatccatg actttccaac ccaagaaagc aagtcttcag   2040
cctctcacca tatccttgga tgaattgttc tcatctagag gagaattcat ctctgtcgga   2100
ggtaacggac gaatgtctca taagaggcc atcctgctcg gtctgaggta caaaaagttg   2160
tacaatcagg cgagagtcaa atattctctg tagactatga aaaaagtaa cagatatcac   2220 aatctaagtg ttatcccaat ccattcatca tgagttcctt aaagaagatt ctcggtctga   2280
aggggaaagg taagaaatct aagaaattag ggatcgcacc ccccccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaaaatc ttggcttttt   2580
tgggttcttc taatctaaag gccactccag cggtattggc agatcaaggt caaccagagt   2640
```

```
atcacgctca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctagc ttccagcttc tgaacaatcc ccggtttact cagtctctcc taattccagc    3000
ctttcgaaca actaatatcc tgtcttttct atccctatga aaaaactaa cagagatcga    3060 tctgtttcct tgacaccatg aagtgccttt tgtacttagc ttttttattc atcggggtga    3120
attgcaagtt caccatagtt tttccacaca accgaaaagg aaactggaaa atgttccttt    3180
ccaattacca ttattgcccg tcaagctcag atttaaattg gcataatgac ttaataggca    3240
cagccttaca agtcaaaatg cccaagagtc acaaggctat tcaagcagac ggttggatgt    3300
gtcatgcttc caaatgggtc actacttgtg atttccgctg gtacggaccg gagtatataa    3360
cacattccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc tgaagcagcg attgtccagg tgactcctca ccatgtgctt gttgatgaat    3540
acacaggaga atgggttgat tcacagttca tcaacggaaa atgcagcaat gacatatgcc    3600
ccactgtcca taactccaca acctggcatt ccgactataa ggtcaaaggg ctatgtgatt    3660
ctaacctcat ttccatggac atcaccttct tctcagagga cggagagcta tcatccctag    3720
gaaaggaggg cacagggttc agaagtaact actttgctta tgaaactgga gacaaggcct    3780
gcaaaatgca gtactgcaag cattgggggag tcagactccc atcaggtgtc tggttcgaga    3840
tggctgataa ggatctcttt gctgcagcca gattccctga tgcccagaa gggtcaagta    3900 tctctgctcc atctcagacc tcagtggatg taagtctcat tcaggacgtt gagaggatct    3960
tggattattc cctctgccaa gaaacctgga gcaaaatcag agcgggtctt cccatctctc    4020
cagtggatct cagctatctt gctcctaaaa acccaggaac cggtcctgtc tttaccataa    4080
tcaatggtac cctaaaatac tttgagacca gatacatcag agtcgatatt gctgctccaa    4140
tcctctcaag aatggtcgga atgatcagtg aactaccac agaaagggaa ctgtgggatg    4200
actgggctcc atatgaagac gtggaaattg gacccaatgg agttctgagg accagttcag    4260
gatataagtt tccttatat atgattggac atggtatgtt ggactccgat cttcatctta    4320
gctcaaaggc tcaggtgttt gaacatcctc acattcaaga cgctgcttcg cagcttcctg    4380
atgatgagac tttattttt ggtgatactg ggctatccaa aaatccaatc gagtttgtag    4440
aaggttggtt cagtagttgg aagagctcta ttgcctcttt ttgctttatc ataggttaa    4500 tcattggact attcttggtt ctccgagttg gtatttatct ttgcattaaa ttaaagcaca    4560
ccaagaaaag acagatttat acagacatag agatgaaccg acttggaaag taactcaaat    4620
cctgcacaac agattcttca tgtttgaacc aaatcaactt gtgatatcat gctcaaagag    4680
gccttaatta tattttaatt tttaatttt atgaaaaaaa ctaacagcaa tcatggaagt    4740
ccacgatttt gagaccgacg agttcaatga tttcaatgaa gatgactatg ccacaagaga    4800
attcctgaat cccgatgagc gcatgacgta cttgaatcat gctgattaca atttgaattc    4860
tcctctaatt agtgatgata ttgacaattt gatcaggaaa ttcaattctc ttccgattcc    4920
ctcgatgtgg gatagtaaga actgggatgg agttcttgag atgttaacat catgtcaagc    4980
```

```
caatcccatc tcaacatctc agatgcataa atggatggga agttggttaa tgtctgataa      5040
tcatgatgcc agtcaagggt atagttttt acatgaagtg gacaaagagg cagaaataac       5100
atttgacgtg gtggagacct tcatccgcgg ctggggcaac aaaccaattg aatacatcaa      5160
aaaggaaaga tggactgact cattcaaaat tctcgcttat ttgtgtcaaa agttttttgga    5220 cttacacaag ttgacattaa tcttaaatgc tgtctctgag gtggaattgc tcaacttggc      5280
gaggactttc aaaggcaaag tcagaagaag ttctcatgga acgaacatat gcaggattag     5340
ggttcccagc ttgggtccta cttttatttc agaaggatgg gcttacttca agaaacttga     5400
tattctaatg gaccgaaact ttctgttaat ggtcaaagat gtgattatag ggaggatgca     5460
aacggtgcta tccatggtat gtagaataga caacctgttc tcagagcaag acatcttctc    5520
ccttctaaat atctcagaa ttggagataa aattgtggag aggcagggaa attttttctta    5580 tgacttgatt aaaatggtgg aaccgatatg caacttgaag ctgatgaaat tagcaagaga    5640
atcaaggcct ttagtcccac aattccctca ttttgaaaat catatcaaga cttctgttga    5700 tgaagggca aaaattgacc gaggtataag attcctccat gatcagataa tgagtgtgaa     5760
aacagtggat ctcacactgg tgatttatgg atcgttcaga cattggggtc atccttttat    5820
agattattac actggactag aaaaattaca ttcccaagta accatgaaga aagatattga    5880
tgtgtcatat gcaaaagcac ttgcaagtga tttagctcgg attgttctat ttcaacagtt    5940
caatgatcat aaaaagtggt tcgtgaatgg agacttgctc cctcatgatc atccctttaa    6000
aagtcatgtt aaagaaaata catggcccac agctgctcaa gttcaagatt ttggagataa    6060
atggcatgaa cttccgctga ttaaatgttt tgaaataccc gacttactag acccatcgat    6120
aatatactct gacaaaagtc attcaatgaa taggtcagag gtgttgaaac atgtccgaat    6180
gaatccgaac actcctatcc ctagtaaaaa ggtgttgcag actatgttgg acacaaaggc    6240
taccaattgg aaagaatttc ttaaagagat tgatgagaag ggcttagatg atgatgatct    6300
aattattggt cttaaaggaa aggagaggga actgaagttg gcaggtagat tttctcccct    6360
aatgtcttgg aaattgcgag atactttgt aattaccgaa tatttgataa agactcattt      6420
cgtccctatg tttaaaggcc tgacaatggc ggacgatcta actgcagtca ttaaaaagat    6480
gttagattcc tcatccggcc aaggattgaa gtcatatgag gcaatttgca tagccaatca    6540
cattgattac gaaaaatgga ataaccacca aaggaagtta tcaaacggcc cagtgttccg    6600
agttatgggc cagttcttag gttatccatc cttaatcgag agaactcatg aattttttga    6660
gaaaagtctt atatactaca atggaagacc agacttgatg cgtgttcaca acaacacact    6720
gatcaattca acctcccaac gagtttgttg gcaaggacaa gagggtggac tggaaggtct    6780
acggcaaaaa ggatggagta tcctcaatct actggttatt caaagagagg ctaaaatcag    6840
aaacactgct gtcaaagtct tggcacaagg tgataatcaa gttatttgca cacagtataa    6900
aacgaagaaa tcgagaaacg ttgtagaatt acagggtgct ctcaatcaaa tggtttctaa    6960
taatgagaaa attatgactg caatcaaaat agggacaggg aagttaggac tttgataaa     7020 tgacgatgag actatgcaat ctgcagatta cttgaattat ggaaaaatac cgattttccg    7080
tggagtgatt agagggttag agaccaagag atggtcacga gtgacttgtg tcaccaatga    7140 ccaaatacccc acttgtgcta atataatgag ctcagtttcc acaaatgctc tcaccgtagc    7200
tcattttgct gagaacccaa tcaatgccat gatacagtac aattattttg ggacatttgc    7260
tagactcttg ttgatgatgc atgatcctgc tcttcgtcaa tcattgtatg aagttcaaga    7320
taagataccg ggcttgcaca gttctacttt caaatacgcc atgttgtatt tggaccccttc    7380
```

```
cattggagga gtgtcgggca tgtctttgtc caggttttg attagagcct tcccagatcc      7440
cgtaacagaa agtctctcat tctggagatt catccatgta catgctcgaa gtgagcatct      7500
gaaggagatg agtgcagtat ttggaaaccc cgagatagcc aagtttcgaa taactcacat      7560
agacaagcta gtagaagatc caacctctct gaacatcgct atgggaatga gtccagcgaa      7620
cttgttaaag actgaggtta aaaaatgctt aatcgaatca agacaaacca tcaggaacca      7680
ggtgattaag gatgcaacca tatatttgta tcatgaagag gatcggctca gaagtttctt      7740
atggtcaata aatcctctgt tccctagatt tttaagtgaa ttcaaatcag gcactttttt      7800
gggagtcgca gacgggctca tcagtctatt tcaaaattct cgtactattc ggaactcctt      7860
taagaaaaag tatcataggg aattggatga tttgattgtg aggagtgagg tatcctcttt      7920
gacacattta gggaaacttc atttgagaag gggatcatgt aaaatgtgga catgttcagc      7980
tactcatgct gacacattaa gatacaaatc ctggggccgt acagttattg ggacaactgt      8040 acccatcca ttagaaatgt tgggtccaca acatcgaaaa gagactcctt gtgcaccatg       8100
taacacatca gggttcaatt atgtttctgt gcattgtcca gacgggatcc atgacgtctt      8160
tagttcacgg ggaccattgc ctgcttatct agggtctaaa acatctgaat ctacatctat      8220
tttgcagcct tgggaaaggg aaagcaaagt cccactgatt aaaagagcta cacgtcttag      8280
agatgctatc tcttggtttg ttgaacccga ctctaaacta gcaatgacta ctttctaa       8340 catccactct ttaacaggcg aagaatggac caaaaggcag catgggttca aagaacagg       8400 gtctgccctt cataggtttt cgacatctcg gatgagccat ggtgggttcg catctcagag      8460
cactgcagca ttgaccaggt tgatggcaac tacagacacc atgagggatc tgggagatca      8520
gaatttcgac tttttattcc aagcaacgtt gctctatgct caaattacca ccactgttgc      8580
aagagacgga tggatcacca gttgtacaga tcattatcat attgcctgta agtcctgttt      8640
gagacccata gaagagatca ccctggactc aagtatggac tacacgcccc cagatgtatc      8700
ccatgtgctg aagacatgga ggaatgggga aggttcgtgg ggacaagaga taaaacagat      8760
ctatccttta gaagggaatt ggaagaattt agcacctgct gagcaatcct atcaagtcgg      8820
cagatgtata ggttttctat atggagactt ggcgtataga aaatctactc atgccgagga      8880
cagttctcta tttcctctat ctatacaagg tcgtattaga ggtcgaggtt cttaaaagg      8940 gttgctagac ggattaatga gagcaagttg ctgccaagta atacaccgga gaagtctggc      9000
tcatttgaag aggccggcca acgcagtgta cggaggtttg atttacttga ttgataaatt      9060
gagtgtatca cctccattcc tttctcttac tagatcagga cctattagag acgaattaga      9120
aacgattccc cacaagatcc caacctccta tccgacaagc aaccgtgata tggggggtgat      9180 tgtcagaaat tacttcaaat accaatgccg tctaattgaa aagggaaaat acagatcaca      9240
ttattcacaa ttatggttat tctcagatgt cttatccata gacttcattg gaccattctc      9300
tatttccacc accctcttgc aaatcctata caagccattt ttatctggga agataagaa       9360 tgagttgaga gagctggcaa atctttcttc attgctaaga tcaggagagg ggtgggaaga      9420
catacatgtg aaattcttca ccaaggacat attattgtgt ccagaggaaa tcagacatgc      9480
ttgcaagttc gggattgcta aggataataa taaagacatg agctatcccc cttggggaag      9540
ggaatccaga gggacaatta caacaatccc tgtttattat acgaccaccc cttacccaaa      9600
gatgctagag atgcctccaa gaatccaaaa tccctgctg tccggaatca ggttgggcca       9660
attaccaact ggcgctcatt ataaaattcg gagtatatta catggaatgg gaatccatta      9720
```

```
cagggacttc ttgagttgtg gagacggctc cggagggatg actgctgcat tactacgaga    9780
aaatgtgcat agcagaggaa tattcaatag tctgttagaa ttatcagggt cagtcatgcg    9840
aggcgcctct cctgagcccc ccagtgccct agaaacttta ggaggagata aatcgagatg    9900
tgtaaatggt gaaacatgtt gggaatatcc atctgactta tgtgacccaa ggacttggga    9960
ctatttcctc cgactcaaag caggcttggg gcttcaaatt gatttaattg taatggatat   10020
ggaagttcgg gattcttcta ctagcctgaa aattgagacg aatgttagaa attatgtgca   10080
ccggattttg gatgagcaag gagttttaat ctacaagact tatggaacat atatttgtga   10140
gagcgaaaag aatgcagtaa caatccttgg tcccatgttc aagacggtcg acttagttca   10200
aacagaattt agtagttctc aaacgtctga agtatatatg gtatgtaaag gtttgaagaa   10260
attaatcgat gaacccaatc ccgattggtc ttccatcaat gaatcctgga aaaacctgta   10320
cgcattccag tcatcagaac aggaatttgc cagagcaaag aaggttagta catactttac   10380
cttgacaggt attccctccc aattcattcc tgatccttt gtaaacattg agactatgct    10440
acaaatattc ggagtaccca cgggtgtgtc tcatgcggct gccttaaaat catctgatag   10500
acctgcagat ttattgacca ttagcctttt ttatatggcg attatatcgt attataacat   10560
caatcatatc agagtaggac cgataccct gaaccccca tcagatggaa ttgcacaaaa    10620
tgtggggatc gctataactg gtataagctt ttggctgagt ttgatggaga aagacattcc   10680
actatatcaa cagtgtttgg cagttatcca gcaatcattt ccgattaggt gggaggctat   10740
ttcagtaaaa ggaggataca agcagaagtg gagtactaga ggtgatgggc tcccaaaaga   10800
tacccgaatt tcagactcct tggccccaat cgggaactgg atcagatctt tggaattggt   10860
ccgaaaccaa gttcgtctaa atccattcaa taagatcttg ttcaatcagc tatgtcgtac   10920
agtggataat catttgaagt ggtcaaattt gcgaaaaaac acaggaatga ttgaatggat   10980
caatgggcga atttcaaaag aagaccggtc tatactgatg ttgaagagtg acctacatga   11040
ggaaaactct tggagagatt aaaaaatcag gaggagactc caaactttaa gtatgaaaaa   11100
aactttgatc cttaagaccc tcttgtggtt tttattttt tatctggttt tgtggtcttc    11160
gtgggtcggc atggcatctc cacctcctcg cggtccgacc tgggcatccg aaggaggacg   11220
tcgtccactc ggatggctaa gggagagctc ggatccggct gctaacaaag cccgaaagga   11280
agctgagttg gctgctgcca ccgctgagca ataactagca taaccccttg gggcctctaa   11340
acgggtcttg aggggttttt tgctgaaagg aggaactata tccggatcga gatcctctag   11400
agtcgacctg caggcatgca agcttgtatt ctatagtgtc acctaaatcg tatgtgtatg   11460
atacataagg ttatgtatta attgtagccg cgttctaacg acaatatgta caagcctaat   11520
tgtgtagcat ctggcttact gaagcagacc ctatcatctc tctcgtaaac tgccgtcaga   11580
gtcggtttgg ttggacgaac cttctgagtt tctggtaacg ccgtcccgca cccggaaatg   11640
gtcagcgaac caatcagcag ggtcatcgct agccagatcc tctacgccgg acgcatcgtg   11700
gccggcatca ccggcgccac aggtgcggtt gctggcgcct atatcgccga catcaccgat   11760
ggggaagatc gggctcgcca cttcgggctc atgagcgctt gtttcggcgt gggtatggtg   11820
gcaggccccg tggccggggg actgttgggc gccatctcct tgcaccattc cttgcggcgg   11880
cggtgctcaa cggcctcaac ctactactgg gctgcttcct aatgcaggag tcgcataagg   11940
gagagcgtcg aatggtgcac tctcagtaca atctgctctg atgccgcata gttaagccag   12000
ccccgacacc cgccaacacc cgctgacgcg ccctgacggg cttgtctgct cccggcatcc   12060
gcttacagac aagctgtgac cgtctccggg agctgcatgt gtcagaggtt ttcaccgtca   12120
```

```
tcaccgaaac gcgcgagacg aaagggcctc gtgatacgcc tattttttata ggttaatgtc   12180 atgataataa tggtttctta gacgtcaggt ggcactttc ggggaaatgt gcgcggaacc    12240
cctatttgtt tattttttcta aatacattca aatatgtatc cgctcatgag acaataaccc  12300
tgataaatgc ttcaataata ttgaaaaagg aagagtatga gtattcaaca tttccgtgtc   12360
gcccttattc cctttttgc ggcattttgc cttcctgttt ttgctcaccc agaaacgctg    12420
gtgaaagtaa aagatgctga agatcagttg ggtgcacgag tgggttacat cgaactggat   12480
ctcaacagcg gtaagatcct tgagagtttt cgccccgaag aacgttttcc aatgatgagc   12540
acttttaaag ttctgctatg tggcgcggta ttatcccgta ttgacgccgg caagagcaa    12600 ctcggtcgcc gcatacacta ttctcagaat gacttggttg agtactcacc agtcacagaa   12660
aagcatctta cggatggcat gacagtaaga gaattatgca gtgctgccat aaccatgagt   12720
gataacactg cggccaactt acttctgaca acgatcggag gaccgaagga gctaaccgct   12780 ttttttgcaca acatggggga tcatgtaact cgccttgatc gttgggaacc ggagctgaat   12840
gaagccatac caaacgacga gcgtgacacc acgatgcctg tagcaatggc aacaacgttg   12900
cgcaaactat taactggcga actacttact ctagcttccc ggcaacaatt aatagactgg   12960
atggaggcgg ataaagttgc aggaccactt ctgcgctcgg cccttccggc tggctggttt   13020
attgctgata atctggagc cggtgagcgt gggtctcgcg gtatcattgc agcactgggg    13080
ccagatggta agccctcccg tatcgtagtt atctacacga cggggagtca ggcaactatg   13140
gatgaacgaa atagacagat cgctgagata ggtgcctcac tgattaagca ttggtaactg   13200
tcagaccaag tttactcata tatactttag attgatttaa aacttcattt ttaatttaaa   13260
aggatctagg tgaagatcct tttgataat ctcatgacca aaatcccta acgtgagttt     13320 tcgttccact gagcgtcaga ccccgtagaa aagatcaaag gatcttcttg agatcctttt   13380
tttctgcgcg taatctgctg cttgcaaaca aaaaaaccac cgctaccagc ggtggtttgt   13440
ttgccggatc aagagctacc aactcttttt ccgaaggtaa ctggcttcag cagagcgcag   13500
ataccaaata ctgttcttct agtgtagccg tagttaggcc accacttcaa gaactctgta   13560
gcaccgccta catacctcgc tctgctaatc ctgttaccag tggctgctgc cagtggcgat   13620
aagtcgtgtc ttaccgggtt ggactcaaga cgatagttac cggataaggc gcagcggtcg   13680
ggctgaacgg ggggttcgtg cacacagccc agcttggagc gaacgaccta caccgaactg   13740
agatacctac agcgtgagct atgagaaagc gccacgcttc ccgaagggag aaaggcggac   13800
aggtatccgg taagcggcag ggtcggaaca ggagagcgca cgagggagct tccaggggga   13860
aacgcctggt atctttatag tcctgtcggg tttcgccacc tctgacttga gcgtcgattt   13920
ttgtgatgct cgtcaggggg gcggagccta tggaaaaacg ccagcaacgc ggcctttta    13980 cggttcctgg ccttttgctg gccttttgct cacatgttct ttcctgcgtt atccctgat   14040 tctgtggata accgtattac cgcctttgag tgagctgata ccgctcgccg cagccgaacg   14100
accgagcgca gcgagtcagt gagcgaggaa gcggaagagc gcccaatacg caaaccgcct   14160
ctccccgcgc gttggccgat tcattaatgc agggggatct cgatcccgcg aaattaatac   14220
gactcactat agg                                                      14233
```

<210> SEQ ID NO 16
<211> LENGTH: 14318
<212> TYPE: DNA
<213> ORGANISM: Artificial Sequence
<220> FEATURE:

<223> OTHER INFORMATION: Synthetic sequence

<400> SEQUENCE: 16

```
acgaagacaa acaaaccatt attatcatta aaaggctcag gagaaacttt aacagtaatc      60
aaaatgtctg ttacagtcaa gagaatcatt gacaacacag tcatagttcc aaaacttcct    120
gcaaatgagg atccagtgga atacccggca gattacttca gaaaatcaaa ggagattcct    180
ctttacatca atactacaaa aagtttgtca gatctaagag gatatgtcta ccaaggcctc    240
aaatccggaa atgtatcaat catacatgtc aacagctact tgtatggagc attaaaggac    300
atccggggta agttggataa agattggtca agtttcggaa taaacatcgg aaagcaggg    360
gatacaatcg gaatatttga ccttgtatcc ttgaaagccc tggacggcgt acttccagat    420
ggagtatcgg atgcttccag aaccagcgca gatgacaaat ggttgccttt gtatctactt    480
ggcttataca gagtgggcag aacacaaatg cctgaataca gaaaaaagct catggatggg    540
ctgacaaatc aatgcaaaat gatcaatgaa cagtttgaac ctcttgtgcc agaaggtcgt    600
gacattttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca aagattgtgc tgcattggca acatttggac acctctgcaa ataaccgga    780
atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata caaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gaccctataa ttctcagatc acctattata tattatgcta catatgaaaa   1380
aaactaacag atatcatgga taatctcaca aaagttcgtg agtatctcaa gtcctactct   1440
cgtctagatc aggcggtagg agagatagat gagatcgaag cacaacgagc tgaaaagtcc   1500
aattatgagt tgttccaaga ggacggagtg gaagagcata ctaggccctc ttatttttcag   1560
gcagcagatg attctgacac agaatctgaa ccagaaattg aagacaatca aggcttgtat   1620
gtaccagatc cggaagctga gcaagttgaa ggctttatac aggggccttt agatgactat   1680
gcagatgagg acgtggatgt tgtattcact tcggactgga acagcctga gcttgaatcc   1740
gacgagcatg gaaagacctt acggttgaca ttgccagagg gtttaagtgg agagcagaaa   1800
tcccagtggc ttttgacgat taaagcagtc gttcaaagtg ccaaacactg gaatctggca   1860
gagtgcacat ttgaagcatc gggagaaggg gtcatcataa aaaagcgcca gataactccg   1920
gatgtatata aggtcactcc agtgatgaac acacatccgt accaatcaga agccgtatca   1980
gatgtttggt ctctctcaaa gacatccatg actttccaac ccaagaaagc aagtcttcag   2040
cctctcacca tatccttgga tgaattgttc tcatctagag gagaattcat ctctgtcgga   2100
ggtaacggac gaatgtctca taagagggcc atcctgctcg gtctgaggta caaaaagttg   2160
tacaatcagg cgagagtcaa atattctctg tagactatga aaaaaagtaa cagatatcac   2220
aatctaagtg ttatcccaat ccattcatca tgagttcctt aaagaagatt ctcggtctga   2280
```

```
aggggaaagg taagaaatct aagaaattag ggatcgcacc acccccttat gaagaggaca    2340
ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga aacgtccctt ctacaaaatc ttggcttttt    2580
tgggttcttc taatctaaag gccactccag cggtattggc agatcaaggt caaccagagt    2640
atcacgctca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt cagagagaa ggccttaatg tttggcctga    2880
ttgtcgagaa aaaggcatct ggagcgtggg tcctggattc tatcagccac ttcaaatgag    2940
ctagtctagc ttccagcttc tgaacaatcc ccggtttact cagtctctcc taattccagc    3000
ctttcgaaca actaatatcc tgtcttttct atccctatga aaaaaactaa cagagatcga    3060
tctgtttcct tgacaccatg aagtgccttt tgtacttagc tttttttattc atcggggtga    3120 attgcaagtt caccatagtt tttccacaca accgaaaagg aaactggaaa aatgttcctt    3180
ccaattacca ttattgcccg tcaagctcag atttaaattg gcataatgac ttaataggca    3240
cagccttaca agtcaaaatg cccaagagtc acaaggctat tcaagcagac ggttggatgt    3300
gtcatgcttc caaatgggtc actacttgtg atttccgctg gtacggaccg gagtatataa    3360
cacattccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc tgaagcagcg attgtccagg tgactcctca ccatgtgctt gttgatgaat    3540
acacaggaga atgggttgat tcacagttca tcaacgaaaa atgcagcaat gacatatgcc    3600
ccactgtcca taactccaca acctggcatt ccgactataa ggtcaaaggg ctatgtgatt    3660
ctaacctcat ttccatggac atcacctttc tctcagagga cggagagcta tcatccctag    3720
gaaaggaggg cacagggttc agaagtaact actttgctta tgaaactgga gacaaggcct    3780
gcaaaatgca gtactgcaag cattgggag tcagactccc atcaggtgtc tggttcgaga    3840
tggctgataa ggatctcttt gctgcagcca gattccctga tgcccagaa gggtcaagta    3900 tctctgctcc atctcagacc tcagtggatg taagtctcat tcaggacgtt gagaggatct    3960
tggattattc cctctgccaa gaaacctgga gcaaaatcag agcgggtctt cccatctctc    4020
cagtggatct cagctatctt gctcctaaaa acccaggaac cggtcctgtc tttaccataa    4080
tcaatggtac cctaaaatac tttgagacca gatacatcag agtcgatatt gctgctccaa    4140
tcctctcaag aatggtcgga atgatcagtg aactaccac agaaagggaa ctgtgggatg    4200
actgggctcc atatgaagac gtggaaattg gacccaatgg agttctgagg accagttcag    4260
gatataagtt tccttatat atgattggac atggtatgtt ggactccgat cttcatctta    4320
gctcaaaggc tcaggtgttt gaacatcctc acattcaaga cgctgcttcg cagcttcctg    4380
atgatgagac tttatttttt ggtgatactg ggctatccaa aaatccaatc gagtttgtag    4440
aaggttggtt cagtagttgg aagagctcta ttgcctcttt ttgctttatc ataggttaa    4500 tcattggact attcttggtt ctccgagttg gtatttatct ttgcattaaa ttaaagcaca    4560
ccaagaaaag acagatttat acagacatag agatgaaccg acttggaaag taactcaaat    4620
```

```
cctgcacaac agattcttca tgtttgaacc aaatcaactt gtgatatcat gctcaaagag    4680
gccttaatta tattttaatt tttaattttt atgaaaaaaa ctaacagcaa tctcgagttt    4740
aaacccggga tccaccggtc gccaccagcg gccgcgactc tagaggatcc ccgggtatga    4800
aaaaactaac agcaatcatg gaagtccacg attttgagac cgacgagttc aatgatttca    4860
atgaagatga ctatgccaca agagaattcc tgaatcccga tgagcgcatg acgtacttga    4920
atcatgctga ttacaatttg aattctcctc taattagtga tgatattgac aatttgatca    4980
ggaaattcaa ttctcttccg attccctcga tgtgggatag taagaactgg gatggagttc    5040
ttgagatgtt aacatcatgt caagccaatc ccatctcaac atctcagatg cataaatgga    5100
tgggaagttg gttaatgtct gataatcatg atgccagtca agggtatagt ttttttacatg    5160
aagtggacaa agaggcagaa ataacatttg acgtggtgga gaccttcatc cgcggctggg    5220
gcaacaaacc aattgaatac atcaaaaagg aaagatggac tgactcattc aaaattctcg    5280
cttatttgtg tcaaaagttt ttggacttac acaagttgac attaatctta aatgctgtct    5340
ctgaggtgga attgctcaac ttggcgagga ctttcaaagg caaagtcaga agaagttctc    5400
atggaacgaa catatgcagg attagggttc ccagcttggg tcctactttt atttcagaag    5460
gatgggctta cttcaagaaa cttgatattc taatggaccg aaactttctg ttaatggtca    5520
aagatgtgat tatagggagg atgcaaacgg tgctatccat ggtatgtaga atagacaacc    5580
tgttctcaga gcaagacatc ttctcccttc taaatatcta cagaattgga gataaaattg    5640
tggagaggca gggaaatttt tcttatgact tgattaaaat ggtggaaccg atatgcaact    5700
tgaagctgat gaaattagca agagaatcaa ggcctttagt cccacaattc cctcattttg    5760
aaaatcatat caagacttct gttgatgaag gggcaaaaat tgaccgaggt ataagattcc    5820
tccatgatca gataatgagt gtgaaaacag tggatctcac actggtgatt tatgatcgt    5880
tcagacattg gggtcatcct tttatagatt attacactgg actagaaaaa ttacattccc    5940
aagtaaccat gaagaaagat attgatgtgt catatgcaaa agcacttgca agtgatttag    6000
ctcggattgt tctatttcaa cagttcaatg atcataaaaa gtggttcgtg aatggagact    6060
tgctccctca tgatcatccc tttaaaagtc atgttaaaga aaatacatgg cccacagctg    6120
ctcaagttca agattttgga gataaatggc atgaacttcc gctgattaaa tgttttgaaa    6180
tacccgactt actagaccca tcgataatat actctgacaa aagtcattca atgaataggt    6240
cagaggtgtt gaaacatgtc cgaatgaatc cgaacactcc tatccctagt aaaaaggtgt    6300
tgcagactat gttggacaca aaggctacca attggaaaga atttcttaaa gagattgatg    6360
agaagggctt agatgatgat gatctaatta ttggtcttaa aggaaggag agggaactga    6420
agttggcagg tagatttttc tccctaatgt cttggaaatt gcgagaatac tttgtaatta    6480
ccgaatattt gataaagact catttcgtcc ctatgtttaa aggcctgaca atggcggacg    6540
atctaactgc agtcattaaa aagatgttag attcctcatc cggccaagga ttgaagtcat    6600
atgaggcaat ttgcatagcc aatcacattg attacgaaaa atggaataac caccaaagga    6660
agttatcaaa cggcccagtg ttccgagtta tgggccagtt cttaggttat ccatccttaa    6720
tcgagagaac tcatgaattt tttgagaaaa gtcttatata ctacaatgga agaccagact    6780
tgatgcgtgt tcacaacaac acactgatca attcaacctc ccaacgagtt tgttggcaag    6840
gacaagaggg tggactggaa ggtctacggc aaaaaggatg gagtatcctc aatctactgg    6900
ttattcaaag agaggctaaa atcagaaaca ctgctgtcaa agtcttggca caaggtgata    6960
atcaagttat ttgcacacag tataaaacga agaaatcgag aaacgttgta gaattacagg    7020
```

```
gtgctctcaa tcaaatggtt tctaataatg agaaaattat gactgcaatc aaaatagggga    7080 cagggaagtt aggactttttg ataaatgacg atgagactat gcaatctgca gattacttga    7140
attatggaaa aataccgatt ttccgtggag tgattagagg gttagagacc aagagatggt    7200
cacgagtgac ttgtgtcacc aatgaccaaa tacccacttg tgctaatata atgagctcag    7260
tttccacaaa tgctctcacc gtagctcatt ttgctgagaa cccaatcaat gccatgatac    7320
agtacaatta ttttgggaca tttgctagac tcttgttgat gatgcatgat cctgctcttc    7380
gtcaatcatt gtatgaagtt caagataaga taccgggctt gcacagttct actttcaaat    7440
acgccatgtt gtatttggac ccttccattg gaggagtgtc gggcatgtct ttgtccaggt    7500 tttttgattag agccttccca gatcccgtaa cagaaagtct ctcattctgg agattcatcc    7560
atgtacatgc tcgaagtgag catctgaagg agatgagtgc agtatttgga aaccccgaga    7620
tagccaagtt tcgaataact cacatagaca agctagtaga agatccaacc tctctgaaca    7680
tcgctatggg aatgagtcca gcgaacttgt taaagactga ggttaaaaaa tgcttaatcg    7740
aatcaagaca aaccatcagg aaccaggtga ttaaggatgc aaccatatat ttgtatcatg    7800
aagaggatcg gctcagaagt ttcttatggt caataaatcc tctgttccct agatttttaa    7860
gtgaattcaa atcaggcact tttttgggag tcgcagacgg gctcatcagt ctatttcaaa    7920
attctcgtac tattcggaac tcctttaaga aaaagtatca tagggaattg gatgatttga    7980
ttgtgaggag tgaggtatcc tctttgacac atttagggaa acttcatttg agaaggggat    8040
catgtaaaat gtggacatgt tcagctactc atgctgacac attaagatac aaatcctggg    8100
gccgtacagt tattgggaca actgtacccc atccattaga aatgttgggt ccacaacatc    8160
gaaaagagac tccttgtgca ccatgtaaca catcagggtt caattatgtt tctgtgcatt    8220
gtccagacgg gatccatgac gtctttagtt cacggggacc attgcctgct tatctagggt    8280
ctaaaacatc tgaatctaca tctatttttgc agccttggga aagggaaagc aaagtcccac    8340
tgattaaaag agctacacgt cttagagatg ctatctcttg gtttgttgaa cccgactcta    8400
aactagcaat gactatactt tctaacatcc actctttaac aggcgaagaa tggaccaaaa    8460
ggcagcatgg gttcaaaaga acagggtctg cccttcatag gttttcgaca tctcggatga    8520
gccatggtgg gttcgcatct cagagcactg cagcattgac caggttgatg gcaactacag    8580
acaccatgag ggatctggga gatcagaatt tcgactttttt attccaagca acgttgctct    8640
atgctcaaat taccaccact gttgcaagag acggatggat caccagttgt acagatcatt    8700
atcatattgc ctgtaagtcc tgtttgagac ccatagaaga gatcaccctg gactcaagta    8760
tggactacac gccccagat gtatcccatg tgctgaagac atggaggaat ggggaaggtt    8820
cgtggggaca agagataaaa cagatctatc ctttagaagg gaattggaag aatttagcac    8880
ctgctgagca atcctatcaa gtcggcagat gtataggttt tctatatgga gacttggcgt    8940
atagaaaatc tactcatgcc gaggacagtt ctctatttcc tctatctata caaggtcgta    9000
ttagaggtcg aggtttctta aaagggttgc tagacggatt aatgagagca agttgctgcc    9060
aagtaataca ccggagaagt ctggctcatt tgaagaggcc ggccaacgca gtgtacggag    9120 gtttgatttta cttgattgat aaattgagtg tatcacctcc attcctttct cttactagat    9180
caggacctat tagagacgaa ttagaaacga ttccccacaa gatcccaacc tcctatccga    9240
caagcaaccg tgtatggggg gtgattgtca gaaattactt caaataccaa tgccgtctaa    9300
ttgaaaaggg aaaatacaga tcacattatt cacaattatg gttattctca gatgtcttat    9360
```

```
ccatagactt cattggacca ttctctattt ccaccaccct cttgcaaatc ctatacaagc    9420
cattttatc  tgggaaagat aagaatgagt tgagagagct ggcaaatctt tcttcattgc    9480
taagatcagg agagggtgg  gaagacatac atgtgaaatt cttcaccaag  acatattat    9540
tgtgtccaga ggaaatcaga catgcttgca agttcgggat tgctaaggat aataataaag    9600
acatgagcta tcccccttgg ggaagggaat ccagagggac aattacaaca atccctgttt    9660
attatacgac cacccCttac ccaaagatgc tagagatgcc tccaagaatc caaaatcccc    9720
tgctgtccgg aatcaggttg ggccaattac caactggcgc tcattataaa attcggagta    9780
tattacatgg aatgggaatc cattacaggg acttcttgag ttgtggagac ggctccggag    9840
ggatgactgc tgcattacta cgagaaaatg tgcatagcag aggaatattc aatagtctgt    9900
tagaattatc agggtcagtc atgcgaggcg cctctcctga gccccccagt gccctagaaa    9960
ctttaggagg agataaatcg agatgtgtaa atggtgaaac atgttgggaa tatccatctg   10020
acttatgtga cccaaggact tgggactatt cctccgact  caaagcaggc ttggggcttc   10080
aaattgattt aattgtaatg gatatggaag ttcgggattc ttctactagc ctgaaaattg   10140
agacgaatgt tagaaattat gtgcaccgga ttttggatga gcaaggagtt ttaatctaca   10200
agacttatgg aacatatatt tgtgagagcg aaaagaatgc agtaacaatc cttggtccca   10260
tgttcaagac ggtcgactta gttcaaacag aatttagtag ttctcaaacg tctgaagtat   10320
atatggtatg taaaggtttg aagaaattaa tcgatgaacc caatcccgat tggtcttcca   10380
tcaatgaatc ctggaaaaac ctgtacgcat tccagtcatc agaacaggaa tttgccagag   10440
caaagaaggt tagtacatac tttaccttga caggtattcc ctcccaattc attcctgatc   10500
cttttgtaaa cattgagact atgctacaaa tattcggagt acccacgggt gtgtctcatg   10560
cggctgcctt aaaatcatct gatagacctg cagatttatt gaccattagc cttttttata   10620
tggcgattat atcgtattat aacatcaatc atatcagagt aggaccgata cctccgaacc   10680
ccccatcaga tggaattgca caaaatgtgg ggatcgctat aactggtata agcttttggc   10740
tgagtttgat ggagaaagac attccactat atcaacagtg tttggcagtt atccagcaat   10800
catttccgat taggtgggag gctatttcag taaaaggagg atacaagcag aagtggagta   10860
ctagaggtga tgggctccca aaagataccc gaatttcaga ctccttggcc ccaatcggga   10920
actggatcag atctttggaa ttggtccgaa accaagttcg tctaaatcca ttcaataaga   10980
tcttgttcaa tcagctatgt cgtacagtgg ataatcattt gaagtggtca aatttgcgaa   11040
aaaacacagg aatgattgaa tggatcaatg ggcgaatttc aaaagaagac cggtctatac   11100
tgatgttgaa gagtgaccta catgaggaaa actcttggag agattaaaaa atcaggagga   11160
gactccaaac tttaagtatg aaaaaaactt tgatccttaa gaccctcttg tggttttat    11220
ttttttatct ggttttgtgg tcttcgtggg tcggcatggc atctccacct cctcgcggtc   11280
cgacctgggc atccgaagga ggacgtcgtc cactcgatg  gctaagggag agctcggatc   11340
cggctgctaa caaagcccga aaggaagctg agttggctgc tgccaccgct gagcaataac   11400
tagcataacc ccttggggcc tctaaacggg tcttgagggg ttttttgctg aaaggaggaa   11460
ctatatccgg atcgagatcc tctagagtcg acctgcaggc atgcaagctt gtattctata   11520
gtgtcaccta atcgtatgt  gtatgataca taaggttatg tattaattgt agccgcgttc   11580
taacgacaat atgtacaagc ctaattgtgt agcatctggc ttactgaagc agacccttatc   11640
atctctctcg taaactgccg tcagagtcgg tttggttgga cgaaccttct gagtttctgg   11700
taacgccgtc ccgcacccgg aaatggtcag cgaaccaatc agcagggtca tcgctagcca   11760
```

```
gatcctctac gccggacgca tcgtggccgg catcaccggc gccacaggtg cggttgctgg    11820
cgcctatatc gccgacatca ccgatgggga agatcgggct cgccacttcg ggctcatgag    11880
cgcttgtttc ggcgtgggta tggtggcagg ccccgtggcc gggggactgt tgggcgccat    11940
ctccttgcac cattccttgc ggcggcggtg ctcaacggcc tcaacctact actgggctgc    12000
ttcctaatgc aggagtcgca taagggagag cgtcgaatgg tgcactctca gtacaatctg    12060
ctctgatgcc gcatagttaa gccagccccg acacccgcca acacccgctg acgcgccctg    12120
acgggcttgt ctgctcccgg catccgctta cagacaagct gtgaccgtct ccgggagctg    12180
catgtgtcag aggttttcac cgtcatcacc gaaacgcgcg agacgaaagg gcctcgtgat    12240
acgcctattt ttataggtta atgtcatgat aataatggtt tcttagacgt caggtggcac    12300
ttttcgggga aatgtgcgcg gaacccctat ttgtttattt ttctaaatac attcaaatat    12360
gtatccgctc atgagacaat aaccctgata aatgcttcaa taatattgaa aaggaagag    12420 tatgagtatt caacatttcc gtgtcgccct tattccctttt tttgcggcat tttgccttcc    12480 tgttttgct cacccagaaa cgctggtgaa agtaaaagat gctgaagatc agttgggtgc    12540
acgagtgggt tacatcgaac tggatctcaa cagcggtaag atccttgaga gttttcgccc    12600
cgaagaacgt tttccaatga tgagcacttt taaagttctg ctatgtggcg cggtattatc    12660
ccgtattgac gccgggcaag agcaactcgg tcgccgcata cactattctc agaatgactt    12720
ggttgagtac tcaccagtca cagaaaagca tcttacggat ggcatgacag taagagaatt    12780
atgcagtgct gccataacca tgagtgataa cactgcggcc aacttacttc tgacaacgat    12840
cggaggaccg aaggagctaa ccgcttttt gcacaacatg ggggatcatg taactcgcct    12900
tgatcgttgg gaaccggagc tgaatgaagc cataccaaac gacgagcgtg acaccacgat    12960
gcctgtagca atggcaacaa cgttgcgcaa actattaact ggcgaactac ttactctagc    13020
ttcccggcaa caattaatag actggatgga ggcggataaa gttgcaggac cacttctgcg    13080
ctcggccctt ccggctggct ggtttattgc tgataaatct ggagccggtg agcgtgggtc    13140
tcgcggtatc attgcagcac tggggccaga tggtaagccc tcccgtatcg tagttatcta    13200
cacgacgggg agtcaggcaa ctatggatga acgaaataga cagatcgctg agataggtgc    13260
ctcactgatt aagcattggt aactgtcaga ccaagtttac tcatatatac tttagattga    13320
tttaaaactt catttttaat ttaaaaggat ctaggtgaag atcctttttg ataatctcat    13380
gaccaaaatc ccttaacgtg agttttcgtt ccactgagcg tcagaccccg tagaaaagat    13440
caaaggatct tcttgagatc cttttttttct gcgcgtaatc tgctgcttgc aaacaaaaaa    13500
accaccgcta ccagcggtgg tttgtttgcc ggatcaagag ctaccaactc ttttccgaa    13560 ggtaactggc ttcagcagag cgcagatacc aaatactgtt cttctagtgt agccgtagtt    13620
aggccaccac ttcaagaact ctgtagcacc gcctacatac ctcgctctgc taatcctgtt    13680
accagtggct gctgccagtg gcgataagtc gtgtcttacc gggttggact caagacgata    13740
gttaccggat aaggcgcagc ggtcgggctg aacggggggt tcgtgcacac agcccagctt    13800
ggagcgaacg acctacaccg aactgagata cctacagcgt gagctatgag aaagcgccac    13860
gcttcccgaa gggagaaagg cggacaggta tccggtaagc ggcagggtcg gaacaggaga    13920
gcgcacgagg gagcttccag gggaaacgc ctggtatctt tatagtcctg tcgggtttcg    13980
ccacctctga cttgagcgtc gatttttgtg atgctcgtca gggggggcgga gcctatggaa    14040 aaacgccagc aacgcggcct ttttacggtt cctggccttt tgctggcctt tgctcacat    14100
```

```
gttctttcct gcgttatccc ctgattctgt ggataaccgt attaccgcct ttgagtgagc   14160
tgataccgct cgccgcagcc gaacgaccga gcgcagcgag tcagtgagcg aggaagcgga   14220
agagcgccca atacgcaaac cgcctctccc cgcgcgttgg ccgattcatt aatgcagggg   14280
gatctcgatc ccgcgaaatt aatacgactc actatagg                          14318
```

<210> SEQ ID NO 17
<211> LENGTH: 6330
<212> TYPE: DNA
<213> ORGANISM: Artificial Sequence
<220> FEATURE:
<223> OTHER INFORMATION: Synthetic sequence

<400> SEQUENCE: 17

```
atggaagtcc acgattttga gaccgacgag ttcaatgatt tcaatgaaga tgactatgcc     60
acaagagaat tcctgaatcc cgatgagcgc atgacgtact tgaatcatgc tgattacaat    120
ttgaattctc ctctaattag tgatgatatt gacaatttga tcaggaaatt caattctctt    180
ccgattccct cgatgtggga tagtaagaac tgggatggag ttcttgagat gttaacatca    240
tgtcaagcca atcccatctc aacatctcag atgcataaat ggatgggaag ttggttaatg    300
tctgataatc atgatgccag tcaagggtat agttttttac atgaagtgga caaagaggca    360
gaaataacat tgacgtggt ggagaccttc atccgcggct ggggcaacaa accaattgaa     420
tacatcaaaa aggaaagatg gactgactca ttcaaaattc tcgcttattt gtgtcaaaag    480
tttttggact tacacaagtt gacattaatc ttaaatgctg tctctgaggt ggaattgctc    540
aacttggcga ggactttcaa aggcaaagtc agaagaagtt ctcatggaac gaacatatgc    600
aggattaggg ttcccagctt gggtcctact tttatttcag aaggatgggc ttacttcaag    660
aaacttgata ttctaatgga ccgaaacttt ctgttaatgg tcaaagatgt gattataggg    720
aggatgcaaa cggtgctatc catggtatgt agaatagaca acctgttctc agagcaagac    780
atcttctccc ttctaaatat ctacagaatt ggagataaaa ttgtggagag cagggaaat    840 tttcttatg acttgattaa aatggtggaa ccgatatgca acttgaagct gatgaaatta    900
gcaagagaat caaggccttt agtcccacaa ttccctcatt ttgaaaatca tatcaagact    960
tctgttgatg aaggggcaaa aattgaccga ggtataagat tcctccatga tcagataatg   1020
agtgtgaaaa cagtggatct cacactggtg atttatggat cgttcagaca ttggggtcat   1080 cctttttatag attattacac tggactagaa aaattacatt cccaagtaac catgaagaaa   1140
gatattgatg tgtcatatgc aaaagcactt gcaagtgatt tagctcggat tgttctattt   1200
caacagttca atgatcataa aaagtggttc gtgaatggag acttgctccc tcatgatcat   1260 cccttaaaa gtcatgttaa agaaaataca tggcccacag ctgctcaagt tcaagatttt   1320
ggagataaat ggcatgaact tccgctgatt aaatgttttg aaatacccga cttactagac   1380
ccatcgataa tatactctga caaaagtcat tcaatgaata ggtcagaggt gttgaaacat   1440
gtccgaatga atccgaacac tcctatccct agtaaaaagg tgttgcagac tatgttggac   1500
acaaaggcta ccaattggaa agaatttctt aaagagattg atgagaaggg cttagatgat   1560
gatgatctaa ttattggtct taaggaaag gagagggaac tgaagttggc aggtagattt   1620
ttctccctaa tgtcttggaa attgcgagaa tactttgtaa ttaccgaata tttgataaag   1680
actcatttcg tccctatgtt taaggcctg acaatggcgg acgatctaac tgcagtcatt   1740
aaaaagatgt tagattcctc atccggccaa ggattgaagt catatgaggc aatttgcata   1800
gccaatcaca ttgattacga aaatggaat aaccaccaaa ggaagttatc aaacggccca   1860
```

```
gtgttccgag ttatgggcca gttcttaggt tatccatcct taatcgagag aactcatgaa    1920
ttttttgaga aaagtcttat atactacaat ggaagaccag acttgatgcg tgttcacaac    1980
aacacactga tcaattcaac ctcccaacga gtttgttggc aaggacaaga gggtggactg    2040
gaaggtctac ggcaaaaagg atggagtatc ctcaatctac tggttattca aagagaggct    2100
aaaatcagaa acactgctgt caaagtcttg gcacaaggtg ataatcaagt tatttgcaca    2160
cagtataaaa cgaagaaatc gagaaacgtt gtagaattac agggtgctct caatcaaatg    2220
gtttctaata atgagaaaat tatgactgca atcaaaatag gacagggaa gttaggactt     2280 ttgataaatg acgatgagac tatgcaatct gcagattact tgaattatgg aaaaataccg    2340
attttccgtg gagtgattag agggttagag accaagagat ggtcacgagt gacttgtgtc    2400
accaatgacc aaatacccac ttgtgctaat ataatgagct cagtttccac aaatgctctc    2460
accgtagctc attttgctga gaacccaatc aatgccatga tacagtacaa ttattttggg    2520
acatttgcta gactcttgtt gatgatgcat gatcctgctc ttcgtcaatc attgtatgaa    2580
gttcaagata agataccggg cttgcacagt tctactttca aatacgccat gttgtatttg    2640
gacccttcca ttggaggagt gtcgggcatg tctttgtcca ggttttttgat tagagccttc    2700 ccagatcccg taacagaaag tctctcattc tggagattca tccatgtaca tgctcgaagt    2760
gagcatctga aggagatgag tgcagtattt ggaaaccccg agatagccaa gtttcgaata    2820
actcacatag acaagctagt agaagatcca acctctctga acatcgctat gggaatgagt    2880
ccagcgaact tgttaaagac tgaggttaaa aaatgcttaa tcgaatcaag acaaaccatc    2940
aggaaccagg tgattaagga tgcaaccata tatttgtatc atgaagagga tcggctcaga    3000
agtttcttat ggtcaataaa tcctctgttc cctagatttt taagtgaatt caaatcaggc    3060
acttttttgg gagtcgcaga cgggctcatc agtctatttc aaaattctcg tactattcgg    3120 aactcccttta agaaaagta tcataggaa ttggatgatt tgattgtgag gagtgaggta    3180
tcctctttga cacatttagg gaaacttcat ttgagaaggg gatcatgtaa aatgtggaca    3240
tgttcagcta ctcatgctga cacattaaga tacaaatcct ggggccgtac agttattggg    3300
acaactgtac cccatccatt agaaatgttg ggtccacaac atcgaaaaga gactccttgt    3360
gcaccatgta acacatcagg gttcaattat gtttctgtgc attgtccaga cgggatccat    3420
gacgtcttta gttcacgggg accattgcct gcttatctag ggtctaaaac atctgaatct    3480
acatctattt tgcagccttg ggaaagggaa agcaaagtcc cactgattaa agagctaca    3540 cgtcttagag atgctatctc ttggtttgtt gaacccgact ctaaactagc aatgactata    3600 cttctaaca tccactcttt aacaggcgaa gaatggacca aaaggcagca tgggttcaaa    3660
agaacagggt ctgcccttca taggttttcg acatctcgga tgagccatgg tgggttcgca    3720
tctcagagca ctgcagcatt gaccaggttg atggcaacta cagacaccat gagggatctg    3780
ggagatcaga atttcgactt tttattccaa gcaacgttgc tctatgctca aattaccacc    3840
actgttgcaa gagacggatg gatcaccagt tgtacagatc attatcatat tgcctgtaag    3900
tcctgtttga gacccataga agagatcacc ctggactcaa gtatggacta cacgccccca    3960
gatgtatccc atgtgctgaa gacatggagg aatggggaag gttcgtgggg acaagagata    4020
aaacagatct atcctttaga agggaattgg aagaatttag cacctgctga gcaatcctat    4080
caagtcggca gatgtataag gttttctatat ggagacttgg cgtatagaaa atctactcat    4140
gccgaggaca gttctctatt tcctctatct atacaaggtc gtattagagg tcgaggtttc    4200
```

```
ttaaaagggt tgctagacgg attaatgaga gcaagttgct gccaagtaat acaccggaga    4260
agtctggctc atttgaagag gccggccaac gcagtgtacg gaggtttgat ttacttgatt    4320
gataaattga gtgtatcacc tccattcctt tctcttacta gatcaggacc tattagagac    4380
gaattagaaa cgattcccca caagatccca acctcctatc cgacaagcaa ccgtgatatg    4440
ggggtgattg tcagaaatta cttcaaatac caatgccgtc taattgaaaa gggaaaatac    4500
agatcacatt attcacaatt atggttattc tcagatgtct tatccataga cttcattgga    4560
ccattctcta tttccaccac cctcttgcaa atcctataca agccattttt atctgggaaa    4620
gataagaatg agttgagaga gctggcaaat cttcttcat tgctaagatc aggagagggg     4680
tgggaagaca tacatgtgaa attcttcacc aaggacatat tattgtgtcc agaggaaatc    4740
agacatgctt gcaagttcgg gattgctaag gataataata aagacatgag ctatcccct    4800 tggggaaggg aatccagagg gacaattaca acaatccctg tttattatac gaccacccct    4860
tacccaaaga tgctagagat gcctccaaga atccaaaatc ccctgctgtc cggaatcagg    4920
ttgggccaat taccaactgg cgctcattat aaaattcgga gtatattaca tggaatggga    4980
atccattaca gggacttctt gagttgtgga gacggctccg gagggatgac tgctgcatta    5040
ctacgagaaa atgtgcatag cagaggaata ttcaatagtc tgttagaatt atcagggtca    5100
gtcatgcgag gcgcctctcc tgagcccccc agtgccctag aaactttagg aggagataaa    5160
tcgagatgtg taaatggtga acatgttgg gaatatccat ctgacttatg tgacccaagg     5220
acttgggact atttcctccg actcaaagca ggcttggggc ttcaaattga tttaattgta    5280
atggatatgg aagttcggga ttcttctact agcctgaaaa ttgagacgaa tgttagaaat    5340
tatgtgcacc ggattttgga tgagcaagga gttttaatct acaagactta tggaacatat    5400
atttgtgaga gcgaaaagaa tgcagtaaca atccttggtc ccatgttcaa gacggtcgac    5460
ttagttcaaa cagaatttag tagttctcaa acgtctgaag tatatatggt atgtaaaggt    5520
ttgaagaaat taatcgatga acccaatccc gattggtctt ccatcaatga atcctggaaa    5580
aacctgtacg cattccagtc atcagaacag gaatttgcca gagcaaagaa ggttagtaca    5640
tactttacct tgacaggtat tccctcccaa ttcattcctg atccttttgt aaacattgag    5700
actatgctac aaatattcgg agtacccacg ggtgtgtctc atgcggctgc cttaaaatca    5760
tctgatagac ctgcagattt attgaccatt agccttttt atatggcgat tatatcgtat    5820
tataacatca atcatatcag agtaggaccg atacctccga accccccatc agatggaatt    5880
gcacaaaatg tggggatcgc tataactggt ataagctttt ggctgagttt gatggagaaa    5940
gacattccac tatatcaaca gtgtttggca gttatccagc aatcatttcc gattaggtgg    6000
gaggctattt cagtaaaagg aggatacaag cagaagtgga gtactagagg tgatgggctc    6060
ccaaaagata cccgaatttc agactccttg gccccaatcg ggaactggat cagatctttg    6120
gaattggtcc gaaaccaagt tcgtctaaat ccattcaata agatcttgtt caatcagcta    6180
tgtcgtacag tggataatca tttgaagtgg tcaaatttgc gaaaaaacac aggaatgatt    6240
gaatggatca atgggcgaat ttcaaaagaa gaccggtcta tactgatgtt gaagagtgac    6300
ctacatgagg aaaactcttg gagagattaa                                    6330
```

<210> SEQ ID NO 18
<211> LENGTH: 6330
<212> TYPE: DNA
<213> ORGANISM: Artificial Sequence
<220> FEATURE:
<223> OTHER INFORMATION: Synthetic sequence

<400> SEQUENCE: 18

```
atggaagtcc acgattttga gaccgacgag ttcaatgatt tcaatgaaga tgactatgcc    60
acaagagaat tcctgaatcc cgatgagcgc atgacgtact tgaatcatgc tgattacaat   120
ttgaattctc ctctaattag tgatgatatt gacaatttga tcaggaaatt caattctctt   180
ccgattccct cgatgtggga tagtaagaac tgggatggag ttcttgagat gttaacatca   240
tgtcaagcca atcccatctc aacatctcag atgcataaat ggatgggaag ttggttaatg   300
tctgataatc atgatgccag tcaagggtat agttttttac atgaagtgga caaagaggca   360
gaaataacat ttgacgtggt ggagaccttc atccgcggct ggggcaacaa accaattgaa   420
tacatcaaaa aggaaagatg gactgactca ttcaaaattc tcgcttattt gtgtcaaaag   480
ttttggact tacacaagtt gacattaatc ttaaatgctg tctctgaggt ggaattgctc   540
aacttggcga ggactttcaa aggcaaagtc agaagaagtt ctcatggaac gaacatatgc   600
aggattaggg ttcccagctt gggtcctact tttatttcag aaggatgggc ttacttcaag   660
aaacttgata ttctaatgga ccgaaacttt ctgttaatgg tcaaagatgt gattataggg   720
aggatgcaaa cggtgctatc catggtatgt agaatagaca acctgttctc agagcaagac   780
atcttctccc ttctaaatat ctacagaatt ggagataaaa ttgtggagag cagggaaat   840
ttttcttatg acttgattaa aatggtggaa ccgatatgca acttgaagct gatgaaatta   900
gcaagagaat caaggccttt agtcccacaa ttccctcatt ttgaaaatca tatcaagact   960
tctgttgatg aaggggcaaa aattgaccga ggtataagat tcctccatga tcagataatg  1020
agtgtgaaaa cagtggatct cacactggtg atttatggat cgttcagaca ttggggtcat  1080
ccttttatag attattacac tggactagaa aaattacatt cccaagtaac catgaagaaa  1140
gatattgatg tgtcatatgc aaaagcactt gcaagtgatt tagctcggat tgttctattt  1200
caacagttca atgatcataa aaagtggttc gtgaatggag acttgctccc tcatgatcat  1260
cccttaaaa gtcatgttaa agaaaataca tggcccacag ctgctcaagt tcaagatttt  1320
ggagataaat ggcatgaact tccgctgatt aaatgttttg aaatacccga cttactagac  1380
ccatcgataa tatactctga caaaagtcat tcaatgaata ggtcagaggt gttgaaacat  1440
gtccgaatga atccgaacac tcctatccct agtaaaaagg tgttgcagac tatgttggac  1500
acaaaggcta ccaattggaa agaatttctt aaagagattg atgagaaggg cttagatgat  1560
gatgatctaa ttattggtct taaaggaaag gagagggaac tgaagttggc aggtagattt  1620
ttctccctaa tgtcttggaa attgcgagaa tactttgtaa ttaccgaata tttgataaag  1680
actcatttcg tccctatgtt taaaggcctg acaatggcgg acgatctaac tgcagtcatt  1740
aaaaagatgt tagattcctc atccggccaa ggattgaagt catatgaggc aatttgcata  1800
gccaatcaca ttgattacga aaatggaat aaccaccaaa ggaagttatc aaacggccca  1860
gtgttccgag ttatgggcca gttcttaggt tatccatcct taatcgagag aactcatgaa  1920
ttttttgaga aagtcttat atactacaat ggaagaccag acttgatgcg tgttcacaac  1980
aacacactga tcaattcaac ctcccaacga gtttgttggc aaggacaaga gggtggactg  2040
gaaggtctac ggcaaaaagg atggagtatc ctcaatctac tggttattca agagaggct   2100
aaaatcagaa acactgctgt caaagtcttg gcacaaggtg ataatcaagt tatttgcaca  2160
cagtataaaa cgaagaaatc gagaaacgtt gtagaattac agggtgctct caatcaaatg  2220
gtttctaata atgagaaaat tatgactgca atcaaaatag gacagggaa gttaggactt  2280
```

-continued

```
ttgataaatg acgatgagac tatgcaatct gcagattact tgaattatgg aaaaataccg     2340
attttccgtg gagtgattag agggttagag accaagagat ggtcacgagt gacttgtgtc     2400
accaatgacc aaatacccac ttgtgctaat ataatgagct cagtttccac aaatgctctc     2460
accgtagctc attttgctga gaacccaatc aatgccatga tacagtacaa ttattttggg     2520
acatttgcta gactcttgtt gatgatgcat gatcctgctc ttcgtcaatc attgtatgaa     2580
gttcaagata agataccggg cttgcacagt tctactttca aatacgccat gttgtatttg     2640
gacccttcca ttggaggagt gtcgggcatg tctttgtcca ggttttttgat tagagccttc    2700 ccagatcccg taacagaaag tctctcattc tggagattca tccatgtaca tgctcgaagt     2760
gagcatctga aggagatgag tgcagtattt ggaaaccccg atagccaa gtttcgaata      2820 actcacatag acaagctagt agaagatcca acctctctga acatcgctat gggaatgagt    2880
ccagcgaact tgttaaagac tgaggttaaa aaatgcttaa tcgaatcaag acaaaccatc    2940
aggaaccagg tgattaagga tgcaaccata tatttgtatc atgaagagga tcggctcaga    3000
agtttcttat ggtcaataaa tcctctgttc cctagatttt taagtgaatt caaatcaggc    3060 actttttttgg gagtcgcaga cgggctcatc agtctatttc aaaattctcg tactattcgg   3120
aactccttta agaaaagta tcataggaa ttggatgatt tgattgtgag gagtgaggta     3180
tcctctttga cacatttagg gaaacttcat ttgagaaggg gatcatgtaa aatgtggaca    3240
tgttcagcta ctcatgctga cacattaaga tacaaatcct ggggccgtac agttattggg    3300
acaactgtac cccatccatt agaaatgttg ggtccacaac atcgaaaaga gactccttgt    3360
gcaccatgta acacatcagg gttcaattat gtttctgtgc attgtccaga cgggatccat    3420 gacgtctttta gttcacgggg accattgcct gcttatctag ggtctaaaac atctgaatct   3480
acatctattt tgcagccttg ggaaagggaa agcaaagtcc cactgattaa aagagctaca    3540
cgtcttagag atgctatctc ttggtttgtt gaacccgact ctaaactagc aatgactata   3600 cttttctaaca tccactcttt aacaggcgaa gaatggacca aaaggcagca tgggttcaaa   3660
agaacagggt ctgcccttca taggttttcg acatctcgga tgagccatgg tgggttcgca   3720
tctcagagca ctgcagcatt gaccaggttg atggcaacta cagacaccat gagggatctg    3780
ggagatcaga atttcgactt tttattccaa gcaacgttgc tctatgctca aattaccacc    3840
actgttgcaa gagacggatg gatcaccagt tgtacagatc attatcatat tgcctgtaag    3900
tcctgtttga gacccataga agagatcacc ctggactcaa gtatggacta cacgccccca    3960
gatgtatccc atgtgctgaa gacatggagg aatgggaag gttcgtgggg acaagagata    4020
aaacagatct atcctttaga agggaattgg aagaatttag cacctgctga gcaatcctat   4080
caagtcggca gatgtatagg ttttctatat ggagacttgg cgtatagaaa atctactcat    4140
gccgaggaca gttctctatt tcctctatct atacaaggtc gtattagagg tcgaggtttc   4200 ttaaagggt tgctagacgg attaatgaga gcaagttgct gccaagtaat acaccggaga    4260
agtctggctc atttgaagag gccggccaac gcagtgtacg gaggtttgat ttacttgatt   4320
gataaattga gtgtatcacc tccattcctt tctcttacta gatcaggacc tattagagac    4380
gaattagaaa cgattcccca caagatccca acctcctatc cgacaagcaa ccgtgatatg    4440
ggggtgattg tcagaaatta cttcaaatac caatgccgtc taattgaaaa gggaaaatac    4500
agatcacatt attcacaatt atggttattc tcagatgtct tatccataga cttcattgga    4560
ccattctcta tttccaccac cctccttgca atccctataca agccatttttt atctgggaaa   4620 gataagaatg agttgagaga gctggcaaat cttttcttcat tgctaagatc aggagagggg    4680
```

```
tgggaagaca tacatgtgaa attcttcacc aaggacatat tattgtgtcc agaggaaatc    4740
agacatgctt gcaagttcgg gattgctaag gataataata aagacatgag ctatccccct    4800
tggggaaggg aatccagagg gacaattaca acaatccctg tttattatac gaccacccct    4860
tacccaaaga tgctagagat gcctccaaga atccaaaatc ccctgctgtc cggaatcagg    4920
ttgggccaat taccaactgg cgctcattat aaaattcgga gtatattaca tggaatggga    4980
atccattaca gggacttctt gagttgtgga cacggctccg gagggatgac tgctgcatta    5040
ctacgagaaa atgtgcatag cagaggaata ttcaatagtc tgttagaatt atcagggtca    5100
gtcatgcgag gcgcctctcc tgagcccccc agtgccctag aaactttagg aggagataaa    5160
tcgagatgtg taaatggtga acatgttggg aatatccat ctgacttatg tgacccaagg     5220
acttgggact atttcctccg actcaaagca ggcttggggc ttcaaattga tttaattgta    5280
atggatatgg aagttcggga ttcttctact agcctgaaaa ttgagacgaa tgttagaaat    5340
tatgtgcacc ggatttttga tgagcaagga gttttaatct acaagactta tggaacatat    5400
atttgtgaga gcgaaaagaa tgcagtaaca atccttggtc ccatgttcaa gacggtcgac    5460
ttagttcaaa cagaatttag tagttctcaa acgtctgaag tatatatggt atgtaaaggt    5520
ttgaagaaat taatcgatga acccaatccc gattggtctt ccatcaatga atcctggaaa    5580
aacctgtacg cattccagtc atcagaacag gaatttgcca gagcaaagaa ggttagtaca    5640
tactttacct tgacaggtat tccctcccaa ttcattcctg atcctttgt aaacattgag     5700 actatgctac aaatattcgg agtacccacg ggtgtgtctc atgcggctgc cttaaaatca    5760
tctgatagac ctgcagattt attgaccatt agcctttttt atatggcgat tatatcgtat    5820
tataacatca atcatatcag agtaggaccg atacctccga accccccatc agatggaatt    5880
gcacaaaatg tggggatcgc tataactggt ataagctttt ggctgagttt gatggagaaa    5940
gacattccac tatatcaaca gtgtttggca gttatccagc aatcattcc gattaggtgg     6000 gaggctattt cagtaaaagg aggatacaag cagaagtgga gtactagagg tgatgggctc    6060
ccaaaagata cccgaatttc agactccttg gccccaatcg ggaactggat cagatctttg    6120
gaattggtcc gaaaccaagt tcgtctaaat ccattcaata agatcttgtt caatcagcta    6180
tgtcgtacag tggataatca tttgaagtgg tcaaatttgc gaaaaaacac aggaatgatt    6240
gaatggatca atgggcgaat ttcaaaagaa gaccggtcta tactgatgtt gaagagtgac    6300
ctacatgagg aaaactcttg gagagattaa                                     6330
```

<210> SEQ ID NO 19
<211> LENGTH: 2109
<212> TYPE: PRT
<213> ORGANISM: Artificial Sequence
<220> FEATURE:
<223> OTHER INFORMATION: Synthetic sequence

<400> SEQUENCE: 19

Met Glu Val His Asp Phe Glu Thr Asp Glu Phe Asn Asp Phe Asn Glu
1               5                   10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
        35                  40                  45

Asp Ile Asp Asn Leu Ile Arg Lys Phe Asn Ser Leu Pro Ile Pro Ser
    50                  55                  60

-continued

```
Met Trp Asp Ser Lys Asn Trp Asp Gly Val Leu Glu Met Leu Thr Ser
 65                  70                  75                  80

Cys Gln Ala Asn Pro Ile Ser Thr Ser Gln Met His Lys Trp Met Gly
                 85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
    130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190

Ser Ser His Gly Thr Asn Ile Cys Arg Ile Arg Val Pro Ser Leu Gly
        195                 200                 205

Pro Thr Phe Ile Ser Glu Gly Trp Ala Tyr Phe Lys Lys Leu Asp Ile
    210                 215                 220

Leu Met Asp Arg Asn Phe Leu Leu Met Val Lys Asp Val Ile Ile Gly
225                 230                 235                 240

Arg Met Gln Thr Val Leu Ser Met Val Cys Arg Ile Asp Asn Leu Phe
                245                 250                 255

Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
    275                 280                 285

Val Glu Pro Ile Cys Asn Leu Lys Leu Met Lys Leu Ala Arg Glu Ser
290                 295                 300

Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
                325                 330                 335

Asp Gln Ile Met Ser Val Lys Thr Val Asp Leu Thr Leu Val Ile Tyr
            340                 345                 350

Gly Ser Phe Arg His Trp Gly His Pro Phe Ile Asp Tyr Tyr Thr Gly
    355                 360                 365

Leu Glu Lys Leu His Ser Gln Val Thr Met Lys Lys Asp Ile Asp Val
370                 375                 380

Ser Tyr Ala Lys Ala Leu Ala Ser Asp Leu Ala Arg Ile Val Leu Phe
385                 390                 395                 400

Gln Gln Phe Asn Asp His Lys Lys Trp Phe Val Asn Gly Asp Leu Leu
                405                 410                 415

Pro His Asp His Pro Phe Lys Ser His Val Lys Glu Asn Thr Trp Pro
            420                 425                 430

Thr Ala Ala Gln Val Gln Asp Phe Gly Asp Lys Trp His Glu Leu Pro
    435                 440                 445

Leu Ile Lys Cys Phe Glu Ile Pro Asp Leu Leu Asp Pro Ser Ile Ile
450                 455                 460

Tyr Ser Asp Lys Ser His Ser Met Asn Arg Ser Glu Val Leu Lys His
465                 470                 475                 480

Val Arg Met Asn Pro Asn Thr Pro Ile Pro Ser Lys Lys Val Leu Gln
```

```
                485             490             495
Thr Met Leu Asp Thr Lys Ala Thr Asn Trp Lys Glu Phe Leu Lys Glu
                500             505             510

Ile Asp Glu Lys Gly Leu Asp Asp Asp Leu Ile Ile Gly Leu Lys
                515             520             525

Gly Lys Glu Arg Glu Leu Lys Leu Ala Gly Arg Phe Phe Ser Leu Met
        530             535             540

Ser Trp Lys Leu Arg Glu Tyr Phe Val Ile Thr Glu Tyr Leu Ile Lys
545             550             555             560

Thr His Phe Val Pro Met Phe Lys Gly Leu Thr Met Ala Asp Asp Leu
                565             570             575

Thr Ala Val Ile Lys Lys Met Leu Asp Ser Ser Gly Gln Gly Leu
            580             585             590

Lys Ser Tyr Glu Ala Ile Cys Ile Ala Asn His Ile Asp Tyr Glu Lys
            595             600             605

Trp Asn Asn His Gln Arg Lys Leu Ser Asn Gly Pro Val Phe Arg Val
            610             615             620

Met Gly Gln Phe Leu Gly Tyr Pro Ser Leu Ile Glu Arg Thr His Glu
625             630             635             640

Phe Phe Glu Lys Ser Leu Ile Tyr Tyr Asn Gly Arg Pro Asp Leu Met
                645             650             655

Arg Val His Asn Asn Thr Leu Ile Asn Ser Thr Ser Gln Arg Val Cys
                660             665             670

Trp Gln Gly Gln Glu Gly Gly Leu Glu Gly Leu Arg Gln Lys Gly Trp
            675             680             685

Ser Ile Leu Asn Leu Leu Val Ile Gln Arg Glu Ala Lys Ile Arg Asn
            690             695             700

Thr Ala Val Lys Val Leu Ala Gln Gly Asp Asn Gln Val Ile Cys Thr
705             710             715             720

Gln Tyr Lys Thr Lys Lys Ser Arg Asn Val Val Glu Leu Gln Gly Ala
                725             730             735

Leu Asn Gln Met Val Ser Asn Asn Glu Lys Ile Met Thr Ala Ile Lys
            740             745             750

Ile Gly Thr Gly Lys Leu Gly Leu Leu Ile Asn Asp Asp Glu Thr Met
            755             760             765

Gln Ser Ala Asp Tyr Leu Asn Tyr Gly Lys Ile Pro Ile Phe Arg Gly
        770             775             780

Val Ile Arg Gly Leu Glu Thr Lys Arg Trp Ser Arg Val Thr Cys Val
785             790             795             800

Thr Asn Asp Gln Ile Pro Thr Cys Ala Asn Ile Met Ser Ser Val Ser
                805             810             815

Thr Asn Ala Leu Thr Val Ala His Phe Ala Glu Asn Pro Ile Asn Ala
            820             825             830

Met Ile Gln Tyr Asn Tyr Phe Gly Thr Phe Ala Arg Leu Leu Leu Met
            835             840             845

Met His Asp Pro Ala Leu Arg Gln Ser Leu Tyr Glu Val Gln Asp Lys
        850             855             860

Ile Pro Gly Leu His Ser Ser Thr Phe Lys Tyr Ala Met Leu Tyr Leu
865             870             875             880

Asp Pro Ser Ile Gly Gly Val Ser Gly Met Ser Leu Ser Arg Phe Leu
                885             890             895

Ile Arg Ala Phe Pro Asp Pro Val Thr Glu Ser Leu Ser Phe Trp Arg
            900             905             910
```

```
Phe Ile His Val His Ala Arg Ser Glu His Leu Lys Glu Met Ser Ala
        915                 920                 925

Val Phe Gly Asn Pro Glu Ile Ala Lys Phe Arg Ile Thr His Ile Asp
    930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Cys Leu Ile Glu Ser
                965                 970                 975

Arg Gln Thr Ile Arg Asn Gln Val Ile Lys Asp Ala Thr Ile Tyr Leu
            980                 985                 990

Tyr His Glu Glu Asp Arg Leu Arg Ser Phe Leu Trp Ser Ile Asn Pro
        995                 1000                1005

Leu Phe Pro Arg Phe Leu Ser Glu Phe Lys Ser Gly Thr Phe Leu
    1010                1015                1020

Gly Val Ala Asp Gly Leu Ile Ser Leu Phe Gln Asn Ser Arg Thr
    1025                1030                1035

Ile Arg Asn Ser Phe Lys Lys Lys Tyr His Arg Glu Leu Asp Asp
    1040                1045                1050

Leu Ile Val Arg Ser Glu Val Ser Ser Leu Thr His Leu Gly Lys
    1055                1060                1065

Leu His Leu Arg Arg Gly Ser Cys Lys Met Trp Thr Cys Ser Ala
    1070                1075                1080

Thr His Ala Asp Thr Leu Arg Tyr Lys Ser Trp Gly Arg Thr Val
    1085                1090                1095

Ile Gly Thr Thr Val Pro His Pro Leu Glu Met Leu Gly Pro Gln
    1100                1105                1110

His Arg Lys Glu Thr Pro Cys Ala Pro Cys Asn Thr Ser Gly Phe
    1115                1120                1125

Asn Tyr Val Ser Val His Cys Pro Asp Gly Ile His Asp Val Phe
    1130                1135                1140

Ser Ser Arg Gly Pro Leu Pro Ala Tyr Leu Gly Ser Lys Thr Ser
    1145                1150                1155

Glu Ser Thr Ser Ile Leu Gln Pro Trp Glu Arg Glu Ser Lys Val
    1160                1165                1170

Pro Leu Ile Lys Arg Ala Thr Arg Leu Arg Asp Ala Ile Ser Trp
    1175                1180                1185

Phe Val Glu Pro Asp Ser Lys Leu Ala Met Thr Ile Leu Ser Asn
    1190                1195                1200

Ile His Ser Leu Thr Gly Glu Glu Trp Thr Lys Arg Gln His Gly
    1205                1210                1215

Phe Lys Arg Thr Gly Ser Ala Leu His Arg Phe Ser Thr Ser Arg
    1220                1225                1230

Met Ser His Gly Gly Phe Ala Ser Gln Ser Thr Ala Ala Leu Thr
    1235                1240                1245

Arg Leu Met Ala Thr Thr Asp Thr Met Arg Asp Leu Gly Asp Gln
    1250                1255                1260

Asn Phe Asp Phe Leu Phe Gln Ala Thr Leu Leu Tyr Ala Gln Ile
    1265                1270                1275

Thr Thr Thr Val Ala Arg Asp Gly Trp Ile Thr Ser Cys Thr Asp
    1280                1285                1290

His Tyr His Ile Ala Cys Lys Ser Cys Leu Arg Pro Ile Glu Glu
    1295                1300                1305
```

```
Ile Thr Leu Asp Ser Ser Met Asp Tyr Thr Pro Pro Asp Val Ser
    1310            1315            1320

His Val Leu Lys Thr Trp Arg Asn Gly Glu Gly Ser Trp Gly Gln
    1325            1330            1335

Glu Ile Lys Gln Ile Tyr Pro Leu Glu Gly Asn Trp Lys Asn Leu
    1340            1345            1350

Ala Pro Ala Glu Gln Ser Tyr Gln Val Gly Arg Cys Ile Gly Phe
    1355            1360            1365

Leu Tyr Gly Asp Leu Ala Tyr Arg Lys Ser Thr His Ala Glu Asp
    1370            1375            1380

Ser Ser Leu Phe Pro Leu Ser Ile Gln Gly Arg Ile Arg Gly Arg
    1385            1390            1395

Gly Phe Leu Lys Gly Leu Leu Asp Gly Leu Met Arg Ala Ser Cys
    1400            1405            1410

Cys Gln Val Ile His Arg Arg Ser Leu Ala His Leu Lys Arg Pro
    1415            1420            1425

Ala Asn Ala Val Tyr Gly Gly Leu Ile Tyr Leu Ile Asp Lys Leu
    1430            1435            1440

Ser Val Ser Pro Pro Phe Leu Ser Leu Thr Arg Ser Gly Pro Ile
    1445            1450            1455

Arg Asp Glu Leu Glu Thr Ile Pro His Lys Ile Pro Thr Ser Tyr
    1460            1465            1470

Pro Thr Ser Asn Arg Asp Met Gly Val Ile Val Arg Asn Tyr Phe
    1475            1480            1485

Lys Tyr Gln Cys Arg Leu Ile Glu Lys Gly Lys Tyr Arg Ser His
    1490            1495            1500

Tyr Ser Gln Leu Trp Leu Phe Ser Asp Val Leu Ser Ile Asp Phe
    1505            1510            1515

Ile Gly Pro Phe Ser Ile Ser Thr Thr Leu Leu Gln Ile Leu Tyr
    1520            1525            1530

Lys Pro Phe Leu Ser Gly Lys Asp Lys Asn Glu Leu Arg Glu Leu
    1535            1540            1545

Ala Asn Leu Ser Ser Leu Leu Arg Ser Gly Glu Gly Trp Glu Asp
    1550            1555            1560

Ile His Val Lys Phe Phe Thr Lys Asp Ile Leu Leu Cys Pro Glu
    1565            1570            1575

Glu Ile Arg His Ala Cys Lys Phe Gly Ile Ala Lys Asp Asn Asn
    1580            1585            1590

Lys Asp Met Ser Tyr Pro Pro Trp Gly Arg Glu Ser Arg Gly Thr
    1595            1600            1605

Ile Thr Thr Ile Pro Val Tyr Tyr Thr Thr Pro Tyr Pro Lys
    1610            1615            1620

Met Leu Glu Met Pro Pro Arg Ile Gln Asn Pro Leu Leu Ser Gly
    1625            1630            1635

Ile Arg Leu Gly Gln Leu Pro Thr Gly Ala His Tyr Lys Ile Arg
    1640            1645            1650

Ser Ile Leu His Gly Met Gly Ile His Tyr Arg Asp Phe Leu Ser
    1655            1660            1665

Cys Gly Asp Gly Ser Gly Gly Met Thr Ala Ala Leu Leu Arg Glu
    1670            1675            1680

Asn Val His Ser Arg Gly Ile Phe Asn Ser Leu Leu Glu Leu Ser
    1685            1690            1695

Gly Ser Val Met Arg Gly Ala Ser Pro Glu Pro Pro Ser Ala Leu
```

```
                1700                1705                1710

Glu Thr Leu Gly Gly Asp Lys Ser Arg Cys Val Asn Gly Glu Thr
    1715                1720                1725

Cys Trp Glu Tyr Pro Ser Asp Leu Cys Asp Pro Arg Thr Trp Asp
    1730                1735                1740

Tyr Phe Leu Arg Leu Lys Ala Gly Leu Gly Leu Gln Ile Asp Leu
    1745                1750                1755

Ile Val Met Asp Met Glu Val Arg Asp Ser Ser Thr Ser Leu Lys
    1760                1765                1770

Ile Glu Thr Asn Val Arg Asn Tyr Val His Arg Ile Leu Asp Glu
    1775                1780                1785

Gln Gly Val Leu Ile Tyr Lys Thr Tyr Gly Thr Tyr Ile Cys Glu
    1790                1795                1800

Ser Glu Lys Asn Ala Val Thr Ile Leu Gly Pro Met Phe Lys Thr
    1805                1810                1815

Val Asp Leu Val Gln Thr Glu Phe Ser Ser Ser Gln Thr Ser Glu
    1820                1825                1830

Val Tyr Met Val Cys Lys Gly Leu Lys Lys Leu Ile Asp Glu Pro
    1835                1840                1845

Asn Pro Asp Trp Ser Ser Ile Asn Glu Ser Trp Lys Asn Leu Tyr
    1850                1855                1860

Ala Phe Gln Ser Ser Glu Gln Glu Phe Ala Arg Ala Lys Lys Val
    1865                1870                1875

Ser Thr Tyr Phe Thr Leu Thr Gly Ile Pro Ser Gln Phe Ile Pro
    1880                1885                1890

Asp Pro Phe Val Asn Ile Glu Thr Met Leu Gln Ile Phe Gly Val
    1895                1900                1905

Pro Thr Gly Val Ser His Ala Ala Ala Leu Lys Ser Ser Asp Arg
    1910                1915                1920

Pro Ala Asp Leu Leu Thr Ile Ser Leu Phe Tyr Met Ala Ile Ile
    1925                1930                1935

Ser Tyr Tyr Asn Ile Asn His Ile Arg Val Gly Pro Ile Pro Pro
    1940                1945                1950

Asn Pro Pro Ser Asp Gly Ile Ala Gln Asn Val Gly Ile Ala Ile
    1955                1960                1965

Thr Gly Ile Ser Phe Trp Leu Ser Leu Met Glu Lys Asp Ile Pro
    1970                1975                1980

Leu Tyr Gln Gln Cys Leu Ala Val Ile Gln Gln Ser Phe Pro Ile
    1985                1990                1995

Arg Trp Glu Ala Ile Ser Val Lys Gly Gly Tyr Lys Gln Lys Trp
    2000                2005                2010

Ser Thr Arg Gly Asp Gly Leu Pro Lys Asp Thr Arg Ile Ser Asp
    2015                2020                2025

Ser Leu Ala Pro Ile Gly Asn Trp Ile Arg Ser Leu Glu Leu Val
    2030                2035                2040

Arg Asn Gln Val Arg Leu Asn Pro Phe Asn Lys Ile Leu Phe Asn
    2045                2050                2055

Gln Leu Cys Arg Thr Val Asp Asn His Leu Lys Trp Ser Asn Leu
    2060                2065                2070

Arg Lys Asn Thr Gly Met Ile Glu Trp Ile Asn Gly Arg Ile Ser
    2075                2080                2085

Lys Glu Asp Arg Ser Ile Leu Met Leu Lys Ser Asp Leu His Glu
    2090                2095                2100
```

Glu Asn Ser Trp Arg Asp
    2105

<210> SEQ ID NO 20
<211> LENGTH: 21
<212> TYPE: DNA
<213> ORGANISM: Artificial Sequence
<220> FEATURE:
<223> OTHER INFORMATION: Synthetic sequence

<400> SEQUENCE: 20
cgagttggta tttatctttg c                                              21

<210> SEQ ID NO 21
<211> LENGTH: 19
<212> TYPE: DNA
<213> ORGANISM: Artificial Sequence
<220> FEATURE:
<223> OTHER INFORMATION: Synthetic sequence

<400> SEQUENCE: 21
gtacgtcatg cgctcatcg                                                 19

<210> SEQ ID NO 22
<211> LENGTH: 30
<212> TYPE: DNA
<213> ORGANISM: Artificial Sequence
<220> FEATURE:
<223> OTHER INFORMATION: Synthetic sequence

<400> SEQUENCE: 22
ctcgtctctt cttctccttc ctagcattga                                     30

<210> SEQ ID NO 23
<211> LENGTH: 27
<212> TYPE: DNA
<213> ORGANISM: Artificial Sequence
<220> FEATURE:
<223> OTHER INFORMATION: Synthetic sequence

<400> SEQUENCE: 23
catcaggatg gtcttggcga ttctagc                                        27

<210> SEQ ID NO 24
<211> LENGTH: 30
<212> TYPE: DNA
<213> ORGANISM: Artificial Sequence
<220> FEATURE:
<223> OTHER INFORMATION: Synthetic sequence

<400> SEQUENCE: 24
ctcgtctctt cttctccttc ctagcattga                                     30

<210> SEQ ID NO 25
<211> LENGTH: 11200
<212> TYPE: DNA
<213> ORGANISM: Vesicular stomatitis virus

<400> SEQUENCE: 25
acgaagacaa acaaaccatt attatcatta aaaggctcag gagaaacttt aacagtaatc    60
aaaatgtctg ttacagtcaa gagaatcatt gacaacacag tcatagttcc aaaacttcct    120
gcaaatgagg atccagtgga atacccggca gattacttca gaaaatcaaa ggagattcct    180
ctttacatca atactacaaa agtttgtca gatctaagag gatatgtcta ccaaggcctc    240

| | |
|---|---|
| aaatccggaa atgtatcaat catacatgtc aacagctact tgtatggagc attaaaggac | 300 |
| atccgggta agttggataa agattggtca agtttcggaa taaacatcgg aaagcaggg | 360 |
| gatacaatcg gaatatttga ccttgtatcc ttgaaagccc tggacggcgt acttccagat | 420 |
| ggagtatcgg atgcttccag aaccagcgca gatgacaaat ggttgccttt gtatctactt | 480 |
| ggcttataca gagtgggcag aacacaaatg cctgaataca gaaaaaagct catggatggg | 540 |
| ctgacaaatc aatgcaaaat gatcaatgaa cagtttgaac ctcttgtgcc agaaggtcgt | 600 |
| gacattttg atgtgtgggg aaatgacagt aattacacaa aaattgtcgc tgcagtggac | 660 |
| atgttcttcc acatgttcaa aaaacatgaa tgtgcctcgt tcagatacgg aactattgtt | 720 |
| tccagattca aagattgtgc tgcattggca acatttggac acctctgcaa ataaccgga | 780 |
| atgtctacag aagatgtaac gacctggatc ttgaaccgag aagttgcaga tgaaatggtc | 840 |
| caaatgatgc ttccaggcca agaaattgac aaggccgatt catacatgcc ttatttgatc | 900 |
| gactttggat tgtcttctaa gtctccatat tcttccgtca aaaaccctgc cttccacttc | 960 |
| tgggggcaat tgacagctct tctgctcaga tccaccagag caaggaatgc ccgacagcct | 1020 |
| gatgacattg agtatacatc tcttactaca gcaggtttgt tgtacgctta tgcagtagga | 1080 |
| tcctctgccg acttggcaca acagttttgt gttggagata caaatacac tccagatgat | 1140 |
| agtaccggag gattgacgac taatgcaccg ccacaaggca gagatgtggt cgaatggctc | 1200 |
| ggatggtttg aagatcaaaa cagaaaaccg actcctgata tgatgcagta tgcgaaaaga | 1260 |
| gcagtcatgt cactgcaagg cctaagagag aagacaattg gcaagtatgc taagtcagaa | 1320 |
| tttgacaaat gaccctataa ttctcagatc acctattata tattatgcta catatgaaaa | 1380 |
| aaactaacag atatcatgga taatctcaca aaagttcgtg agtatctcaa gtcctactct | 1440 |
| cgtctagatc aggcggtagg agagatagat gagatcgaag cacaacgagc tgaaaagtcc | 1500 |
| aattatgagt tgttccaaga ggacggagtg gaagagcata ctaggccctc ttatttcag | 1560 |
| gcagcagatg attctgacac agaatctgaa ccagaaattg aagacaatca aggcttgtat | 1620 |
| gtaccagatc cggaagctga gcaagttgaa ggctttatac aggggccttt agatgactat | 1680 |
| gcagatgagg acgtggatgt tgtattcact tcggactgga acagcctga gcttgaatcc | 1740 |
| gacgagcatg gaaagacctt acggttgaca ttgccagagg gtttaagtgg agagcagaaa | 1800 |
| tcccagtggc ttttgacgat taagcagtc gttcaaagtg ccaaacactg gaatctggca | 1860 |
| gagtgcacat ttgaagcatc gggagaaggg gtcatcataa aaaagcgcca gataactccg | 1920 |
| gatgtatata aggtcactcc agtgatgaac acacatccgt accaatcaga agccgtatca | 1980 |
| gatgtttggt ctctctcaaa gacatccatg actttccaac ccaagaaagc aagtcttcag | 2040 |
| cctctcacca tatccttgga tgaattgttc tcatctagag gagaattcat ctctgtcgga | 2100 |
| ggtaacggac gaatgtctca taagaggcc atcctgctcg gtctgaggta caaaaagttg | 2160 |
| tacaatcagg cgagagtcaa atattctctg tagactatga aaaaagtaa cagatatcac | 2220 |
| aatctaagtg ttatcccaat ccattcatca tgagttcctt aaagaagatt ctcggtctga | 2280 |
| aggggaaagg taagaaatct aagaaattag ggatcgcacc accccttat gaagaggaca | 2340 |
| ctagcatgga gtatgctccg agcgctccaa ttgacaaatc ctattttgga gttgacgaga | 2400 |
| tggacaccta tgatccgaat caattaagat atgagaaatt cttctttaca gtgaaaatga | 2460 |
| cggttagatc taatcgtccg ttcagaacat actcagatgt ggcagccgct gtatcccatt | 2520 |
| gggatcacat gtacatcgga atggcaggga aacgtccctt ctacaaaatc ttggcttttt | 2580 |

```
tgggttcttc taatctaaag gccactccag cggtattggc agatcaaggt caaccagagt    2640
atcacgctca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctagc ttccagcttc tgaacaatcc ccggtttact cagtctctcc taattccagc    3000 cttcgaaca actaatatcc tgtcttttct atccctatga aaaaactaa cagagatcga    3060 tctgttcct tgacaccatg aagtgccttt tgtacttagc ttttttattc atcggggtga    3120
attgcaagtt caccatagtt tttccacaca accgaaaagg aaactggaaa aatgttcctt    3180
ccaattacca ttattgcccg tcaagctcag atttaaattg gcataatgac ttaataggca    3240
cagccttaca agtcaaaatg cccaagagtc acaaggctat tcaagcagac ggttggatgt    3300
gtcatgcttc caaatgggtc actacttgtg atttccgctg gtacggaccg gagtatataa    3360
cacattccat ccgatccttc actccatctg tagaacaatg caaggaaagc attgaacaaa    3420
cgaaacaagg aacttggctg aatccaggct cccctcctca aagttgtgga tatgcaactg    3480
tgacggatgc tgaagcagcg attgtccagg tgactcctca ccatgtgctt gttgatgaat    3540
acacaggaga atgggttgat tcacagttca tcaacgaaa atgcagcaat gacatatgcc    3600
ccactgtcca taactccaca acctggcatt ccgactataa ggtcaaaggg ctatgtgatt    3660
ctaacctcat ttcatggac atcaccttct tctcagagga cggagagcta tcatccctag    3720
gaaaggaggg cacagggttc agaagtaact actttgctta tgaaactgga gacaaggcct    3780
gcaaaatgca gtactgcaag cattgggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctcat tcaggacgtt gagaggatct    3960
tggattattc cctctgccaa gaaacctgga gcaaaatcag agcgggtctt cccatctctc    4020
cagtggatct cagctatctt gctcctaaaa acccaggaac cggtcctgtc tttaccataa    4080
tcaatggtac cctaaaatac tttgagacca gatacatcag agtcgatatt gctgctccaa    4140
tcctctcaag aatggtcgga atgatcagtg gaactaccac agaaagggaa ctgtgggatg    4200
actgggctcc atatgaagac gtggaaattg gacccaatgg agttctgagg accagttcag    4260
gatataagtt tcctttatat atgattggac atggtatgtt ggactccgat cttcatctta    4320
gctcaaaggc tcaggtgttt gaacatcctc acattcaaga cgctgcttcg cagcttcctg    4380
atgatgagac tttattttttt ggtgatactg ggctatccaa aaatccaatc gagtttgtag    4440
aaggttggtt cagtagttgg aagagctcta ttgcctcttt ttgctttatc ataggggtaa    4500
tcattggact attcttggtt ctccgagttg gtatttatct ttgcattaaa ttaaagcaca    4560
ccaagaaaag acagatttat acagacatag agatgaaccg acttggaaag taactcaaat    4620
cctgcacaac agattcttca tgtttgaacc aaatcaactt gtgatatcat gctcaaagag    4680
gccttaatta tattttaatt tttaattttt atgaaaaaaa ctaacagcaa tcatggaagt    4740
ccacgatttt gagaccgacg agttcaatga tttcaatgaa gatgactatg ccacaagaga    4800
attcctgaat cccgatgagc gcatgacgta cttgaatcat gctgattaca atttgaattc    4860
tcctctaatt agtgatgata ttgacaattt gatcaggaaa ttcaattctc ttccgattcc    4920
ctcgatgtgg gatagtaaga actgggatgg agttcttgag atgttaacat catgtcaagc    4980
```

```
caatcccatc tcaacatctc agatgcataa atggatggga agttggttaa tgtctgataa   5040
tcatgatgcc agtcaagggt atagttttt  acatgaagtg gacaaagagg cagaaataac   5100
atttgacgtg gtggagacct tcatccgcgg ctggggcaac aaaccaattg aatacatcaa   5160
aaaggaaaga tggactgact cattcaaaat tctcgcttat ttgtgtcaaa agttttttgga  5220 cttacacaag ttgacattaa tcttaaatgc tgtctctgag gtggaattgc tcaacttggc   5280
gaggactttc aaaggcaaag tcagaagaag ttctcatgga acgaacatat gcaggattag   5340
ggttcccagc ttgggtccta ctttattttc agaaggatgg gcttacttca agaaacttga   5400
tattctaatg gaccgaaact ttctgttaat ggtcaaagat gtgattatag ggaggatgca   5460
aacggtgcta tccatggtat gtagaataga caacctgttc tcagagcaag acatcttctc   5520
ccttctaaat atctacagaa ttggagataa aattgtggag aggcagggaa atttttctta   5580
tgacttgatt aaaatggtgg aaccgatatg caacttgaag ctgatgaaat tagcaagaga   5640
atcaaggcct ttagtcccac aattccctca ttttgaaaat catatcaaga cttctgttga   5700
tgaaggggca aaaattgacc gaggtataag attcctccat gatcagataa tgagtgtgaa   5760
aacagtggat ctcacactgg tgatttatgg atcgttcaga cattgggtgc atcctttat   5820 agattattac actggactag aaaaattaca ttcccaagta accatgaaga aagatattga   5880
tgtgtcatat gcaaaagcac ttgcaagtga tttagctcgg attgttctat ttcaacagtt   5940
caatgatcat aaaaagtggt tcgtgaatgg agacttgctc cctcatgatc atccctttaa   6000
aagtcatgtt aaagaaaata catggcccac agctgctcaa gttcaagatt ttggagataa   6060
atggcatgaa cttccgctga ttaaatgttt tgaaataccc gacttactag acccatcgat   6120
aatatactct gacaaaagtc attcaatgaa taggtcagag gtgttgaaac atgtccgaat   6180
gaatccgaac actcctatcc ctagtaaaaa ggtgttgcag actatgttgg acacaaaggc   6240
taccaattgg aaagaatttc ttaaagagat tgatgagaag ggcttagatg atgatgatct   6300
aattattggt cttaaaggaa aggagaggga actgaagttg gcaggtagat ttttctccct   6360
aatgtcttgg aaattgcgag aatactttgt aattaccgaa tatttgataa agactcattt   6420
cgtccctatg tttaaaggcc tgacaatggc ggacgatcta actgcagtca ttaaaaagat   6480
gttagattcc tcatccggcc aaggattgaa gtcatatgag gcaatttgca tagccaatca   6540
cattgattac gaaaaatgga ataaccacca aggaagtta  tcaaacggcc cagtgttccg   6600
agttatgggc cagttcttag gttatccatc cttaatcgag agaactcatg aatttttttga  6660 gaaaagtctt atatactaca atggaagacc agacttgatg cgtgttcaca caacacact   6720 gatcaattca acctcccaac gagtttgttg gcaaggacaa gagggtggac tggaaggtct   6780
acggcaaaaa ggatggagta tcctcaatct actggttatt caagagagg  ctaaaatcag   6840 aaacactgct gtcaaagtct tggcacaagg tgataatcaa gttatttgca cacagtataa   6900
aacgaagaaa tcgagaaacg ttgtagaatt acagggtgct ctcaatcaaa tggtttctaa   6960
taatgagaaa attatgactg caatcaaaat agggacaggg aagttaggac ttttgataaa   7020
tgacgatgag actatgcaat ctgcagatta cttgaattat ggaaaatac  cgattttccg   7080 tggagtgatt agagggttag agaccaagag atggtcacga gtgacttgtg tcaccaatga   7140
ccaaataccc acttgtgcta atataatgag ctcagtttcc acaaatgctc tcaccgtagc   7200
tcattttgct gagaacccaa tcaatgccat gatacagtac aattattttg ggacatttgc   7260
tagactcttg ttgatgatgc atgatcctgc tcttcgtcaa tcattgtatg aagttcaaga   7320
```

```
taagataccg ggcttgcaca gttctacttt caaatacgcc atgttgtatt tggacccttc    7380
cattggagga gtgtcgggca tgtctttgtc caggttttg attagagcct tcccagatcc     7440
cgtaacagaa agtctctcat tctggagatt catccatgta catgctcgaa gtgagcatct    7500
gaaggagatg agtgcagtat ttggaaaccc cgagatagcc aagtttcgaa taactcacat    7560
agacaagcta gtagaagatc caacctctct gaacatcgct atgggaatga gtccagcgaa    7620
cttgttaaag actgaggtta aaaaatgctt aatcgaatca agacaaacca tcaggaacca    7680
ggtgattaag gatgcaacca tatatttgta tcatgaagag gatcggctca gaagtttctt    7740
atggtcaata aatcctctgt tccctagatt tttaagtgaa ttcaaatcag gcacttttt     7800 gggagtcgca gacgggctca tcagtctatt tcaaaattct cgtactattc ggaactcctt    7860
taagaaaaag tatcataggg aattggatga tttgattgtg aggagtgagg tatcctcttt    7920
gacacattta gggaaacttc atttgagaag gggatcatgt aaaatgtgga catgttcagc    7980
tactcatgct gacacattaa gatacaaatc ctggggccgt acagttattg gacaactgt     8040 accccatcca ttagaaatgt tgggtccaca acatcgaaaa gagactcctt gtgcaccatg    8100
taacacatca gggttcaatt atgtttctgt gcattgtcca gacgggatcc atgacgtctt    8160
tagttcacgg ggaccattgc ctgcttatct agggtctaaa acatctgaat ctacatctat    8220
tttgcagcct tgggaaaggg aaagcaaagt cccactgatt aaaagagcta cacgtcttag    8280
agatgctatc tcttggtttg ttgaacccga ctctaaacta gcaatgacta cttttctaa     8340 catccactct ttaacaggcg aagaatggac caaaaggcag catgggttca aaagaacagg    8400 gtctgcccctt cataggtttt cgacatctcg gatgagccat ggtgggttcg catctcagag    8460
cactgcagca ttgaccaggt tgatggcaac tacagacacc atgagggatc tgggagatca    8520
gaatttcgac tttttattcc aagcaacgtt gctctatgct caaattacca ccactgttgc    8580
aagagacgga tggatcacca gttgtacaga tcattatcat attgcctgta agtcctgttt    8640
gagacccata aaagagatca ccctggactc aagtatggac tacacgcccc cagatgtatc    8700
ccatgtgctg aagacatgga ggaatgggga aggttcgtgg ggacaagaga taaaacagat    8760
ctatccttta aagggaatt ggaagaattt agcacctgct gagcaatcct atcaagtcgg     8820
cagatgtata ggttttctat atggagactt ggcgtataga aaatctactc atgccgagga    8880
cagttctcta tttcctctat ctatacaagg tcgtattaga ggtcgaggtt tcttaaaagg    8940
gttgctagac ggattaatga gagcaagttg ctgccaagta atacaccgga gaagtctggc    9000
tcatttgaag aggccggcca acgcagtgta cggaggtttg atttacttga ttgataaatt    9060
gagtgtatca cctccattcc tttctcttac tagatcagga cctattagag acgaattaga    9120
aacgattccc cacaagatcc caacctccta tccgacaagc aaccgtgata tgggggtgat    9180
tgtcagaaat tacttcaaat accaatgccg tctaattgaa aagggaaaat acagatcaca    9240
ttattcacaa ttatggttat tctcagatgt cttatccata gacttcattg gaccattctc    9300
tatttccacc accctcttgc aaatcctata caagccattt ttatctggga aagataagaa    9360
tgagttgaga gagctggcaa atctttcttc attgctaaga tcaggagagg ggtgggaaga    9420
catacatgtg aaattcttca ccaaggacat attattgtgt ccagaggaaa tcagacatgc    9480
ttgcaagttc gggattgcta aggataataa taaagacatg agctatcccc cttggggaag    9540
ggaatccaga gggacaatta caacaatccc tgtttattat acgaccaccc cttacccaaa    9600
gatgctagag atgcctccaa gaatccaaaa tccctgctg tccggaatca ggttgggcca     9660
attaccaact ggcgctcatt ataaaattcg gagtatatta catggaatgg gaatccatta    9720
```

-continued

```
cagggacttc ttgagttgtg gagacggctc cggagggatg actgctgcat tactacgaga    9780
aaatgtgcat agcagaggaa tattcaatag tctgttagaa ttatcagggt cagtcatgcg    9840
aggcgcctct cctgagcccc ccagtgccct agaaacttta ggaggagata aatcgagatg    9900
tgtaaatggt gaaacatgtt gggaatatcc atctgactta tgtgacccaa ggacttggga    9960
ctatttcctc cgactcaaag caggcttggg gcttcaaatt gatttaattg taatggatat   10020
ggaagttcgg gattcttcta ctagcctgaa aattgagacg aatgttagaa attatgtgca   10080
ccggattttg gatgagcaag gagttttaat ctacaagact tatggaacat atatttgtga   10140
gagcgaaaag aatgcagtaa caatccttgg tcccatgttc aagacggtcg acttagttca   10200
aacagaattt agtagttctc aaacgtctga agtatatatg gtatgtaaag gtttgaagaa   10260
attaatcgat gaacccaatc ccgattggtc ttccatcaat gaatcctgga aaaacctgta   10320
cgcattccag tcatcagaac aggaatttgc cagagcaaag aaggttagta catactttac   10380
cttgacaggt attccctccc aattcattcc tgatcctttt gtaaacattg agactatgct   10440
acaaatattc ggagtaccca cgggtgtgtc tcatgcggct gccttaaaat catctgatag   10500
acctgcagat ttattgacca ttagcctttt ttatatggcg attatatcgt attataacat   10560
caatcatatc agagtaggac cgatacctcc gaaccccca tcagatggaa ttgcacaaaa    10620
tgtggggatc gctataactg gtataagctt ttggctgagt ttgatggaga aagacattcc   10680
actatatcaa cagtgtttgg cagttatcca gcaatcattt ccgattaggt gggaggctat   10740
ttcagtaaaa ggaggataca agcagaagtg gagtactaga ggtgatgggc tcccaaaaga   10800
tacccgaatt tcagactcct tggccccaat cgggaactgg atcagatctt tggaattggt   10860
ccgaaaccaa gttcgtctaa atccattcaa taagatcttg ttcaatcagc tatgtcgtac   10920
agtggataat catttgaagt ggtcaaattt gcgaaaaaac acaggaatga ttgaatggat   10980
caatgggcga atttcaaaag aagaccggtc tatactgatg ttgaagagtg acctacatga   11040
ggaaaactct tggagagatt aaaaaatcag gaggagactc caaactttaa gtatgaaaaa   11100
aactttgatc cttaagaccc tcttgtggtt tttatttttt tatctggttt tgtggtcttc   11160
gtgggtcggc atggcatctc cacctcctcg cggtccgacc                         11200
```

RECOMBINANT VECTORS ENCODING ZIKA VIRUS PROTEIN SUBUNITS

CROSS-REFERENCE TO RELATED APPLICATIONS

This application is the National Stage of International Patent Application No. PCT/US2018/060137 claims priority to U.S. Provisional Patent Application No. 62/584,629, filed Nov. 10, 2017, the entire contents of each of which are hereby expressly incorporated by reference.

STATEMENT REGARDING FEDERALLY SPONSORED RESEARCH

This invention was made with government support under Grant No. P01 AI112524 awarded by the National Institutes of Health. The government has certain rights in the invention.

FIELD

Embodiments disclosed herein provide for compositions, methods, and uses of recombinant vectors encoding Zika virus protein subunits and immunogenic compositions thereof. Certain embodiments provide recombinant vectors encoding Zika virus nonstructural protein 1 (NS1 protein), and optionally Zika virus envelope (E) protein and premembrane (prM) protein. In certain embodiments, the vector encoding the Zika virus protein subunits is a vesicular stomatitis virus (VSV) vector. In some embodiments, the VSV vector backbone comprises an attenuating mutation. Other embodiments provide immunogenic compositions comprising a recombinant vector of the present disclosure. In some embodiments, the immunogenic compositions can be used in methods for inducing an effective immune response against Zika virus infection in a subject.

SEQUENCE LISTING

The instant application contains a Sequence Listing which has been submitted via EFS-Web in computer readable form, and which is hereby incorporated by reference in its entirety. The ASCII copy, created on Nov. 6, 2018, is named 509892.16_SEQ_LIST_ST25.txt, and is 32,964,087 bytes in size.

BACKGROUND

Zika virus (ZIKV) is a mosquito-borne flavivirus that was first identified in monkeys from the Zika Forest, near Lake Victoria, Uganda in 1947. Sporadic outbreaks of ZIKV have since been reported in Africa and Asia. Historically, people infected with Zika virus have no or mild symptoms, including fever, rash, muscle pain, red eyes, headache, and conjunctivitis. In 2015, a ZIKV pandemic began in South America, Central America, the Caribbean, and the USA, suddenly becoming a global public health issue. ZIKV from these recent outbreaks caused microcephaly, birth defects, Guillain-Barré syndrome, and other severe neurological disorders. ZIKV is primarily transmitted through the bite of an infected *Aedes* species mosquito (e.g., *Ae. aegypti* and *Ae. albopictus*) although other transmission modes such as sexual, blood transfusion, and maternal-fetal are also possible.

Currently, more than 50 countries in South America, North American, Asia, Africa, Oceania, and Micronesia have reported indigenous human ZIKV cases. The first confirmed case of ZIKV in in the U.S. was in Florida in 2016. Between that date and June of 2017 there have been 41,891 ZIKV cases confirmed in the US, including 5,296 cases in the continental U.S. and 36,595 cases in the U.S. territories of Puerto Rico, the U.S. Virgin Islands and American Samoa.

ZIKV is a member of the virus family Flaviviridae, which also includes other globally prevalent human pathogens such as dengue virus (DENV), yellow fever virus (YFV), West Nile virus (WNV), and Japanese encephalitis virus (JEV). The ZIKV genome encodes a single polyprotein that is cleaved posttranslationally into three structural proteins (capsid, pre-membrane, and envelope) and seven nonstructural proteins (NS1, NS2A, NS2B, NS3, NS4A, NS4B, and NS5). The E protein is a type II fusion protein which mediates cellular attachment and membrane fusion, and is the target for most neutralizing antibodies (Abs). Flavivirus prM protein typically associates with E to form heterodimers and is important for proper folding of E. Co-expression of prM and E of several flaviviruses including ZIKV results in the secretion of virus-like particles (VLPs) termed recombinant subviral particles. The prM protein is an integral part of both virions and subviral particles, and undergoes a cleavage event during virus maturation. Therefore, prM and E proteins have been the primary targets for the rational design of subunit and recombinant flavivirus vaccines.

Recently, several ZIKV vaccine candidates have been reported, including nucleic acid (DNA and mRNA), inactivated virus, subunit, VLP, vectored vaccines, and live attenuated vaccines. These vaccine candidates triggered various degrees of humoral and cellular immunity and protection in rodent and/or nonhuman primate models. Among these candidates, DNA vaccine, subunit vaccine, and inactivated vaccine have been initiated for clinical trials. Currently, all ZIKV subunit, DNA, and mRNA vaccines undergoing preclinical or clinical trial have been targeted on the E or prM-E antigen. Despite these efforts, currently, there is no FDA-approved vaccine or antiviral drug for ZIKV.

SUMMARY

The present disclosure provides recombinant vectors capable of expressing Zika virus protein subunits and eliciting an immune response against Zika virus when introduced into a subject.

In a first aspect, the present disclosure provides recombinant vectors comprising a polynucleotide sequence encoding a Zika virus nonstructural protein 1 (NS1 protein). In some embodiments, the Zika virus NS1 protein has at least 90% amino acid sequence identity with SEQ ID NO: 14. In some embodiments, the Zika virus NS1 protein comprises an amino acid sequence according to SEQ ID NO: 14.

In some embodiments, the recombinant vector further comprises one or more polynucleotide sequences encoding a Zika virus envelope (E) protein or truncation mutant thereof, and a Zika virus premembrane (prM) protein.

In some embodiments, the Zika virus E protein has at least 90% amino acid sequence identity with SEQ ID NO: 4; the Zika virus E protein truncation mutant has at least 90% amino acid sequence identity with one of SEQ ID NO 10 (E404), SEQ ID NO: 8 (E414), or SEQ ID NO: 6 (E415); and the Zika virus prM protein has at least 90% amino acid sequence identity with SEQ ID NO: 12.

In some embodiments, the recombinant vector encodes the Zika virus NS1 protein, the Zika virus E protein or truncation mutant thereof, and the Zika virus prM protein.

In some embodiments, the recombinant vector comprises a DNA plasmid vector or an RNA viral vector. In some embodiments, the viral vector is selected from the group comprising adenovirus, adeno-associated virus (AAV), retrovirus, lentivirus, vaccinia virus, cytomegalovirus, Sendai virus, modified vaccinia Ankara virus, and vesicular stomatitis virus (VSV).

In some embodiments, the recombinant vector comprises a VSV vector.

In some embodiments, VSV vector comprises at least one mutation in a methyltransferase-encoding region of an L protein of the VSV vector.

In some embodiments, the at least one mutation is a nucleic acid mutation that results in an amino acid mutation at a position in the VSV vector selected from the group of K1651, G1670, D1762, K1795, and E1833.

In some embodiments, the at least one mutation is a nucleic acid mutation that results in a G1670A mutation in the VSV vector.

In some embodiments, the VSV vector comprises a nucleic acid sequence having at least 90% sequence identity to SEQ ID NO: 16.

In some embodiments, the VSV vector comprises a nucleic acid sequence according to SEQ ID NO: 16, or SEQ ID NO: 16 encoding a G→A mutation at amino acid position 1670 of VSV L protein.

In a second aspect, the present disclosure immunogenic compositions comprising at least one recombinant vector according of the present disclosure and a pharmaceutically acceptable excipient. In some embodiments, the immunogenic composition comprises an adjuvant.

In a third aspect, the present disclosure provides methods for inducing an effective immune response against Zika virus in a subject, the method comprising administering to the subject an immunologically effective dose of an immunogenic composition of the present disclosure.

In some embodiments, the subject is human. In some embodiments, the subject is pregnant, may be pregnant, or is trying to get pregnant.

In some embodiments, the immunogenic composition is administered to the subject via a route selected from intranasal administration, subcutaneous administration, intramuscular administration, intradermal administration, and oral administration.

In some embodiments, at least one subsequent immunologically effective dose of the immunogenic composition is administered to the subject.

In a fourth aspect, the present disclosure provides methods for inducing an effective immune response against Zika virus in a subject, the method comprising expressing a Zika virus nonstructural protein 1 (NS1 protein) in cells of the subject. In some embodiments, the Zika virus NS1 protein has at least 90% amino acid sequence identity with SEQ ID NO: 14. In some embodiments, the Zika virus NS1 protein comprises an amino acid sequence according to SEQ ID NO: 14.

In some embodiments, methods for inducing an effective immune response against Zika virus in a subject further comprise co-expressing a Zika virus envelope (E) protein or a truncation mutant thereof, and a Zika virus premembrane (prM) protein.

In some embodiments, the Zika virus E protein has at least 90% amino acid sequence identity with SEQ ID NO: 4; the Zika virus E protein truncation mutant has at least 90% amino acid sequence identity with one of SEQ ID NO 10 (E404), SEQ ID NO: 8 (E414), or SEQ ID NO: 6 (E415); and the Zika virus prM protein has at least 90% amino acid sequence identity with SEQ ID NO: 12.

In some embodiments, the Zika virus protein(s) are expressed from a recombinant vesicular stomatitis virus (VSV) vector.

In a fifth aspect, the present disclosure provides expression cassettes comprising a promoter operably linked to a polynucleotide encoding a Zika virus nonstructural protein 1 (NS1 protein).

In some embodiments, the polynucleotide encoding the Zika virus NS1 protein further encodes a Zika virus envelope (E) protein or a truncation mutant thereof, and a Zika virus premembrane (prM) protein. In some embodiments, the Zika virus NS1 protein has at least 90% amino acid sequence identity with SEQ ID NO: 14, the Zika virus E protein has at least 90% amino acid sequence identity with SEQ ID NO: 4, the Zika virus E protein truncation mutant has at least 90% sequence identity with one of SEQ ID NO 10 (E404), SEQ ID NO: 8 (E414), or SEQ ID NO: 6 (E415), and the Zika virus prM protein has at least 90% amino acid sequence identity with SEQ ID NO: 12.

BRIEF DESCRIPTION OF THE DRAWINGS

FIG. 1A is an illustration of the Zika virus genome and the strategy employed to construct recombinant VSV expressing ZIKV antigens.

FIG. 1B is a series of representative photographs depicting the plaque morphology of recombinant VSVs (rVSVs) expressing ZIKV antigens.

FIG. 4F is a representative digital photograph of Western blots illustrating the kinetics of ZIKV NS1-specific antibody induced by mtdVSV expressing ZIKV antigen.

FIG. 5 is a representative line graph illustrating the dynamics of mouse body weight following inoculation with the indicated rVSV vectors expressing ZIKV protein subunits.

FIG. 6 is a representative line graph depicting the kinetics of ZIKV-specific ELISA antibody induced by the indicated recombinant VSV vectors expressing ZIKV protein subunits.

FIG. 7A is a series of representative photographs depicting the plaque morphology of MTase-defective recombinant VSV (mtdVSV) vector expressing the indicated ZIKV protein subunits.

FIG. 7B is a representative line graph depicting the single-step growth curve of mtdVSVs expressing the indicated ZIKV protein subunits.

FIG. 7C are representative digital photographs of Western blots illustrating expression of ZIKV E protein by the indicated mtdVSV vectors.

FIG. 7D is a series of representative digital photographs of Western blots illustrating the kinetics of ZIKV E protein expression from the indicated mtdVSV vectors.

FIG. 7E is a representative digital photograph of a Western blot illustrating the release of ZIKV NS1 protein into cell culture supernatant.

FIG. 8A is a representative line graph illustrating the dynamics of mouse body weight following inoculation with the indicated mtdVSV vector.

FIG. 8B is a representative line graph illustrating the kinetics of ZIKV-specific antibody induced by the indicated mtdVSV vectors expressing ZIKV protein subunits.

FIGS. 8C & 8D are representative dot plots illustrating levels of ZIKV-specific neutralizing antibody titer at week 5 post-inoculation with the indicated mtdVSV vector (FIG. 8C) or ZIKV NS1-specific antibody detected by ELISA following inoculation with the indicated mtdVSV vector (FIG. 8D).

FIGS. 9A-9E are representative bar graphs illustrating that MTase-defective rVSV-based vectors induce ZIKV-specific T helper cell responses. The representative bar graphs illustrate proliferation of CD4+ T cells (CD4$^+$CD3$^+$) (FIG. 9A), and the frequencies of ZIKV-specific Th1 cells (IFN-$\gamma^+$CD4$^+$ and TNF-$\alpha^+$CD4$^+$) (FIG. 9B), Th2 cells (IL-4$^+$CD4$^+$, IL-5$^+$CD4$^+$, IL-10$^+$CD4$^+$) (FIG. 9C), Th17 cells (IL-17A$^+$CD4$^+$) (FIG. 9D), and Tfh cells (IL-21$^+$CD4$^+$) (FIG. 9E). Data are expressed as mean % positive cells (the mean of 15 samples: 3 wells×5 mice)±SD. *indicates that the group was statistically different with unstimulated and DMEM groups (p 0.05). P value in from left to right for each panel: (A) **P=3.55×10-9, P=4.10×10-6, P=4.21×10-7. (B) P=0.00676, P=0.00394, P=7.58×10-6, **P=3.32×10-5. (C) *P=0.0243, **P=0.00180, *P=0.0304, *P=0.0149, *P=0.000409, **P=7.72×10-6, *P=0.0102. (D)P=0.00749, P=2.52×10-6, *P=0.000907. (E) *P=0.000313, *P=0.000162.

FIG. 12A is a representative line graph illustrating the dynamic of viremia in unimmunized mice following challenge with ZIKV Cambodian strain. Data were analyzed using one-way multiple comparisons and compared to the placebo DMEM group (****p<0.0001; N.S. indicates not significant).

FIG. 12B is a representative dot plot illustrating the protective effects of MTase-defective rVSV vectors expressing the indicated ZIKV protein subunits in BALB/c mice as measured by viremia.

FIG. 13 is a representative line graph illustrating the dynamics of body weight changes of A129 mice following inoculation with the indicated vectors.

FIGS. 14A-14G are representative dot plots illustrating the ability of MTase-defective rVSV vectors expressing the indicated ZIKV protein subunits to induce ZIKV-specific antibody in A129 mice. ZIKV E protein-specific antibody was measured by ELISA at week 1 (FIG. 14A) and at week 3 (FIG. 14B) post-immunization. ZIKV-specific neutralizing Ab was measured at week 1 (FIG. 14C) and at week 3 (FIG. 14D) post-immunization. ZIKV NS1 protein-specific Ab was measured by ELISA at week 1 (FIG. 14E) and at week 3 (FIG. 14F) post-immunization. Exact P value in each panel: (A) **P=1.36×10-6; (C)P=5.44×10-5; (F)P=6.70×10-5; (G)**P=4.32×10-6, N.S.=not significant.

FIG. 15A is a representative dot plot illustrating the clinical scores of A129 mice inoculated with the indicated vector, after ZIKV challenge.

FIG. 15B is a representative line graph illustrating weight change in A129 mice inoculated with the indicated vector, after ZIKV challenge.

FIG. 15C is a representative line graph illustrating the body weight change for individual A129 mice inoculated with the pCI-NS1 vector.

FIG. 15D is a representative photograph of a Western blot illustrating the expression of ZIKV NS1 protein by rVSV-G1670A and pCI vectors in BSRT7 cells.

FIG. 15E is a line graph illustrating the NS1-specific antibody response in BALB/c mice. P value from top to bottom: **P=3.95×10-5, P=3.48×10-5, P=1.51×10-5, P=0.00183.

FIG. 15F is a line graph illustrating the E-specific antibody response in BALB/c mice.

FIG. 15G is a dot plot illustrating that NS1 alone provided partial protection against viremia in BALB/c mice at day 3 post-challenge. P value from top to bottom: **P=4.15×10-6, *P=0.000161, *P=0.000767, *P=0.000187, *P=0.0250.

FIGS. 16A-16F are representative dot plots illustrating the ability of MTase-defective rVSV vectors expressing the indicated ZIKV protein subunits to protect A129 mice from viremia following ZIKV challenge and prevent ZIKV replication in vivo. Mice were inoculated with the indicated vectors and subjected to ZIKV challenge. After ZIKV challenge, the level of viremia was measured at day 3 (FIG. 16A) and at day 7 (FIG. 16B) post-challenge. At day 7 post-challenge, all mice were terminated, brain (FIG. 16C), lung (FIG. 16D), spleen (FIG. 16E), and uterus/ovary (FIG. 16F) tissues were harvested and analyzed for ZIKV RNA. Data were analyzed using one-way multiple comparisons and compared to the placebo DMEM group or the pCI group (*p<0.05; p<0.01; *p<0.001; ****p<0.0001; N.S., not significant).

FIG. 17 is a series of photographs illustrating the ability of the indicated vectors to prevent ZIKV-induced encephalitis in A129 mice.

FIG. 19A is a line graph illustrating the dynamics of viremia in unimmunized mice after challenge with ZIKV.

FIG. 19B is a dot plot illustrating the quantification of VSV RNA in the brains of BALB/c mice. Data were expressed together with the GMT of 10 mice (black bars). P value from top to bottom: **P=4.25×10-7, *P=0.000710, ***P=0.000371.

FIG. 19C is a line graph illustrating the kinetics of ZIKV E-specific antibody induced by mtdVSV expressing ZIKV antigen. Data are expressed as the GMT of five mice □ standard deviation.

FIG. 19D is a line graph illustrating the kinetics of ZIKV NS1-specific antibody induced by mtdVSV expressing ZIKV antigen.

FIG. 19E is a dot plot illustrating the ability of mtdVSV-based vaccine to protect BALB/c mice from viremia at day 3 post-challenge. P value from top to bottom: **P=1.02× 10-5, P=6.06×10-5, P=0.00345, ***P=0.00310

FIG. 19F is a dot plot illustrating the ability of mtdVSV-based vaccine to protect BALB/c mice from viremia at day 7 post-challenge. P value from top to bottom: ***P=3.89× 10-5, *P=0.0201. Significance was calculated using t-test. N.S. indicates not significant.

FIG. 20A is a line graph illustrating weight loss in A129 mice immunized intramuscularly with rVSV-prM-E-NS1.

FIG. 20B is a dot plot illustrating ZIKV E-specific antibody in A129 at week 4 post immunization with rVSV-prM-E-NS1 in A129 mice.

FIG. 20C is a dot plot illustrating ZIKV NS1-specific antibody in A129 at week 4 post immunization with rVSV-prM-E-NS1 in A129 mice.

FIG. 20D is a line graph illustrating weight loss following challenge with ZIKV in A129 mice immunized intramuscularly with rVSV-prM-E-NS1.

FIG. 20E is a line graph illustrating viremia following challenge with ZIKV in A129 mice immunized intramuscularly with rVSV-prM-E-NS1.

FIG. 21 is an illustration of the VSV genome and the strategy employed to construct G1670A MTase-defective rVSV (mtd-rVSV) expressing ZIKV antigens.

FIG. 22 is a line graph illustrating the dynamics of body weight change of BALB/c mice after immunization with mtdVSV-based vaccine candidates.

FIG. 23 is a line graph illustrating the dynamics of body weight change of immunized BALB/c mice after challenge with ZIKV.

FIG. 24 is an illustration of the VSV genome and the strategy employed to construct D1762 MTase-defective rVSV (mtd-rVSV) expressing ZIKV NS1.

FIG. 25A is a dot plot illustrating viremia (RNA copies) in mice on day 3 post-challenge.

FIG. 25B is a dot plot illustrating viremia (RNA copies) in mice on day 7 post-challenge.

FIG. 25C is a dot plot illustrating viremia (PFU) in mice on day 3 post-challenge.

FIG. 25D is a dot plot illustrating viremia (PFU) in mice on day 7 post-challenge.

FIG. 26A is a line graph illustrating the dynamics of mouse body weight change after vaccination with rVSV-D1762A-483-NS1.

FIG. 26B is a line graph illustrating the kinetics of ZIKV NS1-specific antibody induced by rVSV-D1762A-483-NS1.

FIG. 26C is a line graph illustrating body weight changes after ZIKV challenge.

FIG. 26D is a line graph illustrating body weight change of each mouse after ZIKV challenge.

FIG. 26E is a survival curve of A129 mice after ZIKV challenge.

FIG. 26F is a dot plot illustrating viremia in A129 mice on day 3 after challenge with ZIKV.

DEFINITIONS

Figure 2:
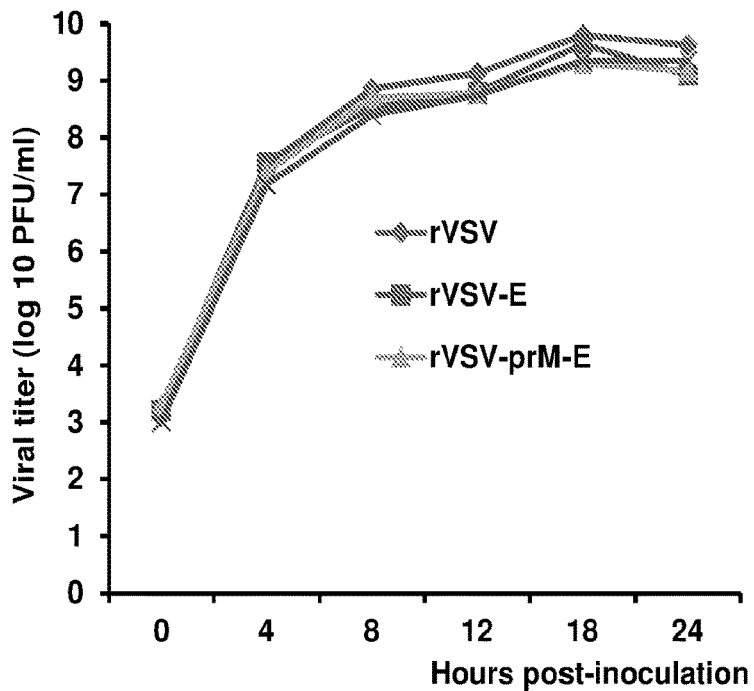
FIG. 2 is a representative line graph illustrating the single-step growth curves of the indicated rVSV vectors.

An "immunogenic composition" refers to any mixture, aqueous solution, non-aqueous solution, suspension, emulsion, gel, or the like, containing a recombinant vector provided by the present disclosure and at least one other component. Other components can be, for example, one or more pharmaceutical agents, carriers, vehicles, excipients, or a combination thereof. Generally, immunogenic compositions can be prepared by uniformly combining the recombinant vector with a liquid carrier, vehicle, or excipient, or a finely divided solid carrier, vehicle, or excipient, or combination thereof. An immunogenic composition includes enough recombinant vector to produce an effective immune response. Accordingly, the immunogenic compositions described herein encompass any composition made by admixing a compound of recombinant vector described herein and a pharmaceutically acceptable carrier, vehicle, or excipient. By "pharmaceutically acceptable" it is meant that the carrier, vehicle, or excipient is approved, or approvable, by a regulatory body such as the FDA and/or is capable of being incorporated into a human pharmaceutical therapeutic.

As used herein, the term "effective immune response" refers to an immune response that confers immunity against an infection, reduces the probability of infection recurrence, confers maternal immunity to an offspring, or prevents development of disease resulting from an infection. For instance, an immune response is considered to be an "effective immune response" if it is sufficient to prevent a subject or an offspring of a subject from developing a Zika virus infection after administration of or exposure to a challenge dose of Zika virus. An effective immune response can include a cell mediated immune response, and/or a humoral immune response. An immune response is also considered to be an "effective immune response" if it is sufficient to prevent Zika disease in a subject infected with Zika virus; although Zika infection may present, an effective immune response prevents development of Zika disease in the subject.

The term "immunologically effective dose" refers to an amount of a vaccine or immunogenic composition provided by the present disclosure sufficient to cause an effective immune response. The immunologically effective dose can be administered in one or more administrations. The precise determination of what would be considered an immunologically effective dose can be based on factors individual to each subject, including but not limited to the subject's age, size, and route of administration, as well as the judgment of the prescribing physician.

DETAILED DESCRIPTION

In the following sections, various compositions and methods are described in order to detail various embodiments. Practicing the various embodiments does not require the employment of all of the specific details outlined herein, but rather concentrations, time, and other specific details may be modified. In some cases, well known methods or components have not been included in the description It is described herein for the first time that inoculation of a subject with a Zika virus (ZIKV) nonstructural protein 1 (NS1 protein) antigen provides partial protection against ZIKV challenge. Embodiments disclosed herein provide compositions, methods, and uses for recombinant vectors encoding ZIKV protein subunits, and immunogenic compositions thereof. Certain embodiments provide recombinant vectors encoding ZIKV NS1 protein, or variants thereof, and optionally, ZIKV envelope (E) protein, or variants thereof, and/or premembrane (prM) protein, or variants thereof. Other embodiments provide expression cassettes comprising a promoter operably linked to a polynucleotide that encodes the ZIKV NS1 protein, and optionally ZIKV E and prM proteins. In some embodiments, the disclosed expression cassettes can be incorporated into a vector to produce a recombinant vector. Also provided are immunogenic compositions comprising one or more recombinant vectors described herein, and methods for inducing an immune response against ZIKV in a subject comprising administering to the subject an immunologically effective dose of an immunogenic composition of the present disclosure.

Current efforts to develop ZIKV subunit vaccines have been exclusively focused on prM and E proteins which rely on generating high levels of neutralizing Ab. However, it has been reported that Abs generated against one flavivirus can cross-react with other species of flavivirus without neutralizing them, which may facilitate infection by the second flavivirus in cells expressing Fc receptors. This process is called Antibody Dependent Enhancement (ADE). Additional ZIKV subunit vaccines are needed.

Certain embodiments provide recombinant vectors encoding ZIKV protein subunits. Similarly to all other flaviviruses, such as dengue virus, yellow fever virus, West Nile virus, Japanese encephalitis virus, and tick-borne encephalitis virus, the ZIKV genome encodes a single polyprotein that is cleaved posttranslationally by host and viral proteases into three structural proteins (capsid (C), premembrane (prM), and envelope (E)) and seven nonstructural proteins (NS1, NS2A, NS2B, NS3, NS4A, NS4B, and NS5). In some embodiments, a recombinant vector encodes ZIKV NS1. In some embodiments, the recombinant vector comprises a polynucleotide sequence that encodes the ZIKV NS1 protein. In certain embodiments, the recombinant vector encoding ZIKV NS1 can further encode ZIKV E and prM proteins. In such embodiments, a continuous polynucleotide sequence can encode all three of the ZIKV E, prM, and NS1 proteins, or each of the proteins can be encoded by a distinct polynucleotide.

The E protein is a type II fusion protein, which mediates cellular attachment and membrane fusion, and is the target for most neutralizing antibodies (Abs). Flavivirus prM protein typically associates with E protein to form heterodimers and is important for proper folding of E protein. Co-expression of prM and E of several flaviviruses including ZIKV results in the secretion of virus-like particles (VLPs) termed recombinant subviral particles, which have structural and functional features of the virion envelope. Flavivirus NS1 has been implicated in various functions, including genome replication and immune evasion.

In some embodiments, the E protein encoded by the recombinant vector can be a full-length E protein (504 amino acids; SEQ ID NO: 4), or a truncated mutant thereof. In some embodiments, the truncated mutant can be a protein having the N-terminal 404 amino acids of the full-length E protein (SEQ ID NO: 10), the N-terminal 414 amino acids of the full-length E protein (SEQ ID NO: 8), or the N-terminal 415 amino acids of the full-length E protein (SEQ ID NO: 6).

In certain embodiments, the NS1 protein encoded by the recombinant vector has an amino acid sequence having at least 90% sequence identity with the NS1 protein of ZIKV Cambodian strain (FSS13025) (SEQ ID NO: 14). In some embodiments, the ZIKV E protein encoded by the recombinant vector has an amino acid sequence having at least 90% sequence identity with the E protein of ZIKV Cambodian strain (FSS13025) (SEQ ID NO: 4). In those embodiments where the recombinant vector encodes a truncated E protein mutant, the truncated protein can have at least 90% sequence identity with the N-terminal 404 amino acids of the full-length E protein (SEQ ID NO: 10), the N-terminal 414 amino acids of the full-length E protein (SEQ ID NO: 8), or the N-terminal 415 amino acids of the full-length E protein (SEQ ID NO: 6). In some embodiments, the ZIKV prM protein encoded by the recombinant vector has an amino acid sequence having at least 90% sequence identity with the prM protein of ZIKV Cambodian strain (FSS13025) (SEQ ID NO: 12). While the sequences of the ZIKV Cambodian strain (FSS13025) are provided here, the sequences of other ZIKV strains and their NS1, E, and prM proteins are known and can be similarly used to construct a recombinant vector, or construct, as described herein. The full nucleic acid sequence of ZIKV Cambodian strain (FSS13025) is provided by SEQ ID NO: 1, and the amino acid sequence is provided by SEQ ID NO: 2.

In some embodiments, where the recombinant vector encodes only the ZIKV NS1 protein, expression of NS1 alone can provide at least partial protection against ZIKV challenge, without inducing neutralizing antibody. In other embodiments, where the recombinant vector encodes ZIKV NS1, E, and prM proteins, the three ZIKV proteins can be expressed from the recombinant vector as a single polyprotein—e.g., as a prM-E-NS1 polyprotein. This prM-E-NS1 polyprotein can be cleaved posttranslationally by host and viral proteases into the three distinct proteins: prM, E, and NS1. When expressed together, the ZIKV E, prM, and NS1 proteins can provide complete protection against ZIKV challenge.

Other embodiments provide expression cassettes comprising an open reading frame (ORF) polynucleotide sequence encoding a ZIKV NS1 protein. In some embodiments, the ORF polynucleotide sequence also encodes ZIKV E protein and ZIKV prM protein.

In some embodiments, the ORF polynucleotide sequence of the expression cassette is operably linked to one or more control elements compatible with expression in a selected vector. In some embodiments, the expression cassette comprises a polyadenylation site. In certain embodiments, the expression cassette can be inserted into a vector and can be expressed therefrom. In some embodiments, the one or more control elements comprise at least one promoter.

Vectors useful as backbones for the recombinant vectors described herein can be any vector suitable for expression in a chosen system. For example, where it is an aim to express ZIKV protein subunits in vitro, an appropriate plasmid, viral vector, bacterial vector, insect vector, baculovirus expression vector, yeast vector, mammalian cell vector, or the like, can be selected. Suitable vectors can be identified by the skilled artisan taking into consideration the characteristics for expressing the ZIKV protein subunits under the desired conditions.

Where it is an aim to express the ZIKV protein subunits in vivo in a subject, for example in order to generate an effective immune response against a ZIKV antigen, elicit protective immunity against ZIKV, and/or prevent development of Zika disease in an infected subject, vectors that are safe for use and suitable for expression in that subject should be chosen. In some embodiments, the vector is selected from adenovirus, adeno-associated virus (AAV), retrovirus, lentivirus, vaccinia virus, cytomegalovirus, Sendai virus, modified vaccinia Ankara virus, and vesicular stomatitis virus (VSV). Such viruses, when used as expression vectors, can be innately non-pathogenic in the target subjects, or can be modified to render them non-pathogenic in the target subjects.

In some embodiments, the vector is vesicular stomatitis virus (VSV). VSV is a prototypical nonsegmented negative-sense (NNS) RNA virus that belongs to the Rhabdoviridae family. VSV is a natural pathogen of livestock such as cattle and swine. As such, there is no pre-existing immunity against VSV in the human population. VSV is an RNA virus and it does not undergo either recombination or integration into host cell DNA. VSV also grows to a high titer in a wide range of mammalian cells, an important feature for vaccine manufacturing. Thus, VSV is an excellent platform for vaccine development. VSV can accommodate multiple foreign genes, and antigens are highly expressed in both cell culture and animals by VSV, enabling the generation of strong systemic immune responses.

In response to the sudden outbreaks of Ebola virus in Africa in 2013, a VSV-based Ebola virus vaccine was tested in human clinical trials. The VSV-based Ebola virus vaccine was shown to be highly efficacious in protecting against Ebola virus infection in humans. Currently, at least 15 independent human clinical trials are ongoing worldwide to test the efficacy of VSV-based vaccine candidates and to utilize VSV as an oncolytic agent for cancer therapy. In general, VSV is safe in humans, although high doses of VSV can cause side effects in some people including joint and muscle pain.

Figures 1A, 1B:
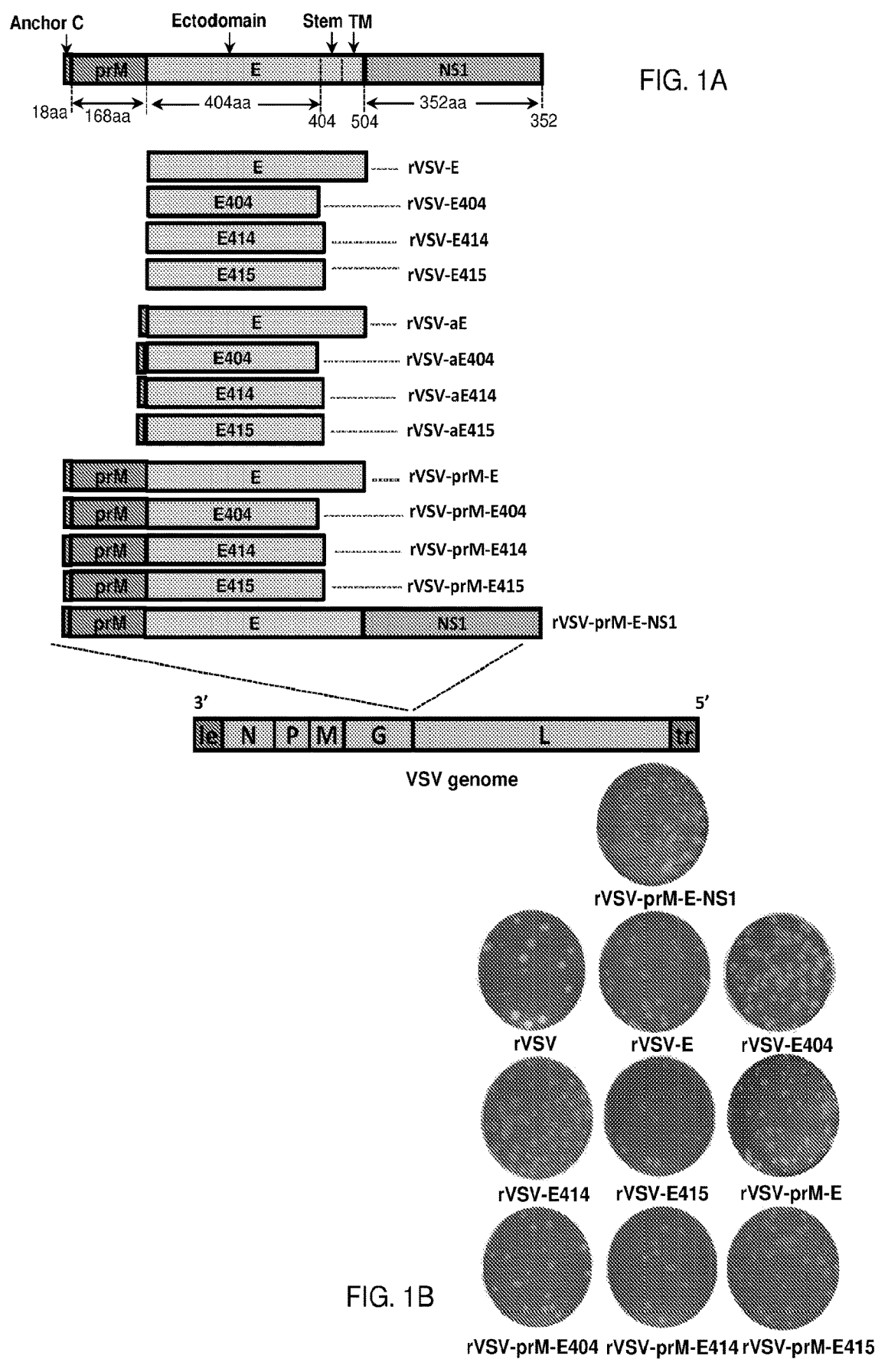

In certain embodiments, a polynucleotide sequence encoding ZIKV NS1 protein can be incorporated into VSV, thereby producing a recombinant VSV (rVSV) that encodes ZIKV NS1 (rVSV-NS1). Of course, other ZIKV protein encoding rVSVs can also be constructed. As described in Example 1, thirteen recombinant viruses using the wild-type VSV genome as the backbone were constructed. As depicted in the top panel of FIG. 1, the positive-sense genome of ZIKV encodes a polyprotein which is proteolytically cleaved into 10 viral proteins including capsid (C), pre-membrane (prM), envelope (E), nonstructural protein 1 (NS1), NS2A, NS2B, NS3, NS4A, NS4B, and NS5. The middle panel of FIG. 1 illustrates expression cassettes comprising full-length ZIKV E, E truncations (E404, E414, and E415) lacking transmembrane domain, prM-E, prM-E truncations (prM-E404, prM-E414, and prM-E415), and prM-E-NS1. These genes were amplified from an infectious cDNA clone of ZIKV Cambodian strain by PCR, digested by XhoI and SmaI, and inserted into the same sites at the gene junction between G and L proteins in the VSV genome. The organization of the nonsegmented negative-sense VSV genome is depicted in the bottom panel of FIG. 1A (le=VSV leader sequence; N=nucleocapsid gene; P=phosphoprotein gene; M=matrix protein gene; G=glycoprotein gene; L=large polymerase gene; tr=VSV trailer sequence).

In some embodiments, the VSV vector is pVSV1(+) (SEQ ID NO: 15) or pVSV1(+)-GxxL (SEQ ID NO: 16).

In certain embodiments, the recombinant VSV vector encodes ZIKV E, prM, and NS1 proteins (rVSV-E-prM-NS1). As depicted in FIG. 2, rVSV-E-prM-NS1, along with the other recombinant vectors tested, grew to high titer in cell culture and had similar, but slightly lower, virus replication kinetics compared to parental rVSV.

Figures 4A, 4B, 4C:
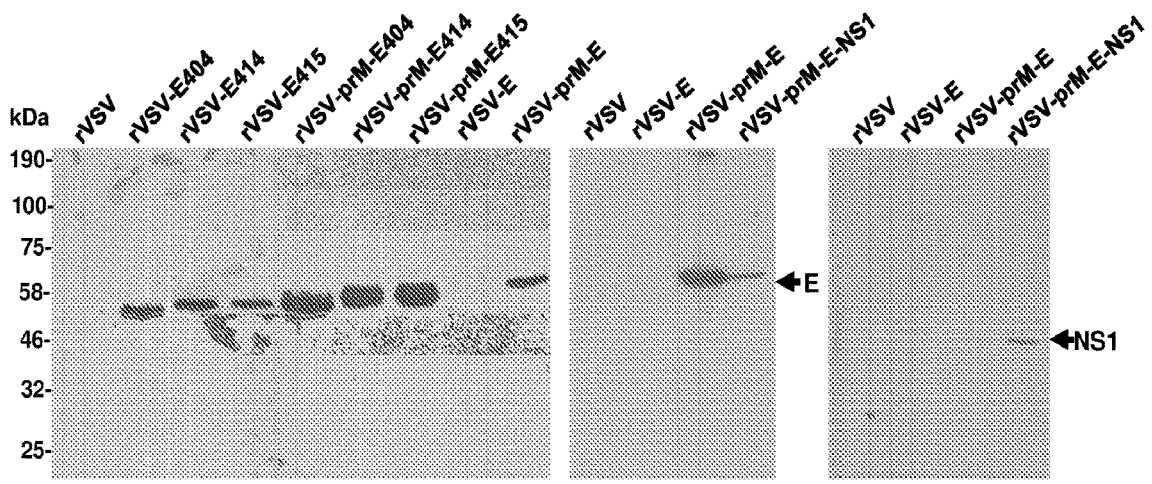
FIGS. 4A-4C are representative digital photographs of Western blots illustrating expression of ZIKV E protein truncations by VSV vector (FIG. 4A), expression of full-length ZIKV E protein by VSV vector (FIG. 4B), and expression of ZIKV NS1 protein by VSV vector (FIG. 4C).
Figure 4D:
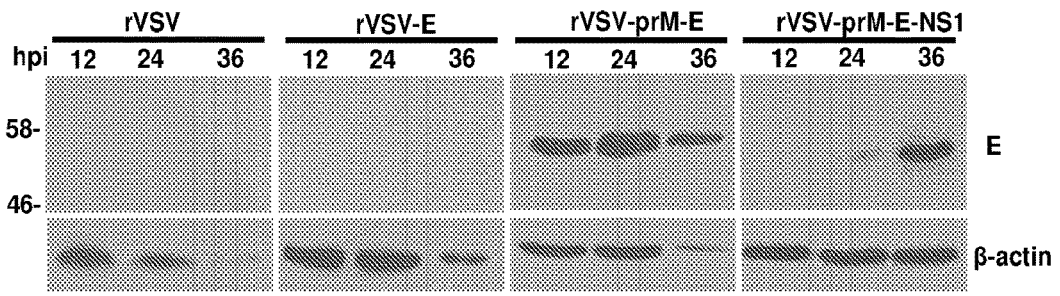
FIG. 4D is a series of representative digital photographs of Western blots illustrating the kinetics of ZIKV E protein expression by VSV vectors encoding the indicated ZIKV protein subunits.
Figure 4E:
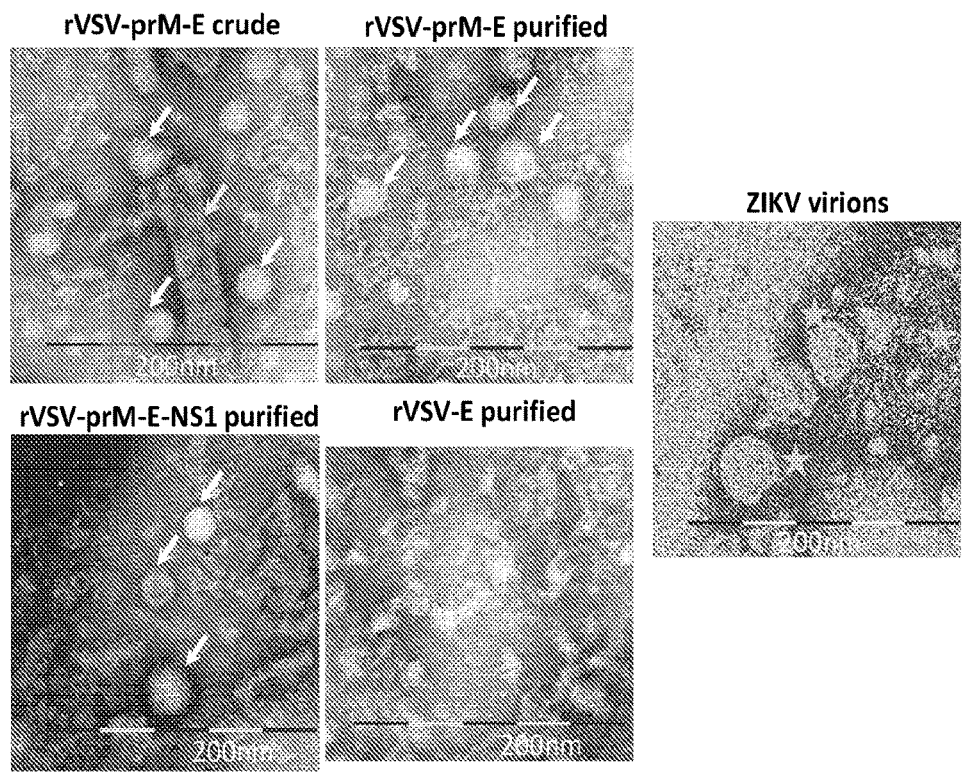
FIG. 4E is a series of representative electron micrographs depicting ZIKV virus-like particles (VLPs) resulting from expression of ZIKV protein subunits from the indicated recombinant VSV vectors.

The ZIKV E, prM, and NS1 proteins expressed from rVSV-E-prM-NS1 produced virus-like particles (VLPs) that are structurally similar to native ZIKV virions (see, FIG. 4E and Example 3).

In certain embodiments, inclusion of one or more ZIKV protein subunit-encoding polynucleotide sequences can attenuate the host viral vector. As described in Example 4, rVSVs co-expressing prM and E protein, or truncated E protein mutants, were more attenuated in mice that rVSV expressing E protein or truncated E protein mutants alone. Recombinant rVSV-E-prM-NS1 was the most attenuated virus of those tested. Mice inoculated with rVSV-E-prM-NS1 experienced little or no weight loss and did not display any other clinical signs. A single dose inoculation of mice with rVSV-E-prM-NS1 resulted in high levels of serum antibody response as early as 1 to 2 weeks post-inoculation (see Example 4).

In certain embodiments, and as described above, ZIKV NS1 can be expressed from any appropriate vector. The vector backbone need not be VSV. In some embodiments, the vector can be a DNA vector. For example, a polynucleotide encoding ZIKV NS1 can be incorporated into a DNA vector such as pCI. As described in Example 10, A129 mice inoculated with a pCI-NS1 recombinant vector were partially protected from ZIKV challenge, even in the absence of detectable ZIKV neutralizing antibody (see Example 10). In some embodiments, a non-VSV recombinant vector encodes ZIKV NS1, and optionally, ZIKV E and prM.

In certain embodiments, partial protection is an effective immune response. In embodiments where NS1 is presented alone, i.e., in the absence of prM and/or E protein (or truncations thereof), an effective immune response may prevent development of Zika disease in a subject, despite the subject being infected with Zika virus. An immunogenic composition comprising NS1 alone or expressing NS1 alone would avoid Antibody Dependent Enhancement issues experienced by ZIKV subunit vaccines expressing ZIKV prM and/or E protein.

Certain embodiments provide a modified, highly attenuated VSV backbone. In some embodiments, the VSV large (L) polymerase protein comprises at least one mutation in the S-Adenosyl methionine (SAM) binding site in the methyltransferase-encoding region. In some embodiments, the VSV L protein is mutated at at least one amino acid position selected from K1651, G1670, D1762, K1795, and E1833. In some embodiments, the VSV L protein is mutated at G1670, G1762, or both G1670 and G1762. The mutation(s) can be any mutation(s) that result(s) in defective mRNA cap guanine-N-7 methylation. In certain embodiments, the mutation is a G1670A mutation, a G1762A mutation, or both G1670A and G1762A mutations.

In some embodiments, the ZIKV protein subunit-expressing recombinant VSVs described herein comprise at least one attenuating mutation in the VSV L protein. In some embodiments, the at least one attenuating mutation comprises G1670A and/or G1762A. As described throughout the Examples, rVSV-G1670A and rVSV-G1762A vectors were highly attenuated in both BALB/c and A129 mice. ZIKV proteins, including ZIKV E and NS1 are highly expressed by the MTase-defective rVSV-G1670A (e.g., from rVSV-G1670A-prM-E and rVSV-G1670A-prM-E-NS1). Single doses of the highly attenuated rVSV-G1670A-prM-E-NS1 were observed to protect BALB/C and A129 mice from ZIKV viremia (see Examples 8 and 9). Similar results were observed with rVSV-G1762A serving as the VSV backbone (see Example 13).

In other embodiments, the recombinant vectors described herein can be formulated into an immunogenic composition against ZIKV. In some embodiments, the immunogenic composition against ZIKV can be a pharmaceutical composition, such as a vaccine.

In certain embodiments, the immunogenic composition against ZIKV can include one or more pharmaceutically acceptable carriers, vehicles, excipients, or any combination thereof. Suitable pharmaceutical carriers, vehicles, and excipients for formulating a pharmaceutically acceptable immunogenic compound, including vaccines, are known in the art. In some embodiments, the immunogenic composition can include at least one adjuvant for further induction of the immune system in a subject when administered. In some embodiments, the immunogenic composition can include a nanoparticle delivery system.

Other embodiments provide methods for inducing an effective immune response against ZIKV in a subject. In some embodiments, the methods can include administering an immunologically effective dose of an immunogenic composition against ZIKV described herein to the subject. In other embodiments, the methods can include expressing a ZIKV NS1 protein described herein in cells of a subject. In some embodiments, the methods can further comprise co-expressing ZIKV E and prM proteins in the subject. In some embodiments, the ZIKV protein subunits can be expressed from a recombinant vector described herein.

In certain embodiments, the subject is human. In some embodiments, the subject is human subject that is pregnant, may be pregnant, or is trying to get pregnant. The immunogenic composition against ZIKV can be administered to a subject at risk of acquiring a ZIKV infection, or a subject having a ZIKV infection. Accordingly, certain embodiments provide methods for preventing a ZIKV infection is such a subject comprising administering an immunogenic composition described herein.

In some embodiments, an immunogenic composition against ZIKV can be administered to a patient post-infection, thereby protecting them from subsequent ZIKV infections and/or ameliorating the symptoms from subsequent infections.

In some embodiments, a subject is administered at least one immunologically effective dose subsequent to an initial dose. The immunogenic composition against ZIKV can be administered to the subject once, or can be administered a plurality of times, e.g., one, two, three, four, or five times.

In certain embodiments, immunogenic compositions against ZIKV can be administered to a subject in any manner, including for example, subcutaneously, intravenously, by oral administration, inhalation, intradermally, by transdermal application, intravaginal application, topical application, intranasally, intramuscularly, or by rectal administration. In one embodiment, an immunologically effective dose of an immunogenic composition against ZIKV is administered to a human intranasally. In other embodiments, the route of administration can be intradermal administration or intramuscular administration.

In some embodiments, an immunogenic composition can be administered to a subject in an appropriate pharmaceutically acceptable carrier or diluent, co-administered with enzyme inhibitors, or in an appropriate carrier such as liposomes. As used herein, the term "pharmaceutically acceptable carrier" includes diluents such as saline and aqueous buffer solutions. Dispersions can also be prepared in glycerol, liquid polyethylene glycols, and mixtures thereof and in oils. Under ordinary conditions of storage and use, these preparations may contain a preservative to prevent the growth of microorganisms or other stabilizing formulation.

Pharmaceutical compositions suitable for injectable use can be administered by means known in the art. For example, sterile aqueous solutions (where water soluble) or dispersions and sterile powders for the extemporaneous preparation of sterile injectable solutions or dispersion can be used. In all cases, the composition can be sterile and can be fluid to the extent that easy syringability exists. It can be stable under the conditions of manufacture and storage and can be preserved against the contaminating action of microorganisms such as bacteria and fungi. The pharmaceutically acceptable carrier can be a solvent or dispersion medium containing, for example, water, ethanol, polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of microorganisms can be achieved by heating, exposing the agent to detergent, irradiation or adding various antibacterial or antifungal agents.

Sterile injectable solutions can be prepared by incorporating a vector provided by the present disclosure or a compound comprising the same (e.g. a compound that induces an immune response to ZIKV) in the required amount in an appropriate solvent with one or a combination of ingredients enumerated above, as required, followed by filtered sterilization.

Upon formulation, sterile injectable solutions will be administered in a manner compatible with the dosage formulation and in such amount as is immunologically effective. The formulations are easily administered in a variety of dosage forms, such as the type of injectable solutions described above. It is contemplated that compositions are especially suitable for intramuscular, subcutaneous, intradermal, intranasal and intraperitoneal administration.

In another embodiment, nasal solutions or sprays, aerosols or inhalants can be used to deliver the immunogenic composition of interest. Additional formulations that are suitable for other modes of administration include suppositories and pessaries.

Certain formulations can include excipients, for example, pharmaceutical grades of mannitol, lactose, starch, magnesium stearate, sodium saccharine, cellulose, magnesium carbonate and the like.

A pharmaceutical composition can be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this disclosure, and without departing from the spirit and scope thereof, can make various changes and modifications to the subject matter provided by this disclosure to adapt it to various usages and conditions.

The following examples describe the development of a methyltransferase (MTase)-defective rVSV (mtdVSV)-based ZIKV vaccine platform. A panel of rVSV expressing ZIKV prM-E-NS1, prM-E, E, E truncation mutants, and NS1 was recovered. These mtdVSV-based ZIKV vaccine candidates were highly attenuated but remained effective in triggering ZIKV-specific antibody and T cell immunity in mice, and provided complete protection against ZIKV challenge in immunocompetent BALB/c and type 1 interferon receptor-deficient A129 mice. In addition, the examples demonstrate that NS1 alone can confer partial protection from ZIKV infection.

Example 1—Recovery of Recombinant VSVs Expressing ZIKV Protein Subunits

In one illustrative method, thirteen recombinant viruses were constructed using the wild-type VSV genome as the backbone (FIG. 1A). These constructs allowed for the comparison of the immunogenicity of various combinations of ZIKV wild-type and mutant proteins, all including the E protein, since it is known in other flaviviruses to be the main target for neutralizing antibody (Ab). ZIKV E protein consists of two principal domains, the N-terminal ectodomain containing the major neutralizing epitopes and the C-terminal transmembrane (TM) domain (FIG. 1A). The major neutralizing epitopes are located in the ectodomain of the E protein.

The rVSV-E recombinant virus was constructed first, which expressed the full-length E protein (504 amino acids; SEQ ID NO: 4). Because the exact boundary between the ectodomain and the TM domain is unclear, three E truncation mutants lacking the predicted TM domain were generated and incorporated in three recombinant viruses, rVSV-E404, rVSV-E414, and rVSV-E415 which express the N-terminal 404 (SEQ ID NO: 10), 414 (SEQ ID NO: 8), and 415 (SEQ ID NO: 6) amino acids of the E protein, respectively (FIG. 1A). Four recombinant viruses were constructed that would co-express prM with E, and each of the same E deletions, respectively, as a polyprotein with anchor C (signal peptide) (FIG. 1A). These recombinant viruses were named rVSV-aE, rVSV-aE404, rVSV-aE414, and rVSV-aE415. Also constructed were four recombinant viruses that co-expressed anchor C-prM with E, or the same E deletions, as a polyprotein (FIG. 1A). The recombinant rVSV-prM-E-NS1, which expresses prM, E, and NS1 as a polyprotein, was also constructed. (FIG. 1A)

Plaques formed by rVSV were 3.5±0.8 mm (mean±standard deviation) in diameter, while plaques formed by rVSV expressing ZIKV protein subunits ranged from 2.6±0.6 mm to 3.0±0.6 mm in diameter (FIG. 1B), indicating that expression of these ZIKV proteins reduced the replication and/or cell-to-cell spread of rVSV. Replication kinetics of rVSV, rVSV-E, rVSV-prM-E, and rVSV-prM-E-NS1 were compared in culture. All recombinant viruses grew to high titer in cell culture and had similar but slightly lower virus replication kinetics compared to parental rVSV (FIG. 2), except for rVSV-prM-E-NS1, which had a significant delay in replication kinetics compared to parental rVSV (P<0.05) (FIG. 2). 11381 Recombinant viruses were constructed as described in Example 12.

Example 2—High-Level Expression of ZIKV Proteins by the VSV Vector

Figures 4F, 5, 6:
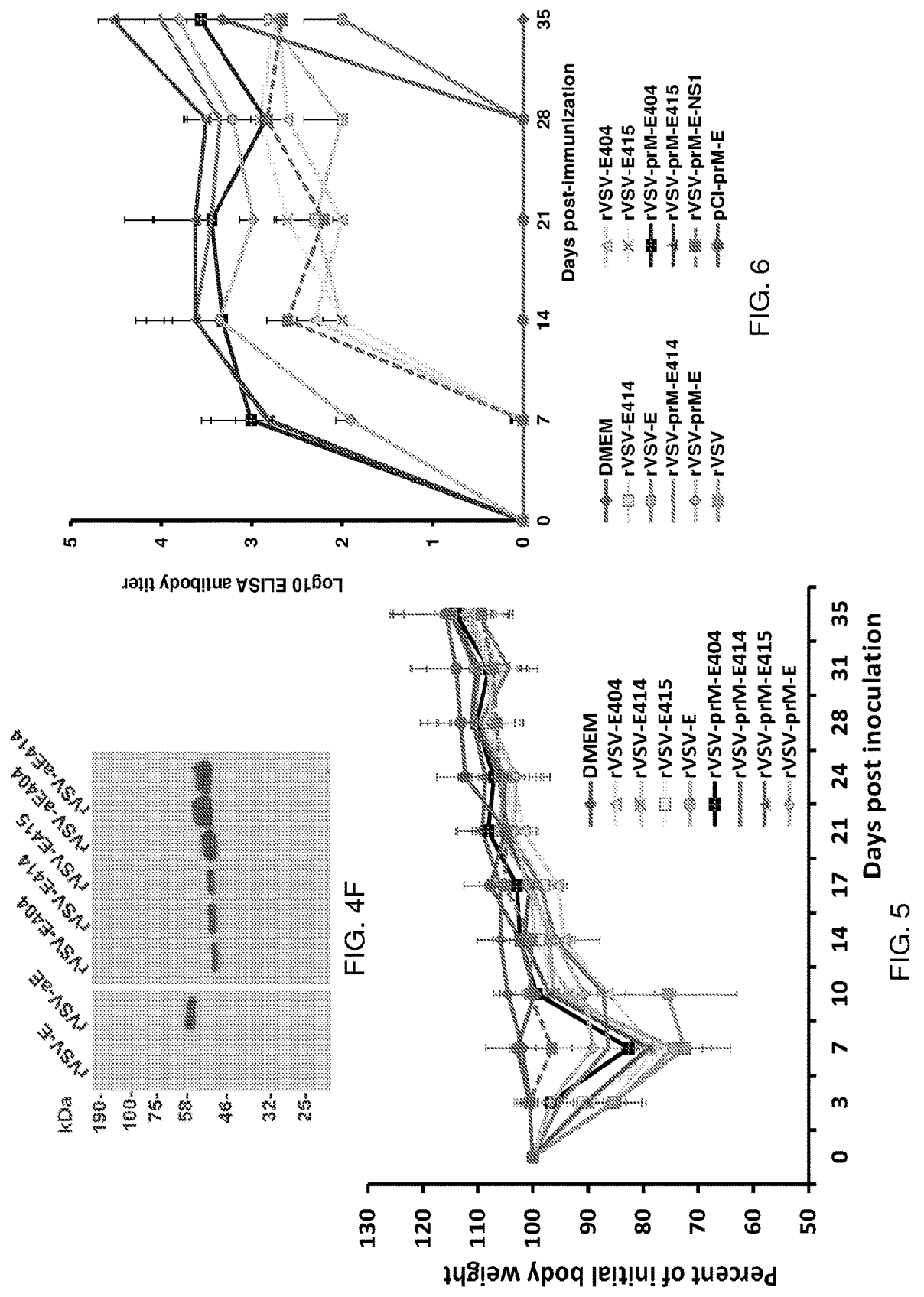

In an illustrative method, the expression levels of VSV-vectored ZIKV E protein and its truncations were assessed in infected cells. A 54 kDa full-length E protein was detected in cells infected with rVSV-prM-E and rVSV-prM-E-NS1 but not with rVSV-E (FIGS. 4A and 4B). The NS1 protein was only detected in rVSV-prM-E-NS1 infected cells (FIG. 4C), as expected. A smaller E protein was detected in cells expressing the truncated E protein, consistent with the shorter C-terminal domain (FIG. 4A). Quantitative analysis of three independent experiments indicated that rVSVs co-expressing prM with E or E truncations had approximately 5 times greater E protein expression compared to rVSVs expressing E or E truncations without prM. At 48 h post-inoculation, cell culture supernatants were harvested and subjected to Western blot. Results demonstrated that all rVSVs co-expressing prM and E/E truncations released enough E/E truncation proteins into the supernatant to be easily detectable without the need for concentration. NS1 protein was also secreted into cell culture medium. However, no E/E truncation was detectable in cell medium from rVSVs expressing E/E truncations alone. The expression level of E/E truncations with or without anchor C signal peptide by VSV vector were compared. As indicated in FIG. 4F, rVSV constructs with anchor C had more abundant expression of E/E truncations compared to rVSV constructs without anchor C. E truncations were also detected in the supernatants of rVSV constructs with anchor C. However, full-length E protein was still not detectable by rVSV-aE, even though the anchor was fused with E. Thus, co-expression of anchor C and prM with the E/E truncations significantly increased their E expression and/or stability. These results also indicate that the prM, E, and NS1 proteins were proteolytically cleaved from the polyprotein and secreted into cell culture supernatants when expressed from a VSV vector.

Figure 3:
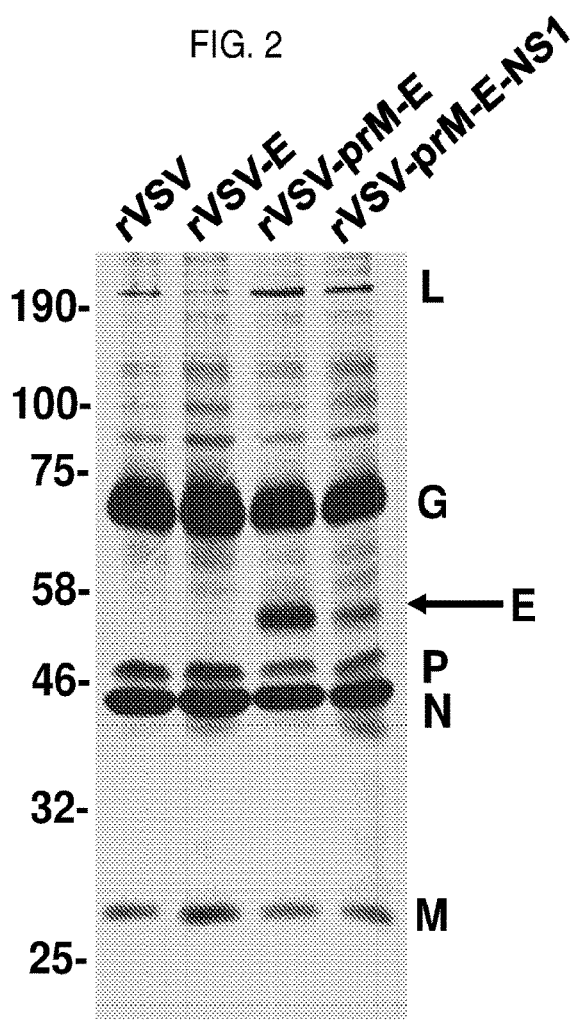
FIG. 3 is a representative photograph of an SDA-PAGE blot illustrating detection of ZIKV E protein expression from the indicated rVSV vectors using [$^{35}$S]methionine labelling.

The kinetics of E protein expression in virus-infected cells were evaluated (FIG. 4D). E protein was detectable in rVSV-prM-E at 12 h post-infection, reached the highest expression level at 24 h post-infection, and declined by 36 h primarily because cells were lysed by this time point, as indicated by the reduction in β-actin. Recombinant rVSV-prM-E-NS1 had a significant delay in E protein expression. E protein was detectable at 24 h and reached its highest level at 36 h post-infection, without cell death as indicated by a continued high level of β-actin. E protein was not detectable in cells infected by rVSV-E even at the time when most cells were lysed. The expression of E protein by rVSV-prM-E and rVSV-prM-E-NS1, but not by rVSV-E in virus-infected cells was confirmed by [$^{35}$S]methionine-cysteine metabolic labeling (FIG. 3).

Example 3—Expression of prM-E or prM-E-NS1 by rVSV Generates Virus-Like Particles In one illustrative method, cells were infected with rVSV-E, rVSV-prM-E or rVSV-prM-E-NS1 and the cell culture medium was harvested at 24-48 h post-infection. Two types of particles, VSV and ZIKV virus-like particles (VLPs), were detected by negative-staining and electron microscopy (FIG. 4E). After separation by CsCl isopycnic gradient centrifugation, a large number of low density ZIKV VLPs were recovered from rVSV-prM-E and rVSV-prM-E-NS1 infected cells (FIG. 4E). The ZIKV VLPs expressed by VSV had a diameter of 30-40 nm, which are relatively smaller than native ZIKV virions (40-50 nm). No VLPs were detected in cell culture media from cells infected with rVSV-E (FIG. 4E. These results confirm that expression of prM-E and prM-E-NS1 but not E alone by the VSV vector resulted in the assembly of VLPs that are structurally similar to native ZIKV virions.

Example 4—rVSV-prM-E/E Truncations Induce More Antibody than rVSV-E/E Truncations In one illustrative method, BALB/c mice were inoculated intranasally with a single dose ($10^6$ PFU) of each of nine recombinant virus. A DNA vaccine (pCI plasmid encoding ZIKV prM and E; pCI-prM-E) was used as a control. Mice were intramuscularly injected with 50 µg of pCI-prM-E and were boosted with same dose of pCI-prM-E two weeks later. Mice infected with rVSV exhibited severe clinical signs, including ataxia, hyperexcitability, and paralysis. At 7 days post-inoculation, two of the five mice were dead, and the remaining three mice were dead at day 10 post-inoculation.

rVSVs expressing ZIKV protein subunits showed various degrees of attenuation. Mice inoculated with these recombinant viruses had mild clinical signs (such as a ruffled coat) and experienced body weight losses for 1 week, but started to gain weight by 10 days (FIG. 5). Overall, rVSVs co-expressing prM and E/E truncation mutants were more attenuated in mice than rVSV expressing E/E truncation alone. rVSV-prM-E and rVSV-prM-E414 had significantly less body weight loss compared to rVSV-E (P=0.021) and rVSV-E414 (P=0.045) respectively at day 7 post-inoculation.

Recombinant rVSV-prM-E-NS1 was the most attenuated virus (FIG. 5). Mice inoculated with this virus experienced little or no weight loss and did not display any other clinical signs. This experiment demonstrated that rVSV expressing ZIKV antigens, particularly rVSV-prM-E-NS1, were significantly attenuated in mice compared to the parental rVSV.

The dynamics of ZIKV E-specific Ab production following vaccination, determined by ELISA, is summarized in FIG. 6. At 1-week post-inoculation, most (3 or 4 out of 5) mice inoculated with rVSV co-expressing prM-E/E truncation mutants had high levels of serum IgG against ZIKV E protein. At week 2 post-inoculation, all mice in these groups had developed IgG Ab. Ab titers further increased and remained at a high level through week 5. In contrast, none of the mice vaccinated with rVSV expressing E/E truncation mutants without prM had detectable ZIKV-specific antibody by week 1. The same was true for rVSV-prM-E-NS1. At week 2, Ab was observed in these groups and increased through week 5. However, the Ab titers in these groups were significantly lower than those of the viruses co-expressing prM-E/E truncation mutants only (P<0.05).

Ab was not detectable in the DNA vaccine group until week 5, despite the fact that these mice had been given two doses. The Ab detected in the DNA vaccine group at week 5 post-immunization was also lower than that induced by the rVSV-prM-E/E truncations. These results demonstrate that a single-dose inoculation of mice with rVSV co-expressing prM-E/E truncations or prM-E-NS1 triggered high levels of serum antibody response as early as 1 to 2 weeks post-inoculation.

Example 5—Attenuation of Recombinant VSV Expressing ZIKV Protein Subunits

In one illustrative method, VSV was further attenuated to enhance VSV as a vector by a specific mutation that inhibits its mRNA cap methyltransferase (MTase) activity. A single point mutation (G16870) in the S-Adenosyl methionine (SAM) binding site in the MTase region of the large (L) polymerase protein was previously demonstrated to result in a recombinant virus (rVSV-G1670A) that was defective in mRNA cap guanine-N-7 methylation but not ribose 2'-O methylation (see Li et al., 2006. Proceedings of the National Academy of Sciences of the United States of America 103:8493-8498). Compared to rVSV, this recombinant virus was highly attenuated in cell culture as well as in mice.

Figures 7A, 7B, 7C, 7D:
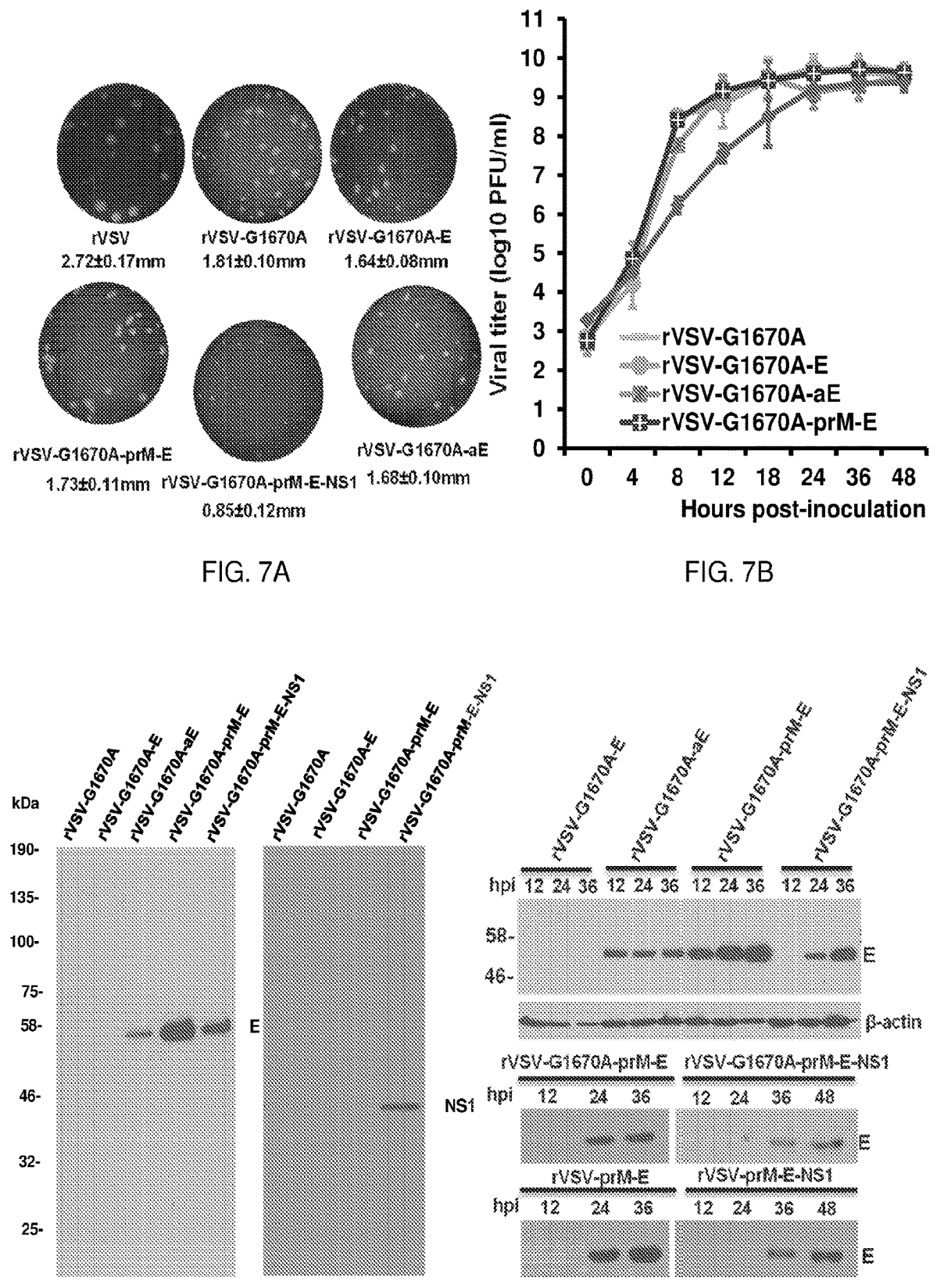

The G1670A mutation was introduced into rVSV-E, rVSV-aE, rVSV-prM-E, and rVSV-prM-E-NS1 to generate rVSV-G1670A-E, rVSV-G1670A-aE, rVSV-G1670A-prM-E, and rVSV-G1670A-prM-E-NS1, respectively (FIG. 7A). The plaque diameters of rVSV-G1670A-E, rVSV-G1670A-aE, rVSV-G1670A-prM-E, and rVSV-G1670A-prM-E-NS1 were 1.70±0.20, 1.67±0.111.71±0.15, and 1.05±0.12 mm respectively; significantly smaller than the recombinant viruses derived from the wild-type VSV backbone (cf. FIG. 7A and FIG. 1B). Single-step replication curves indicated that rVSV-G1670A-E, rVSV-G1670A-aE, and rVSV-G1670A-prM-E had replication kinetics similar to rVSV-G1670A, whereas rVSV-G1670A-prM-E-NS1 had a significant delay (P=5.82×10$^9$ and 0.0021 at time points 12 and 24 h, respectively; FIG. 7B). At 24 h post-infection, the expression of E can be ranked rVSV-G1670A-prM-E>rVSV-G1670A-prM-E-NS1>rVSV-G1670A-aE (FIG. 7C). No E protein expression was detected from rVSV-G1670A or rVSV-G1670A-E, but NS1 protein expression was detected from rVSV-G1670A-prM-E-NS1 (FIG. 7C).

In a kinetic experiment, E protein expression was maximal from rVSV-G1670A-aE and rVSV-G1670A-prM-E at 12 and 36 h, respectively, but was delayed in rVSV-G1670A-prM-E-NS1-infected cells (FIG. 7D).

Figures 7E, 8A, 8B:
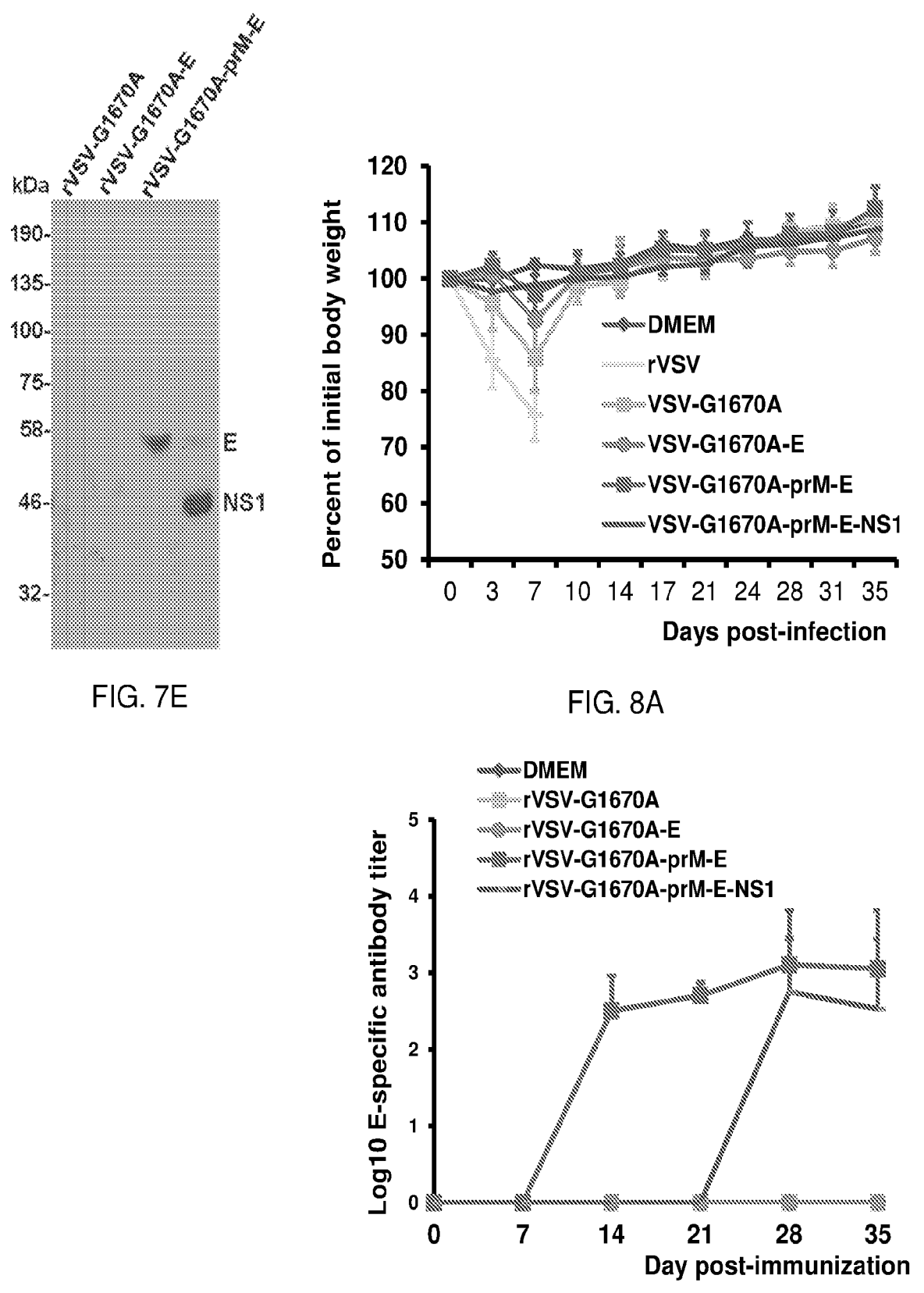

Similarly, E and NS1 proteins were secreted into cell culture medium in virus-infected cells (FIGS. 7D and 7E). Compared to the parental rVSV vector, E protein expression was delayed from the rVSV-G1670A vector (FIG. 2D), suggesting that the rVSV-G1670A vector was more attenuated. A large number of ZIKV VLPs were found in cell culture medium harvested from rVSV-G1670A-prM-E-NS1 and rVSV-G1670A-prM-E. These results demonstrated that ZIKV E and NS1 proteins were highly expressed by MTase-defective rVSV.

Example 6—mtdVSV-Based Vaccines are Highly Attenuate and Immunogenic

In an illustrative method, the MTase-defective VSV (mtdVSV)-based vaccines were tested in BALB/c mice. Intranasal wild-type rVSV killed the mice within 10 days (FIG. 8A). Mice inoculated with rVSV-G1670A or rVSV-G1670A-E showed 13% and 7% weight loss respectively at day 7 post-infection but both recovered by day 10 (FIG. 8A). Mice inoculated with rVSV-G1670A-prM-E-NS1 or rVSV-G1670A-prM-E exhibited 1-2% loss of body weight but were not significantly different than the DMEM control (P>0.05) (FIG. 8A), and exhibited no VSV-associated clinical symptoms, indicating a high degree of attenuation.

High levels of ZIKV E-specific antibody were detected by ELISA in rVSV-G1670A-prM-E and rVSV-G1670A-prM-E-NS1 mice at weeks 2 and 4 post-immunization, respectively (FIG. 8B). There was no significant difference in ELISA or neutralizing antibody titer (FIG. 8C) at week 5 between these two groups (P>0.05). No ZIKV specific antibody was detected in DMEM, rVSV-G1670A or rVSV-G1670A-E groups. Compared to the wild-type rVSV backbone, mtdVSV-based viruses had a delayed antibody response (cf. FIG. 6 and FIG. 8B), reflecting the significant attenuation of these recombinant viruses.

Figures 8C, 8D:
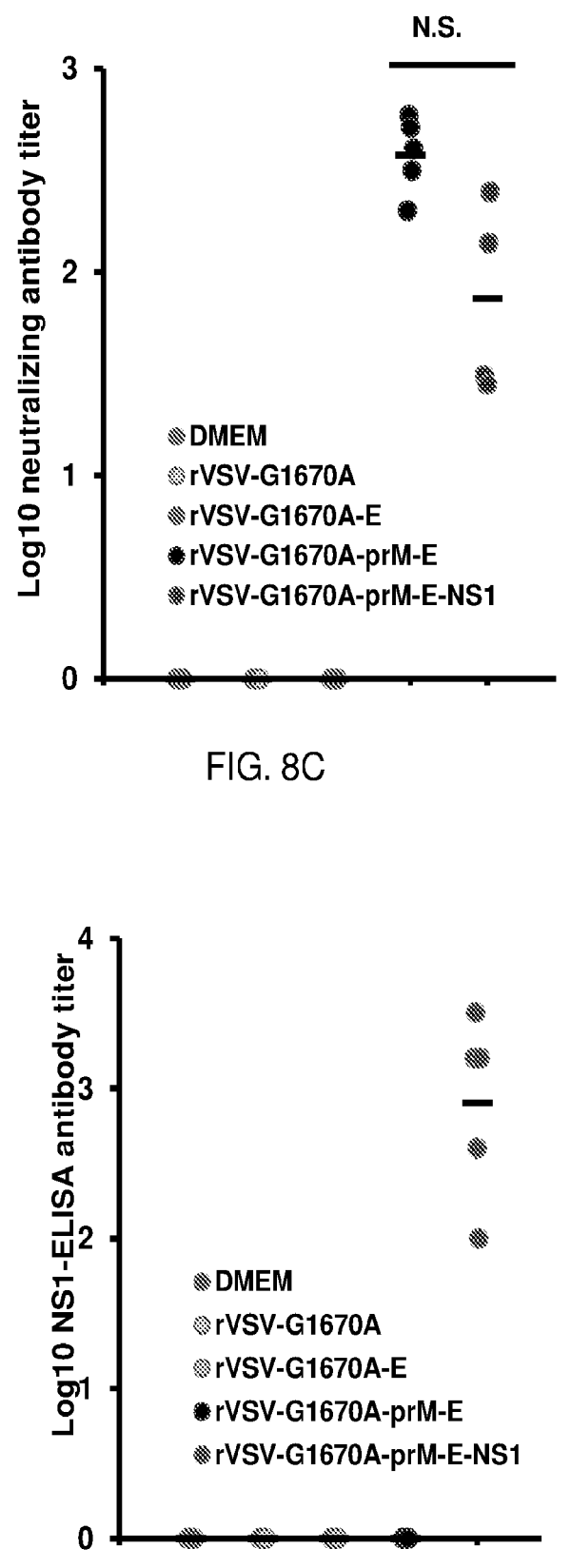

In addition, all mice in the rVSV-G1670A-prM-E-NS1 group developed NS1-specific antibody as detected by ELISA at week 5 (FIG. 8D). These results demonstrated that mtdVSV-based ZIKV vaccine candidates are highly attenuated and immunogenic in mice.

Example 7—Co-Expression of NS1 has a Regulatory Effect on the Profile of T Cell Responses Induction of antigen-specific Ab and cytotoxic T cell responses capable of providing protection after immunization requires T helper cells (CD4+CD3+ cells). In an illustrative method, it was found that spleen cells from mice that had been intranasally immunized with rVSV-G1670A-E, rVSV-G1670A-prM-E, or rVSV-G1670A-prM-E-NS1 and restimulated in vitro with ZIKV E protein, increased the number of T helper cells (CD3+CD4+) (FIG. 9A). This finding indicates that immunization induced ZIKV E protein-specific T cells capable of proliferation after re-exposure to the E antigen.

Th1 cells produce important cytokines (i.e., IFN-γ and TNF-α) for the production of complement-fixing Abs and cytotoxic T cells, which together are crucial for protection against intracellular pathogens such as viruses. Flow cytometry analysis of $CD3^+CD4^+$ cells producing Th1 cytokines revealed that only cells isolated from mice immunized with rVSV-G1670A-prM-E and rVSV-G1670A-prM-E-NS1 expressed ZIKV antigen-specific IFN-γ producing T helper cells ($CD4^+IFN-\gamma^+$) (FIG. 9B).

TNF-α producing T helper cells ($CD4^+TNF-\alpha^+$) were detected in the spleens of mice immunized with rVSV-G1670A-prM-E, but not rVSV-G1670A-prM-E-NS1 (FIG. 9B). These results indicate that co-expression of NS1 enhances IFN-γ, but inhibits production of TNF-α by T helper cells.

Figure 9D:
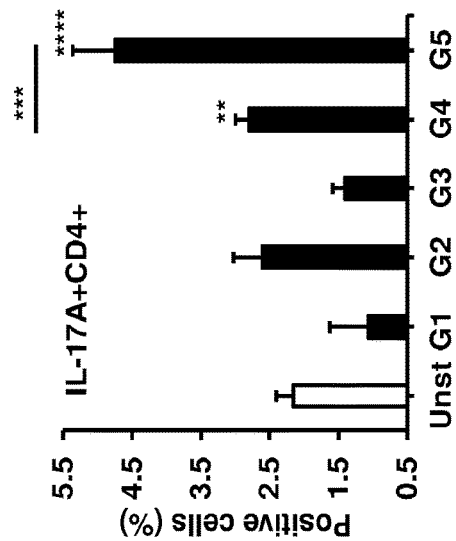
Figure 9E:
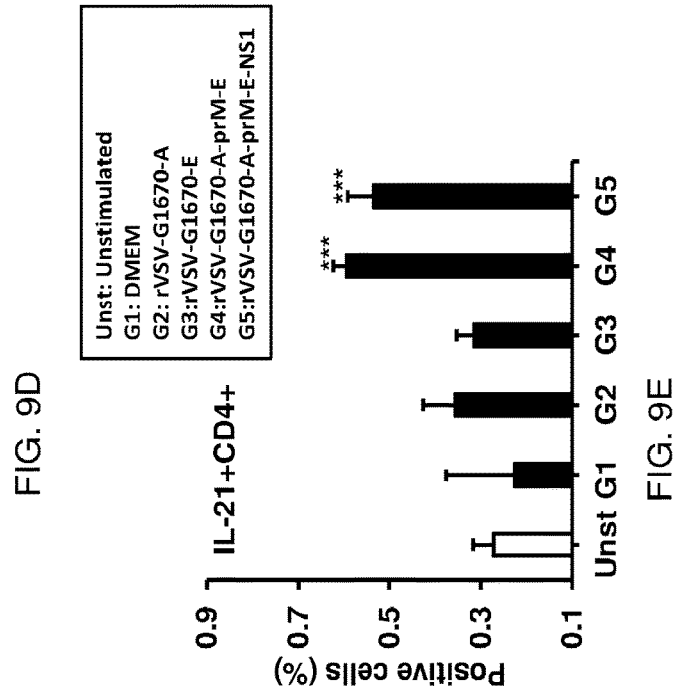

Th2 cells produce an array of cytokines which support the production of Abs more likely to protect against extracellular pathogens such as viruses. Interleukin 21, the signature product of follicular T helper cells (Tfh) and IL-17A, the product of Th17 cells, facilitate antibody production and affinity maturation. Both rVSV-G1670A-prM-E-NS1 and rVSV-G1670A-prM-E induced a similar level of $CD4^+IL-4^+$, a Th2 cytokine (P>0.05) in spleen cells after in vitro restimulation with ZIKV E protein (FIG. 9C). However, rVSV-G1670A-prM-E-NS1 induced significantly higher $CD4^+$ $IL-5^+$ and $CD4^+IL-10^+$, the other two Th2 cytokines (P<0.05) (FIG. 9C).

rVSV-G1670A-prM-E-NS1 also induced a significantly higher Th17 response ($CD4^+IL-17A^+$) than rVSV-G1670A-prM-E (P<0.05) (FIG. 9D). In addition, ZIKV E-specific Tfh cells ($CD4^+IL-21^+$) were produced at similar levels in rVSV-G1670A-prM-E-NS1 and rVSV-G1670A-prM-E inoculated mice (P>0.05) (FIG. 9E).

These results demonstrated that mtdVSV-based vaccines triggered ZIKV-specific T cell responses and that co-expression of NS1 enhances Th2 and Th17 responses. The fact that co-expression of NS1 enhances IFN-γ indicates that NS1 modulated the Th1 response (FIG. 9B). Collectively, these results indicate that the presence of NS1 leads to a more balanced response including Th1, Th2, and Th17 cells.

Figure 10:
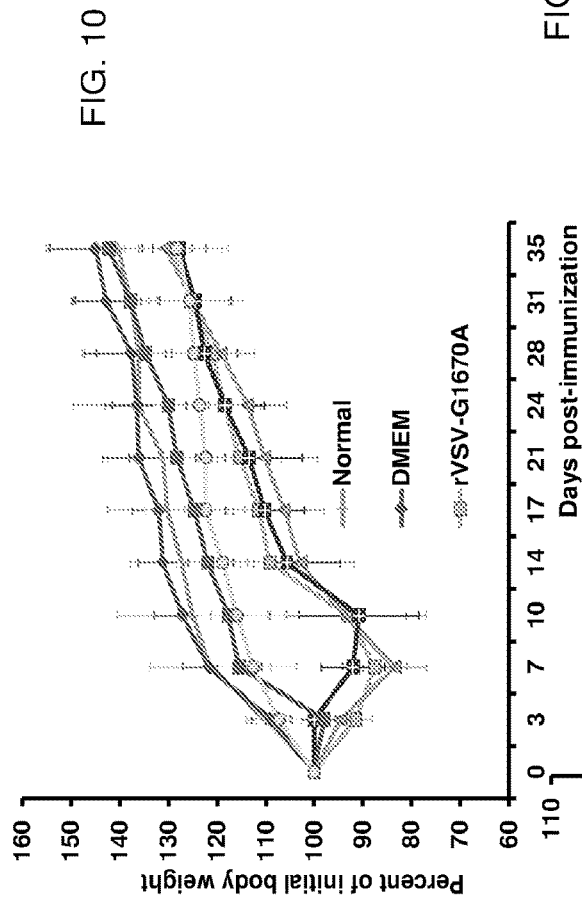
FIG. 10 is a representative line graph illustrating the dynamics of body weight change of BALB/c mice after immunization with the indicated mtdVSV vectors.

Example 8—A Single Dose of mtdVSV-Based Vaccines Protects BALB/c Mice from ZIKV Viremia In an illustrative method, the protective effect of mtdVSV-based ZIKV vaccines was determined in both female and male BALB/c mice. Mice were vaccinated intranasally with a single dose ($10^6$ PFU) of each recombinant virus, and were challenged with ZIKV Cambodian strain (FSS13025) at week 5 post-immunization. DNA vaccine (pCI-prM-E) was used as a control and was given intramuscularly twice (at week 0 and 2). Similar to the previous observation (FIG. 8A), prM-E-NS1 was the most attenuated virus, with mice experiencing no weight loss (FIG. 10). All other recombinant viruses resulted in 9-15% weight loss at early time points, but weights recovered by day 14 (FIG. 10).

Figure 11:
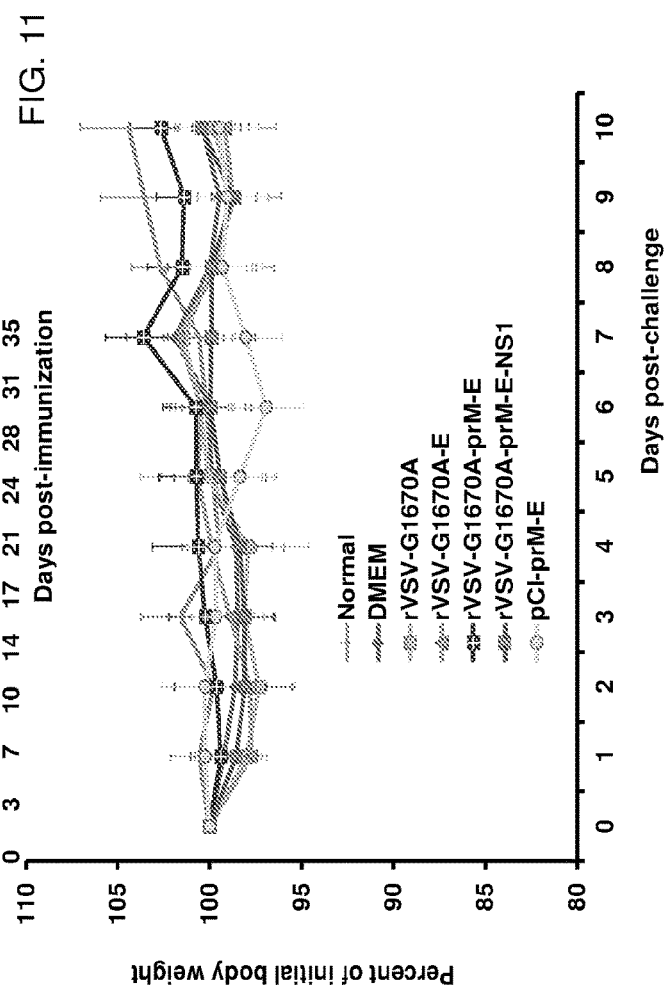
FIG. 11 is a representative line graph illustrating the dynamic of body weight change of BALB/c mice inoculated with the indicated mtdVSV vector, after challenge with ZIKV. The average body weights of ten mice are shown. No significant difference in body weight was observed among groups (P>0.05).

Previously, it was shown that the administration of anti-IFNAR1 antibody could render BALB/c mice more susceptible to ZIKV infection, resulting in significant weight loss and ZIKV-associated clinical signs upon challenge with a mouse-adapted African ZIKV strain (Dakar 41519). 1.8 mg of a blocking antibody, anti-IFNAR1, was passively transferred to each mouse 24 h prior to challenge with the ZIKV. After ZIKV challenge, mice were monitored for 4 weeks. No significant weight loss or clinical symptoms were observed in any group including the unvaccinated but challenged controls (FIG. 11).

Figures 12A, 12B:
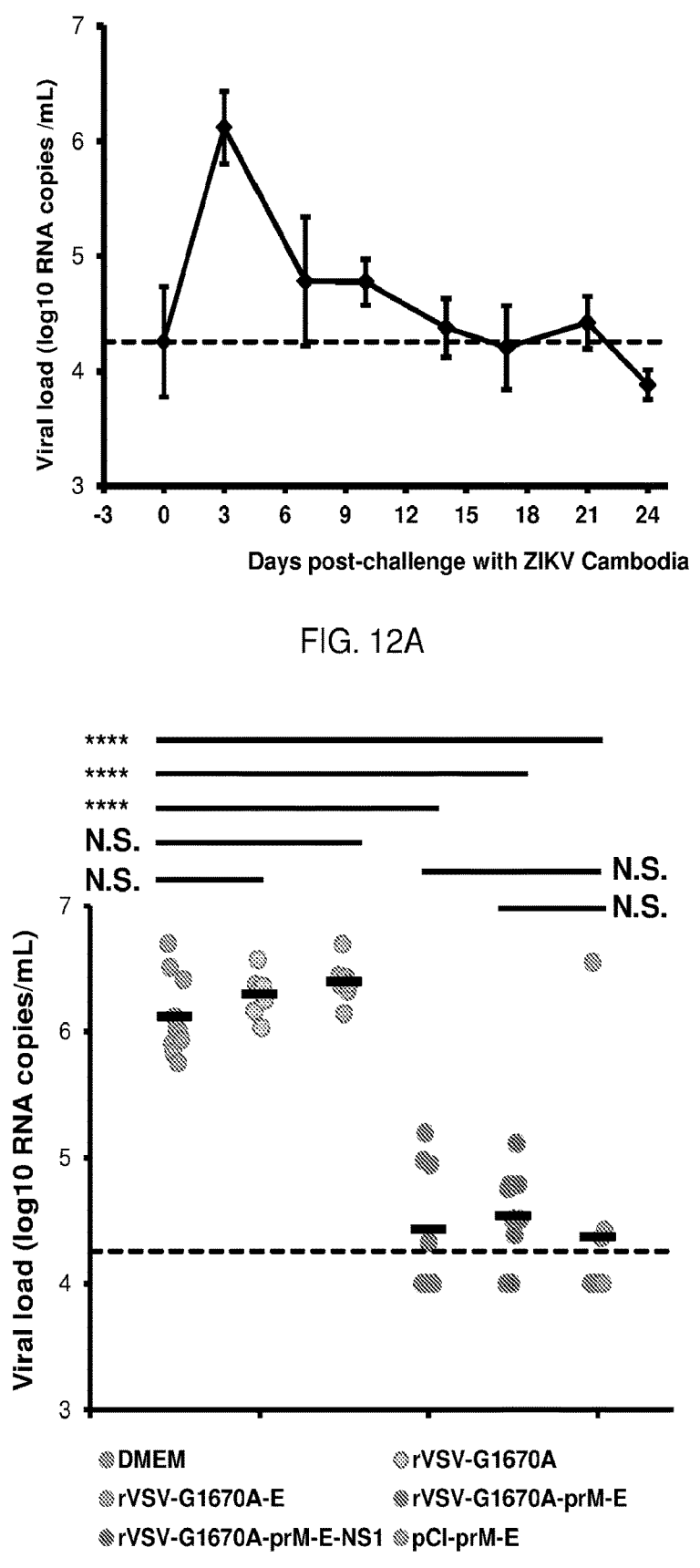

The dynamics of viremia were monitored every 3-4 days until day 24 after ZIKV challenge (except the pCI-prM-E group, which was only monitored at days 3 and 7) and detected by real-time RT-PCR. For the unvaccinated challenged controls, the peak of viremia was observed at day 3, declined by days 7 and 10, and cleared by day 14 (FIGS. 12A and 19A). This was consistent with previous observations that ZIKV only causes transient viremia in BALB/c mice. Similarly, mice in the rVSV-G1670A and rVSV-G1670A-E groups developed viremia, shedding an average of 3.7 logs of ZIKV PFU RNA/ml in blood samples collected at day 3 post-challenge (FIG. 12B). In contrast, mice that had been vaccinated with rVSV-G1670A-prM-E, rVSV-G1670A-prM-E-NS1, and pCI-prM-E were under the detection limit at day 3 (3 and 4 mice in rVSV-G1670A-prM-E and rVSV-G1670A-prM-E-NS1 had near detection limit level of viremia, respectively, and 1 mice in pCI-prM-E group had a high level of viremia) (FIG. 19A and FIG. 12B). In addition, viremia was under detection limit from days 7 to 24 in these groups (FIG. 19A)

Collectively, these data indicate that a single dose vaccination of mtdVSV-based vaccines provides protection against ZIKV-induced viremia in BALB/c mice.

To determine whether VSV was persistent in the vaccinated mice, brain tissues were collected at the termination of the study for detection of VSV. No infectious VSV was detected by plaque assay in any brain tissues in any group. However, 4-5 log VSV RNAs were detected in the brains of the rVSV-G1670A, rVSV-G1670A-E, and rVSV-G1670A-prM-E groups (FIG. 19B). In contrast, nearly no VSV RNA was detected in the rVSV-G1670A-prM-E-NS1 group (FIG. 19B). Therefore, rVSV-G1670A-prM-E-NS1 is the most attenuated of these viruses.

Figures 21, 22, 23:
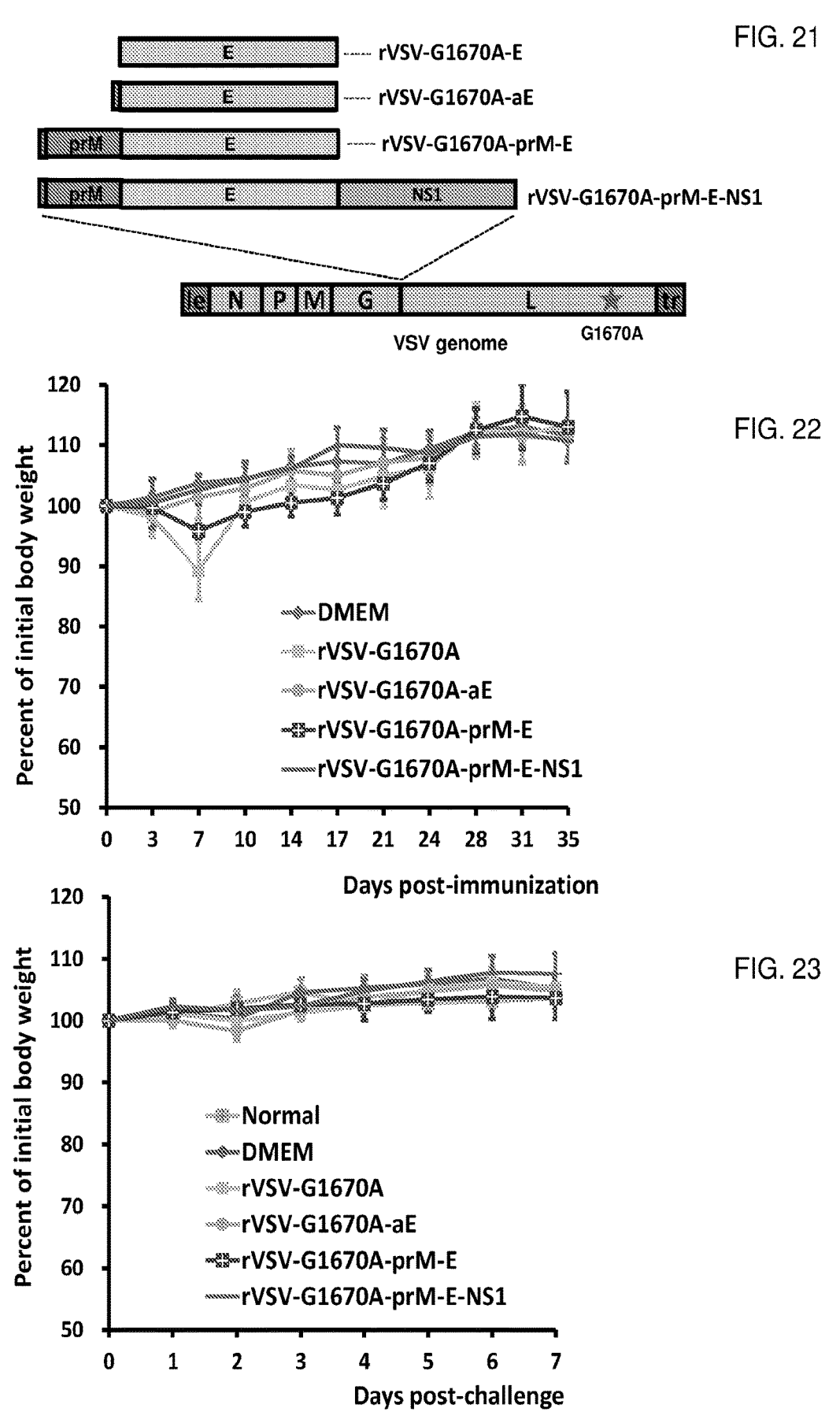

The above animal experiment was repeated, where rVSV-G1670A-aE was included in the vaccination. Recombinant rVSV-G1670A-prM-E-NS1 and rVSV-G1670A-aE had no body weight loss whereas rVSV-G1670A-prM-E had approximately 4.2% body weight loss at day 7 (FIG. 22). High E-specific antibodies were observed in all animals vaccinated with rVSV-G1670A-prM-E or rVSV-G1670A-prM-E-NS1 at day 28 and further increased at day 35 post-vaccination (FIG. 19C). Only 1 out of 5 animals vaccinated with rVSV-G1670A-aE developed E-specific antibodies from day 7 to 28, and all animals developed E-specific antibodies at day 35 (FIG. 19C). NS1-specific antibodies were only detected in rVSV-G1670A-prM-E-NS1 group (FIG. 19D). Upon ZIKV challenge, mice did not exhibit body weight loss (FIG. 23). Mice vaccinated with rVSV-G1670A-prM-E and rVSV-G1670A-prM-E-NS1 were protected from viremia at days 3 (FIG. 19E) and 7 (FIG. 19F) post-challenge whereas mice received rVSV-G1670A-aE shed high titer of ZIKV RNA in blood in a level similar to the rVSV-G1670A and saline control groups.

Example 9—a Single Dose of mtdVSV-Based Vaccine Provides Complete Protection Against Lethal ZIKV Infection in INFAR-Lacking Mice In an illustrative method, the protective effect of mtdVSV-based ZIKV vaccines was assessed in A129 mice, which lack the interferon type I receptor (IFNAR) and, therefore, signaling responses to type I interferons. These mice have been demonstrated to be highly permissive for both ZIKV and VSV infection. A129 mice are so susceptible to wild-type VSV infection that a dose of 50 PFU is lethal.

Figures 13, 14A, 14B:
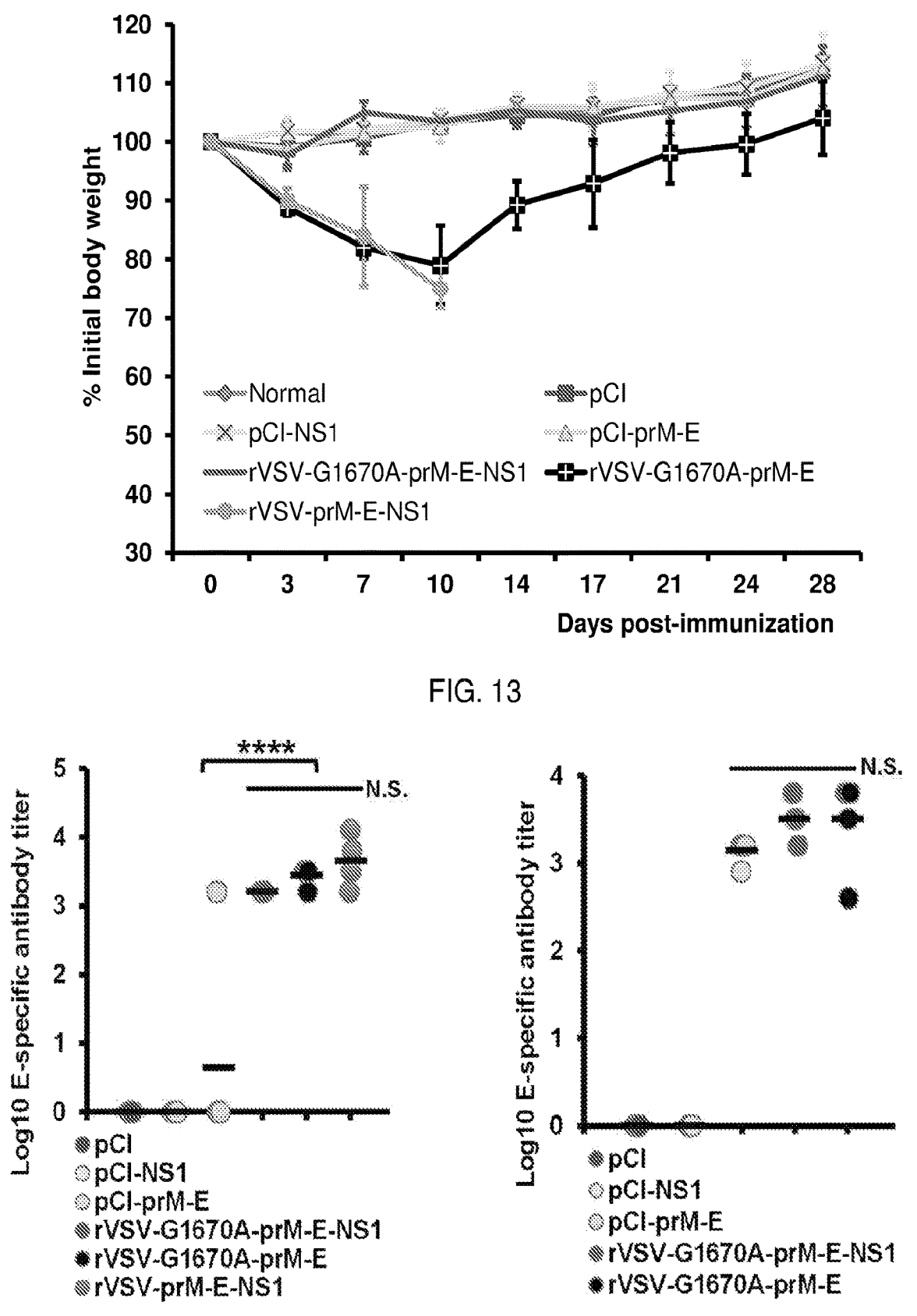

To reduce side effects, an intramuscular route was used for VSV vaccination. Since mtdVSV-based vaccines were significantly attenuated, a dose of $10^5$ PFU was chosen for vaccination, which was 20,000 times higher than the wild-type VSV lethal dose. A129 mice were immunized intramuscularly with rVSV-G1670A-prM-E-NS1, rVSV-G1670A-prM-E, or rVSV-prM-E-NS1, and the safety and antibody response were monitored. It was observed that VSV-G1670A-prM-E-NS1 was completely attenuated in A129 mice, exhibiting no body weight losses or any abnormal reactions (FIG. 13). However, rVSV-prM-E-NS1, which lacks the VSV attenuating mutation, was virulent in A129 mice, causing 2 deaths at day 7, and morbidity by day 10 that required termination of the others.

Figures 14C, 14D, 14E, 14F:
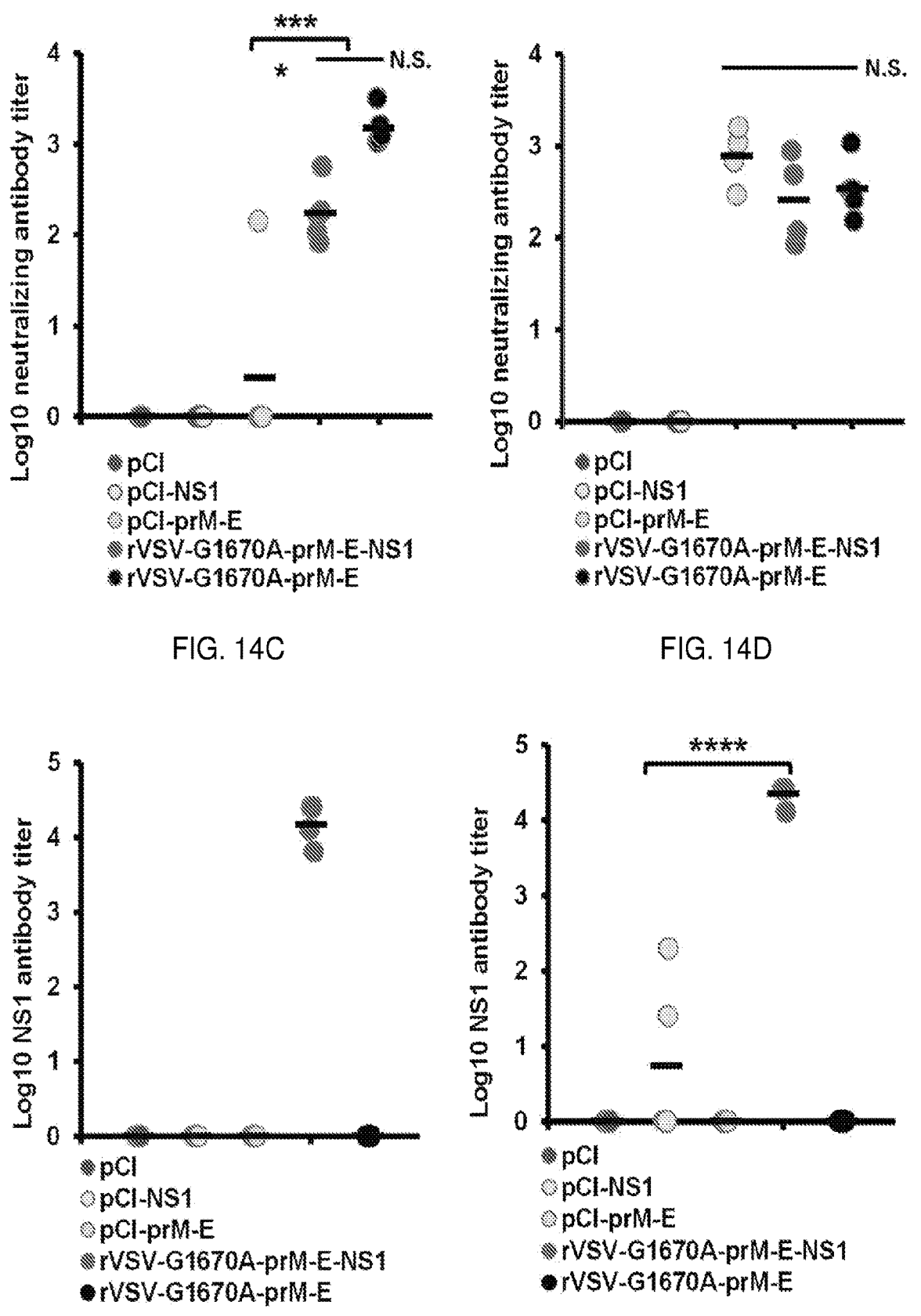

Mice immunized with rVSV-G1670A-prM-E lost 20% of their weight but recovered and remained healthy. As illustrated by FIG. 14, all mice in rVSV-G1670A-prM-E-NS1 and rVSV-G1670A-prM-E groups developed high levels of antibody, detected by ELISA (FIG. 14A) and by neutralization (FIG. 14C) as early as week 1 post-vaccination. Ab titers remained high at week 3 (FIGS. 14B and 14D). In addition, high levels of NS1-specific Ab were detected at weeks 1 and 3 in the rVSV-G1670A-prM-E-NS1 group (FIGS. 14E and 14F). At week 4 post-immunization, each group was challenged with $10^5$ PFU of the ZIKV Cambodian strain.

Figures 14G, 15A, 15B, 15C:
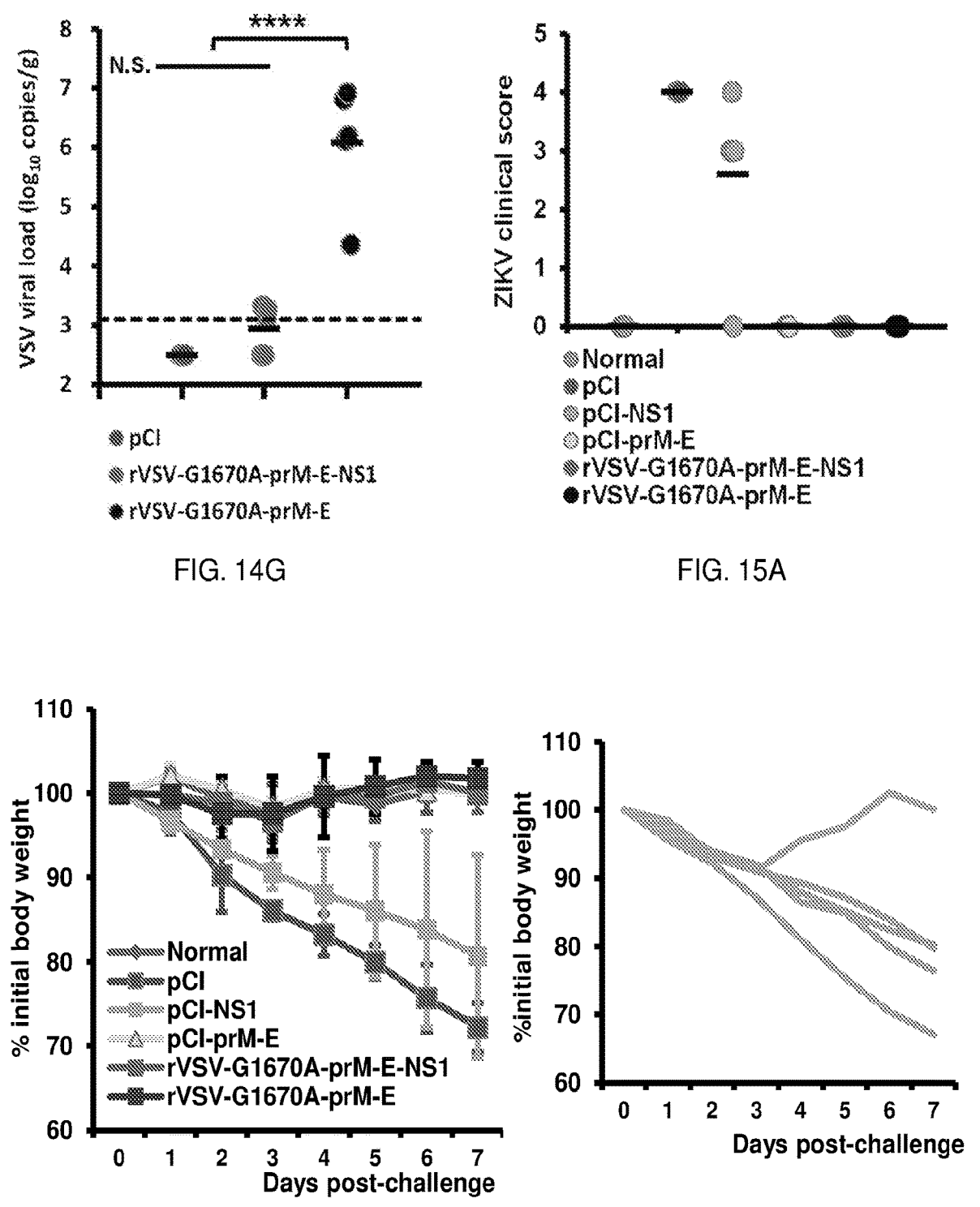

Mice in the control, unvaccinated challenged group (immunized with the empty pCI plasmid) developed severe clinical signs (FIG. 15A) and had severe body weight loss (FIG. 15B). Because of the severity of disease in the pCI control group, these mice were terminated at day 7.

Figures 16A, 16B, 16C, 16D:
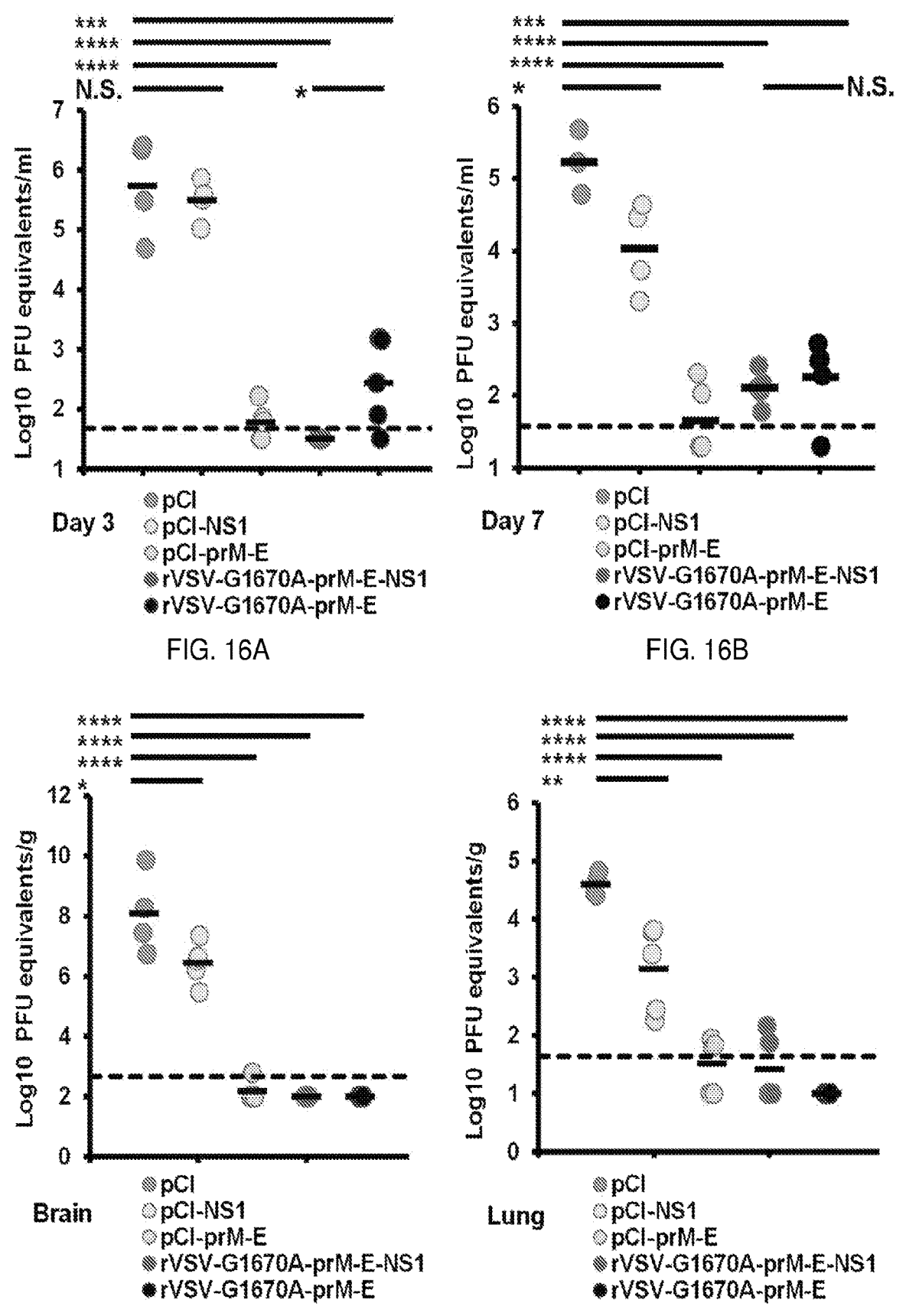

In contrast, mice vaccinated with either rVSV-G1670A-prM-E-NS1 or rVSV-G1670A-prM-E did not exhibit any weight loss (FIG. 15B) or ZIKV associated clinical symptoms (FIG. 15A). ZIKV viremia was measured at days 3 and 7 post-challenge by real-time RT-PCR (FIGS. 16A and 16B). An average of 5.8 log PFU equivalents of ZIKV was detected in the pCI control group at day 3. Low ZIKV PFU equivalents were detected at day 3 in the rVSV-G1670A-prM-E group but none in the rVSV-G1670A-prM-E-NS1 group. At day 7, high levels of ZIKV were detected in the blood of the pCI control group, whereas no or very low ZIKV was found in rVSV-G1670A-prM-E-NS1 and rVSV-G1670A-prM-E groups.

Similarly, high levels of ZIKV were detected in the brain, uterus, lung, and spleen of the pCI control group whereas under or near detection limit level ZIKV RNA was found in these organs in the rVSV-G1670A-prM-E and rVSV-G1670A-prM-E-NS1 groups (FIGS. 16C-16F). In addition, histologic analysis of brain tissues showed that rVSV-G1670A-prM-E and rVSV-G1670A-prM-E-NS1 had completely protected the mice from ZIKV-induced encephalitis (FIG. 17). In contrast, severe encephalitis characterized by neuronal necrosis, gliosis, neuronal satellitosis and neuronophagia with lymphocytic perivascular cuffing was found in the control group (FIG. 17). The brain tissues were used for the detection of VSV RNA. It was found that VSV RNA was not detectable or near the detection limit in A129 mice vaccinated with rVSV-G1670A-prM-E-NS1 whereas approximately 6 log of VSV RNA were detected in rVSV-G1670A-prM-E group (FIG. 14G), indicating that rVSV-G1670A-prM-E-NS1 was significantly more attenuated than rVSV-G1670A-prM-E.

These data demonstrate that a single low dose of mtdVSV-based vaccines provides complete protection against ZIKV challenge in A129 mice that are extremely sensitive to both VSV and ZIKV.

Figures 18A, 18B:
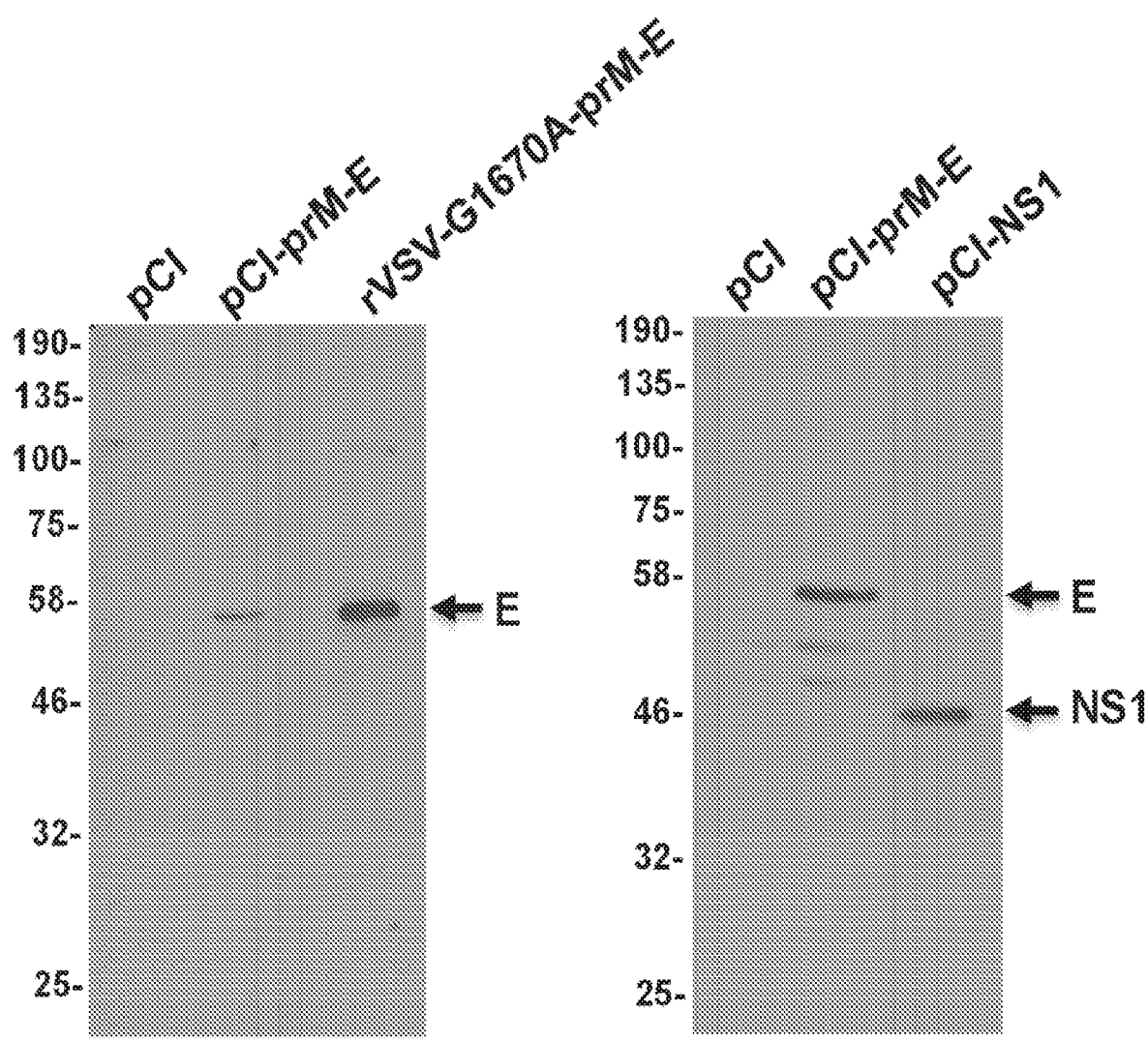
FIGS. 18A & 18B are representative digital photographs of Western blots illustrating a comparison of ZIKV E protein expression by pCI-prM-E and rVSV-G1670A-prM-E (FIG. 18A), and the expression of ZIKV NS1 protein by pCI-NS1 (FIG. 18B).

Example 10—NS1 Provides Partial Protection Against ZIKV Challenge without Inducing Neutralizing Antibody In an illustrative method, to determine whether prM-E or NS1 proteins, alone, can induce protection against a ZIKV challenge, DNA vaccination was used. DNA vaccine is safe to A129 mice. The NS1 gene with anchor C signal peptide was cloned into pCI vector. Both pCI-prM-E and pCI-NS1 expressed their intended proteins, E and NS1, in transfected 293T cells (see FIGS. 18A & 18B). A129 mice were vaccinated intramuscularly with pCI-prM-E or pCI-NS1, and boosted with the same plasmid two weeks later. Only 1 out of 5 mice in the pCI-prM-E group had E-specific ELISA and neutralizing Ab at week 1 (FIGS. 14A and 14C) but all of them had high levels of ZIKV E-specific Ab at week 3 (FIGS. 14B and 14D). No ZIKV neutralizing Ab was detected in the pCI-NS1 group even after the boost (FIGS. 14B and 14D), but Ab to NS1 was detected in 2 out of 5 mice at week 3 (FIG. 14F).

Figures 15D, 15E, 15F, 15G:
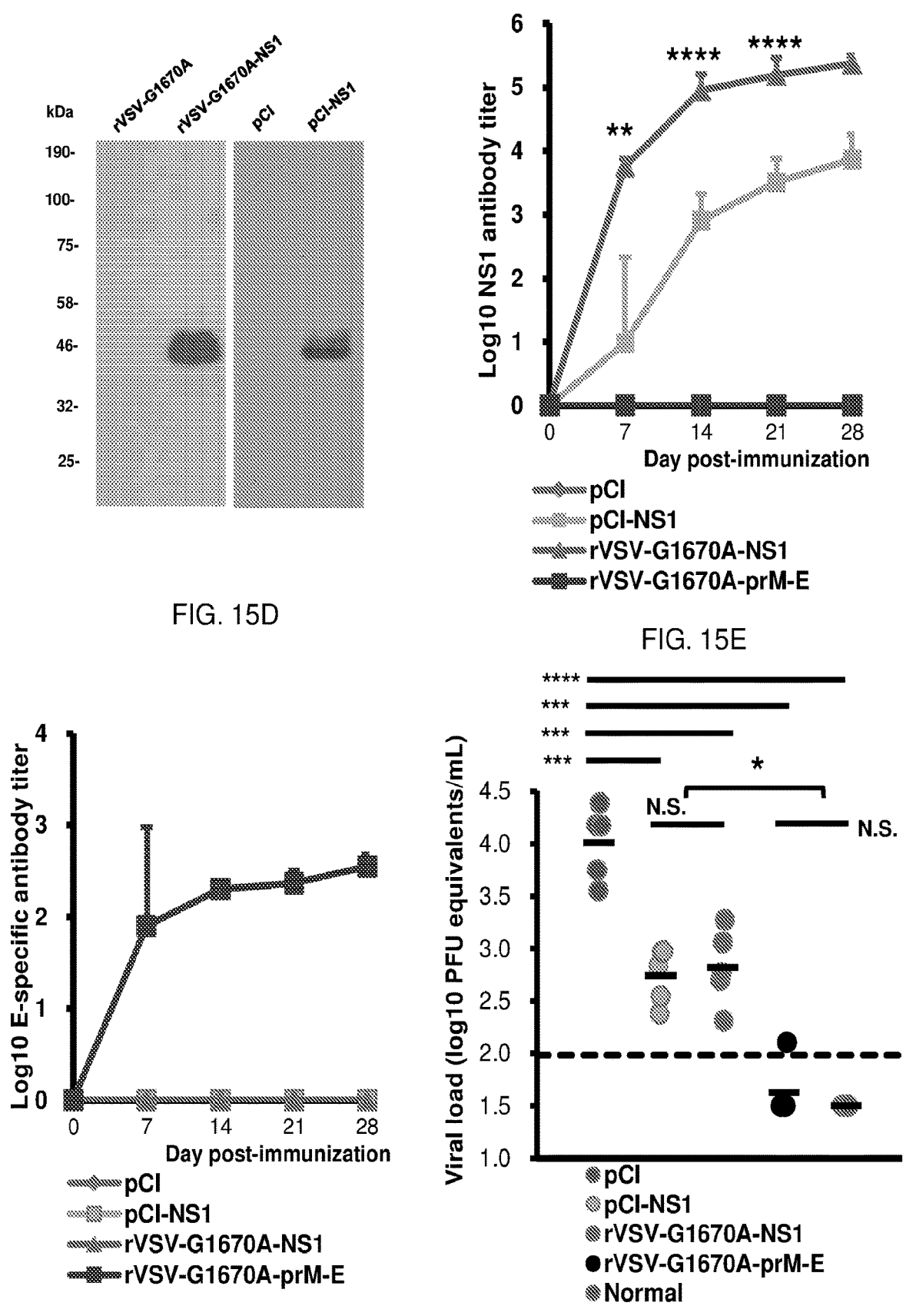
Figures 16E, 16F, 17:
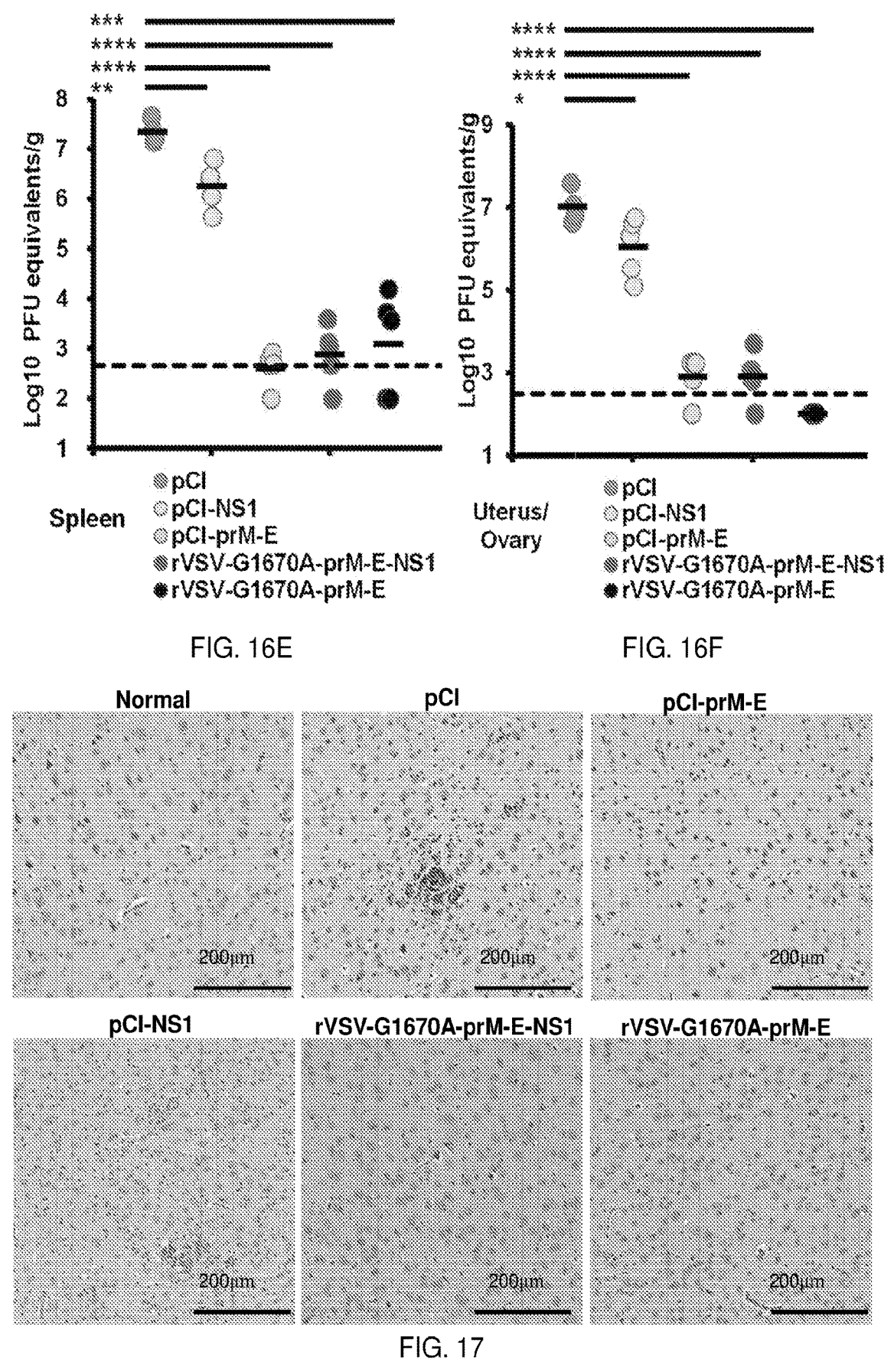

Mice vaccinated with pCI-prM-E were protected from a ZIKV challenge at week 4 (FIG. 15). One of the five mice in the pCI-NS1 group only had 10% weight loss and quickly recovered (FIG. 15C). The other four mice in the pCI-NS1 group exhibited clinical signs, but less severe than the pCI group (FIG. 15A). Overall, weight loss in the pCI-NS1 group was less than the pCI control group (FIG. 15B). At day 3 post-challenge, the pCI-NS1 group had a level of viremia similar to the pCI control group (P>0.05) (FIG. 16A), but by day 7 the pCI-NS1 group had significantly less viremia (P<0.05) (FIG. 16B). Similarly, significantly less ZIKV was detected in spleen, uterus, lung, and brain in the pCI-NS1 group compared to the pCI control group (P<0.05 or P<0.01) (FIG. 16C-F). Histologic analysis showed that the pCI-NS1 group had less severe encephalitis compared to the pCI group (FIG. 17).

Collectively, these data demonstrate that ZIKV NS1 was capable of conferring partial protection against ZIKV challenge in A129 mice in the absence of detectable ZIKV neutralizing Ab.

Figure 15H:
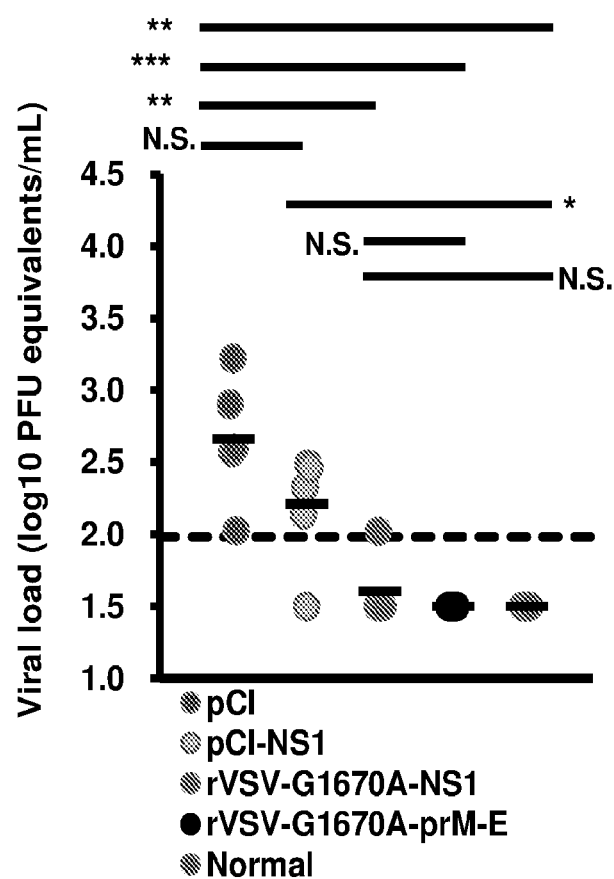
FIG. 15H is a dot plot illustrating that NS1 alone provided protection against viremia in BALB/c mice at day 7 post-challenge. P value from top to bottom: P=0.00510, *P=0.000114, **P=0.00277, *P=0.0308

To further improve the protection efficacy of NS1, mtdVSV expressing NS1 alone (rVSV-G1670A-NS1) was recovered, in which the ZIKV NS1 gene with anchor C was inserted at the gene junction between G and L genes. Western blot indicated that the NS1 expression in rVSV-G1670A-NS1-infected cells was significantly higher than pCI-NS1-transfected cells (FIG. 15D). A pilot experiment demonstrated that rVSV-G1670A-NS1 still caused considerable weight loss in A129 mice. The protection efficacy of rVSV-G1670A-NS1 was tested in BALB/c mice. BALB/c mice were immunized intramuscularly with two doses (50 µg each) of pCI-NS1 or intranasally with one dose ($10^6$ PFU) of rVSV-G1670A-NS1 or rVSV-G1670A-prM-E, and were challenged intravenously with $10^6$ PFU of ZIKV at week 4 post-immunization. We found that rVSV-G1670A-NS1 triggered significantly higher NS1-specific antibody than pCI-NS1 in mice (FIG. 15E). As a positive control, recombinant rVSV-G1670A-prM-E triggered a high level of E-specific antibody (FIG. 15F). At days 3 post-challenge, mice in rVSV-G1670A-NS1 and pCI-NS1 groups had a similar level of viremia (P>0.05) but were significantly lower than pCI control (P<0.05) (FIG. 15G). As a positive control, the viremia level in the rVSV-G1670A-prM-E group was below or near detection limit (FIG. 156G). At day 7 post-challenge, mice in the rVSV-G1670A-NS1 and rVSV-G1670A-prM-E groups had no detectable viremia (except one in rVSV-G1670A-NS1 group which was near the detection limit) whereas mice in pCI and pCI-NS1 groups still had a significant level of viremia (P<0.001) (FIG. 15H). These results indicated that NS1 alone was capable of triggering significant protection against ZIKV-induced viremia and that rVSV-G1670A-NS1 had a higher protection efficacy than pCI-NS1.

Figures 20A, 20B, 20C:
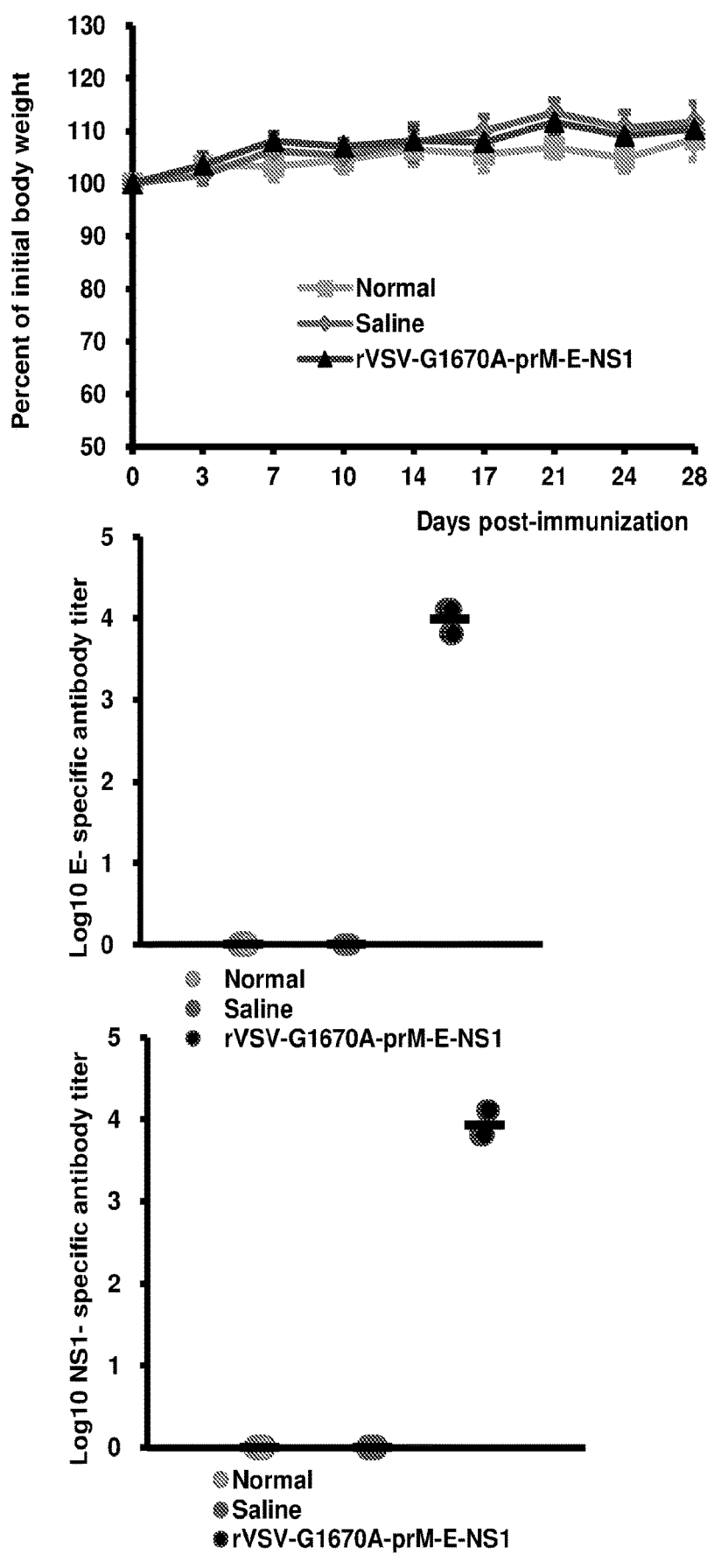
Figures 20D, 20E:
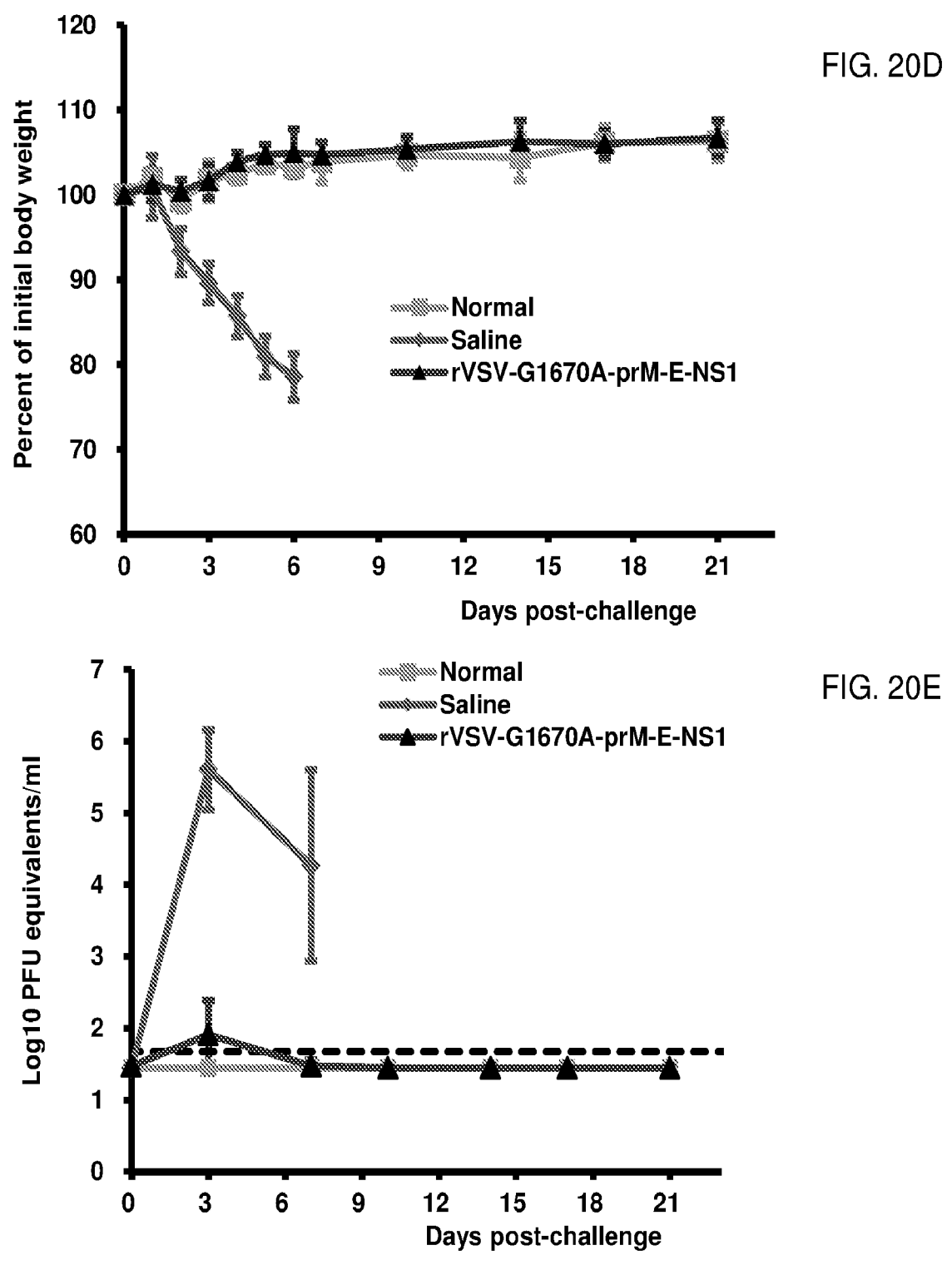

Example 11—Validation of the Safety and Efficacy of rVSV-G1670A-prM-E-NS1 in A129 Mice The protection efficacy of rVSV-G1670A-prM-E-NS1 was further validated in A129 mice by monitoring body weight and viremia for a prolonged time (until day 21 after challenge with ZIKV). As indicated in FIG. 20A, there were no significant differences in body weight gain among three groups (P>0.05), $10^5$ PFU of rVSV-G1670A-prM-E-NS1, saline, and normal controls, demonstrating the high safety profile of rVSV-G1670A-prM-E-NS1 in A129 mice. rVSV-G1670A-prM-E-NS1 triggered a high level of E-specific (FIG. 20B) and NS1-specific (FIG. 20C) antibodies. Upon challenge with ZIKV Cambodian strain, mouse body weight and viremia were monitored every 1 or 3 days until day 21. Mice that received the saline control were all dead at day 6 post-challenge (FIG. 20D). The body weight in rVSV-G1670A-prM-E-NS1 group was indistinguishable from normal control (P>0.05) at all time points (FIG. 20D). Saline control group developed high levels of ZIKV induced viremia whereas rVSV-G1670A-prM-E-NS1 group had a baseline level of viremia at day 3 and no detectable viremia between days 3 and 21 (FIG. 20E). Collectively, rVSV-G1670A-prM-E-NS1 is of high safety and efficacy against ZIKV infection.

Example 12—rVSV-D1762A Backbone

Figures 24, 25A, 25B:
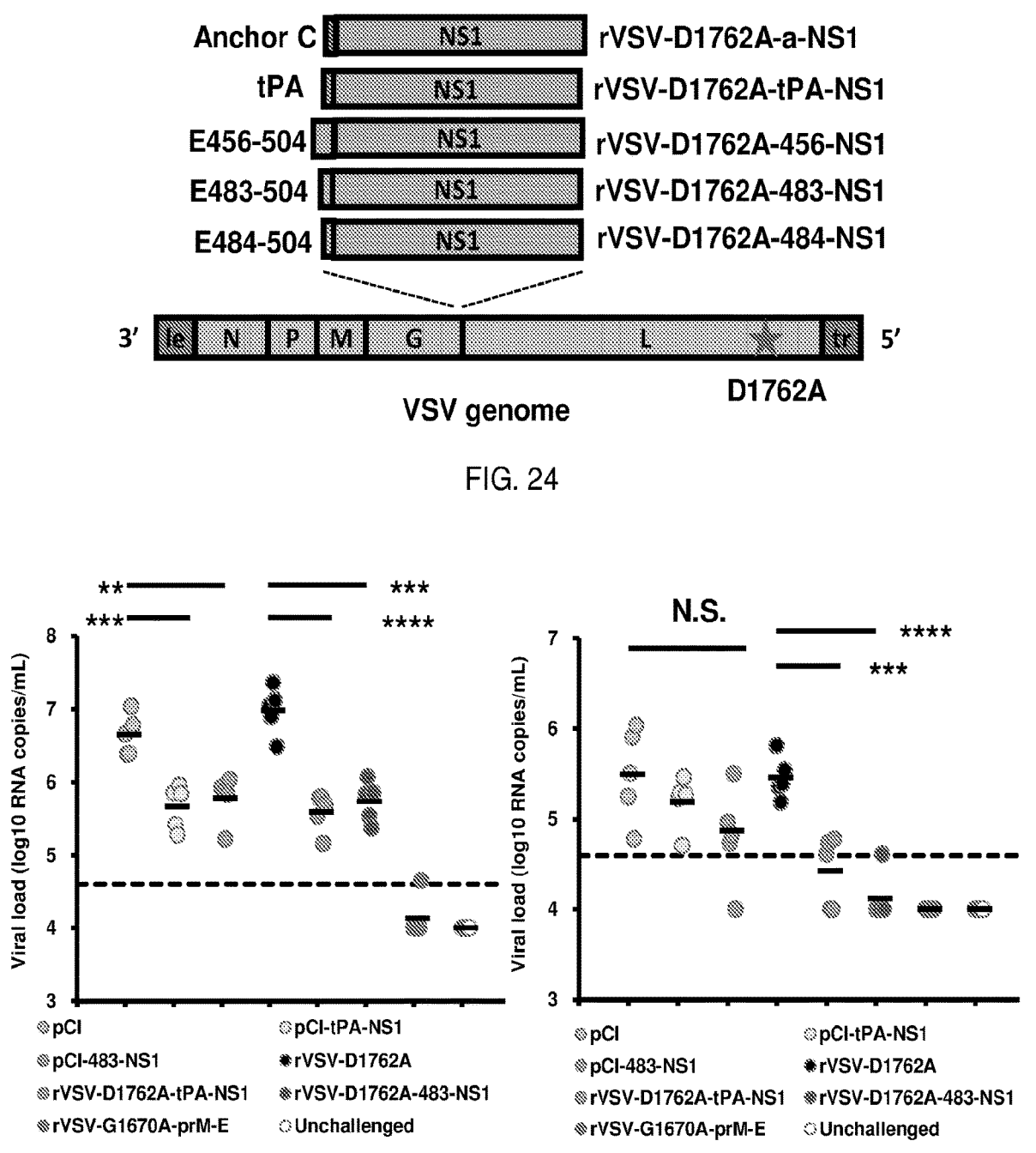

In an illustrative method, a D1762A mutation was introduced into the plasmid encoding the VSV antigenome, pVSV-GxxL, resulting in pVSV-D1762A-GxxL. Using pVSV-D1762A-GxxL as the backbone, ZIKV NS1 gene was inserted into the gene junction between G and L. Five recombinant VSVs (rVSV) expressing ZIKV NS1 protein were recovered (FIG. 24). These recombinant viruses differed only in the signal peptide sequence which is fused to the N terminus of ZIKV NS1 protein. Recombinant rVSV-D1762A-a-NS1 also contains the anchor C sequence from the ZIKV genome, as the anchor C sequence has been shown to be essential for expression of ZIKV prM-E protein. Recombinant rVSV-D1762A-tPA-NS1 contains the signal sequence encoding human tissue plasminogen activator (t-PA) fused to NS1.

Three recombinant viruses containing the transmembrane domain of the ZIKV E protein from the C-terminus of the E protein inserted at the N-terminus of the NS1 protein were also constructed. This domain can function as a signal peptide and potentially enhance NS1 protein expression. Since the exact length of this signal sequence is unclear, three recombinant viruses with different lengths of this signal sequence connected to the NS1 protein were constructed. These recombinant viruses were named rVSV-D1762A-456-NS1, rVSV-D1762A-484-NS1, and rVSV-D1762A-483-NS1 which contain amino acid residues from 456 to 504, 484 to 504, and 483 to 504 from C-terminal of ZIKV E protein, respectively as the signal peptide (FIG. 24).

After recovery, all recombinant viruses were plaque purified. All recombinant viruses contained the desired insertions as indicated by sequencing. No mutations were found in the genome except for the D1762A substitution in the L gene. The parental rVSV formed large plaques at 36 h post-inoculation with an average diameter of 2.83±0.57 mm (mean±standard deviation). All other recombinant viruses formed significantly smaller plaques. The rVSV-D1762A-a-NS1 virus had a plaque size of 0.87±0.18 mm, similar to the backbone virus rVSV-D1762A (0.85±0.20 mm). The rVSV-D1762A-tPA-NS1, rVSV-D1762A-456-NS1, rVSV-D1762A-483-NS1, and rVSV-D1762A-484-NS1 viruses formed even smaller plaques with average size of 0.62±0.12 mm, 0.57±0.09 mm, 0.65±0.10 mm, and 0.52±0.15 mm, respectively. These results indicate that the D1762A methyltransferase-defective rVSVs (mtdVSVs) expressing NS1 had dramatically reduced replication and/or cell-to-cell spread. 1181 BALB/c mice were challenged intraperitoneally with $10^6$ PFU of ZIKV Cambodian strain (FSSS13025) at week 4 post-immunization with mtdVSV-NS1 based vaccines or DNA vaccines. All mice were injected intraperitoneally with 2 mg of IFNAR1 antibody 24 h prior to ZIKV challenge. No significant body weight losses or ZIKV-associated clinical symptoms were observed in any group, including the unvaccinated but challenged controls, which was consistent with the observations of several other groups that ZIKV infection does not cause illness in immunocompetent mice.

Figures 25C, 25D, 26A, 26B:
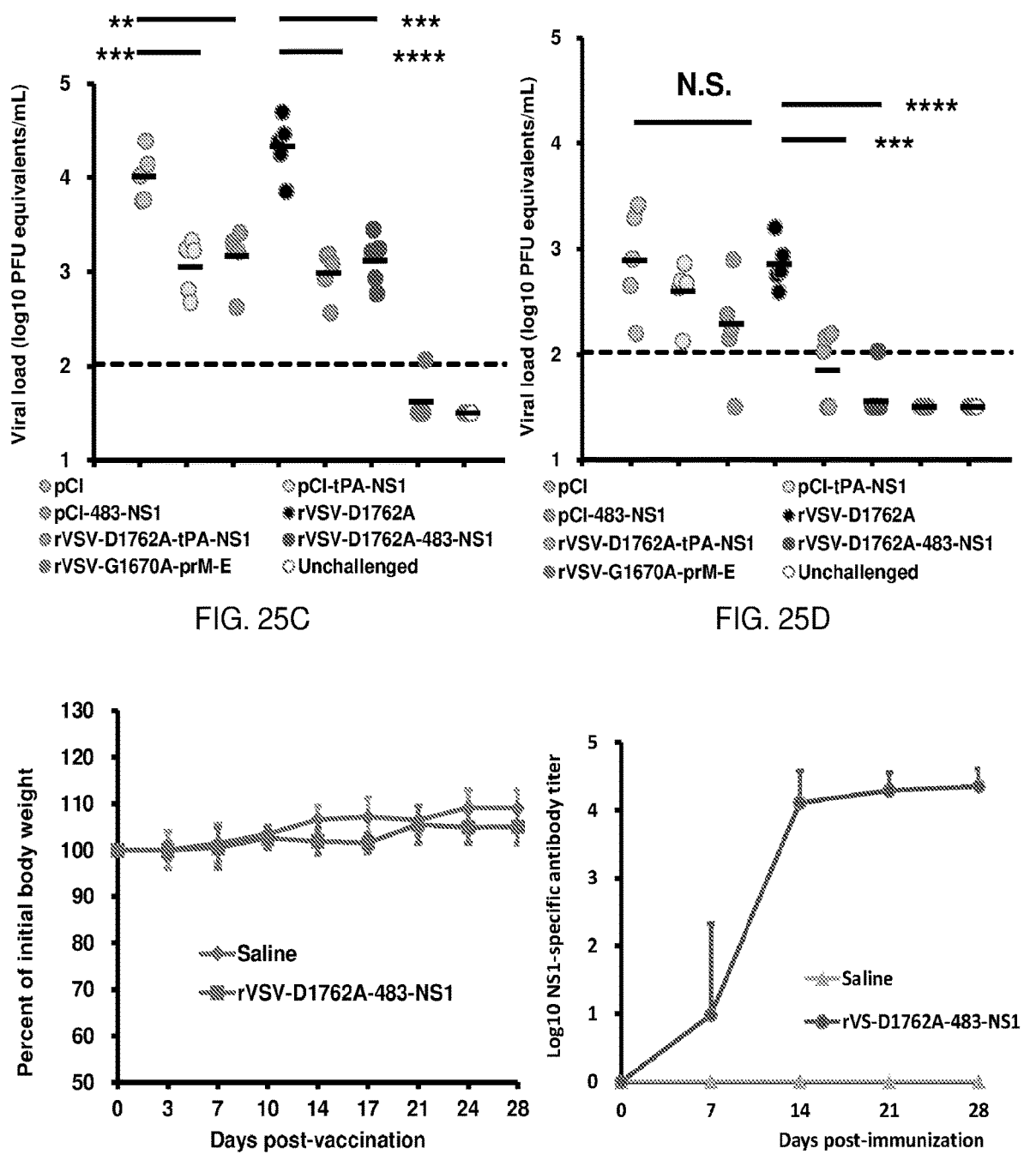

Blood samples were collected from each mouse at days 3 and 7 post-challenge to measure viremia. The unvaccinated challenged groups (pCI and rVSV-D1762A) developed a high level of ZIKV viremia, reaching $10^{6.70}$ and $10^{7.00}$ RNA copies/ml post-challenge (FIG. 25A), which were equivalent to $10^{4.01}$ and $10^{4.33}$ PFU/ml of ZIKV, respectively (FIG. 25C). The viremia in both control groups declined by day 7 (FIGS. 25B and 25D). This result was consistent with previous observations that ZIKV only causes transient viremia in BALB/c mice. As the positive control, mice vaccinated with rVSV-G1670A-prM-E were completely protected from viremia at days 3 and 7, which was consistent with our previous study. The mice vaccinated with DNA vaccines or mtd-VSV-NS1 based vaccines had a significantly lower viremia at day 3 compared to the pCI and rVSV-D1762A controls (FIGS. 25A and 25C). However, a certain level of viremia (3 log PFU/ml), approximately 1 log higher than the detection limit, was detected in the DNA vaccine or mtd-VSV-NS1 based vaccine groups (FIG. 25C). By day 7, viremia in the mtd-VSV-NS1 vaccine groups has been cleared whereas 2.5-3 log PFU were still detected in the DNA vaccine groups (FIG. 25D). Collectively, these results indicate that a single dose of mtd-VSV-NS1 vaccine or two doses of DNA vaccine expressing NS1 provided partial protection in BALB/c mice against ZIKV-induced viremia. The protective efficacy of mtd-VSV-based NS1 vaccine was higher than that of the DNA vaccines.

Figures 26C, 26D, 26E, 26F:
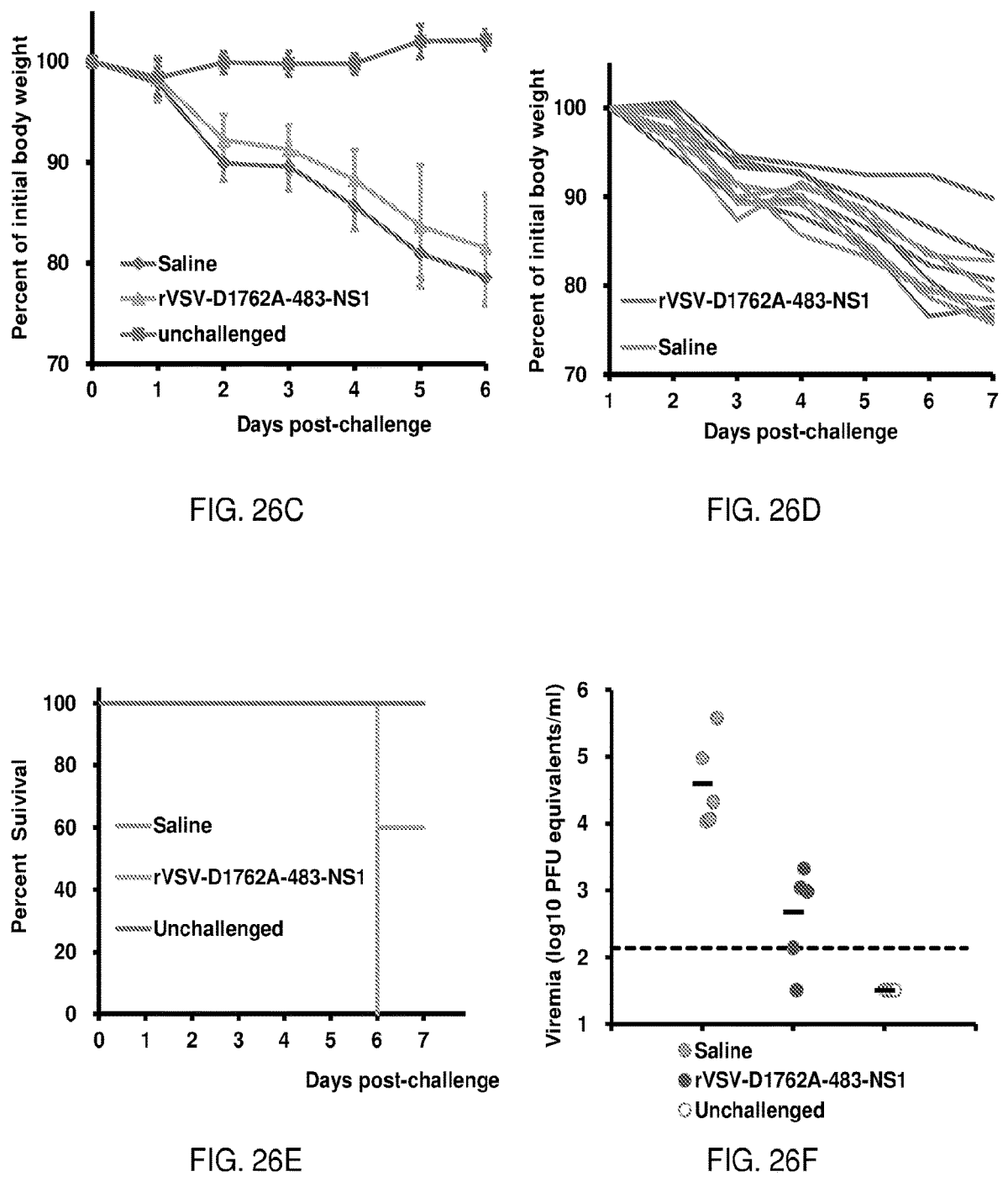

Similar results were found when tested in A129 mice. rVSV-D1762A-483-NS1 was chosen for use in the A126 experiments because it had induced higher NS1 antibody than rVSV-D1762A-tPA-NS1 in BALB/c mice. A129 mice were intramuscularly immunized with $10^3$ PFU of rVSV-D1762A-483-NS1. Two weeks later, A129 mice were boosted with $10^5$ PFU of the same virus. At week 2 post-booster vaccination, mice were challenged with $10^5$ PFU of ZIKV Cambodian strain. Body weight was monitored throughout the experiment. Mice inoculated with rVSV-D1762A-483-NS1 had no loss of body weight (FIG. 26A) or any abnormal reaction during the 4-week immunization time period, indicating that mtdVSV-based NS1 vaccine was completely attenuated in A129 mice. Two mice immunized with rVSV-D1762A-483-NS1 developed NS1-specific antibody at week 1 post-immunization and all the mice in this group developed high levels of NS1 antibody at week 2 post-immunization despite the fact that a relatively low dose ($10^3$ PFU) was used for vaccination (FIG. 26B). After booster vaccination, NS1 antibody did not significantly increase at weeks 3 and 4 (FIG. 26B). At week 4 post-immunization, mice from the unvaccinated group (saline) and rVSV-D1762A-483-NS1 group were challenged by ZIKV at a dose of $10^5$ PFU per mouse. This dose was chosen because prM-E or prM-E-NS1 based vaccine candidates provided complete protection in A129 mice. After ZIKV challenge, both rVSV-D1762A-483-NS1 and saline groups developed ZIKV-associated clinical signs and had significant body weight loss (FIG. 26C). However, two mice immunized with rVSV-D1762A-483-NS1 showed less body weight loss (FIG. 26D) and three mice in this group survived at day 7 post-challenge (FIG. 26E). In contrast, all the mice in the saline group were dead at day 6 post-challenge. ZIKV-induced viremia in these mice was measured at day 3 post-challenge. Results indicated that the mice immunized by rVSV-D1762A-483-NS1 had a significantly lower ZIKV viral load in blood compared with the saline group (FIG. 4F). Collectively, these data indicate that mtdVSV-NS1 vaccine provided partial protection against lethal ZIKV challenge.

Example 13—Materials and Methods

Cell Line, Viruses, and Plasmid construction. BHK-21 cells (ATCC no. CCL-10), Vero (ATCC no. CCL-81), and 293T cells (ATCC no. CRL-3216) were purchased from American Type Culture Collection (ATCC, Manassas, Va.). BSRT7 cells, which stably express T7 RNA polymerase, are clones of BHK-21 cells. All cell lines were grown in Dulbecco's modified Eagle's medium (DMEM; Life Technologies) supplemented with 10% FBS. ZIKV Cambodian strain (FSS13025) was obtained and propagated in Vero cells, and titrated using a standard plaque assay.

Plasmids encoding VSV N (pN), P (pP), and L (pL) genes, and an infectious cDNA clone of the viral genome, pVSV1 (+), were obtained. Plasmid pVSV1(+) GxxL, which contains SmaI and XhoI at the G and L gene junction, was obtained. The full-length envelope (E) gene (from amino acids 1 to 504) and E truncation mutants (E404 (amino acids 1-404); E414 (amino acid 1-414), and E415 (amino acid 1-415)) lacking the predicted stem-transmembrane domain (TM) were amplified from an infectious cDNA clone of ZIKV Cambodian strain (GenBank accession no. MH158236) b by high fidelity PCR. These DNA fragments were digested with SmaI and XhoI and cloned into pVSV (+)GxxL at the same sites. The resulting plasmids were designated pVSV(+)-E, pVSV(+)-E404, pVSV(+)-E414, and pVSV(+)-E415.

Using the same strategy, the anchor C (signal peptide) with E, E404, E414, and E415 were cloned into pVSV(+) GxxL at SmaI and XhoI sites resulted in construction of pVSV(+)-aE, pVSV(+)-aE404, pVSV(+)-aE414, and pVSV (+)-aE415 respectively. In addition, the anchor C-premembrane-envelope (prM-E), and anchor C-prM-E truncation mutants (prM-E404, prM-E414, and prM-E415), and anchor C-premembrane-envelope-nonstructural protein 1 (prM-E-NS1) genes were cloned into pVSV(+)GxxL at SmaI and XhoI sites. The resulting plasmids were designated pVSV (+)-prM-E, pVSV(+)-prM-E404, pVSV(+)-prM-E414, pVSV(+)-prM-E, 415, and pVSV(+)-prM-E-NS1.

Similarly, the anchor C-NS1 gene (amino acids 1-352) was cloned into pVSV(+)GxxL at the SmaI and XhoI sites, and the resultant plasmid was named pVSV(+)-NS1. To further attenuate the VSV vector, a point mutation, G1670A, in the large (L) polymerase protein was introduced, which rendered a recombinant virus that is specifically defective in mRNA cap G-N-7, but not 2'-O methylation. Using site-directed mutagenesis, G1670A mutation was introduced into pVSV(+)-E, pVSV(+)-aE, pVSV(+)-prM-E, pVSV(+)-prM-E-NS1, and pVSV(+)-NS1 which resulted in the construction of pVSV(+)-G1670A-E, pVSV(+)-G1670A-aE, pVSV (+)-G1670A-prM-E, pVSV(+)-G1670A-prM-E-NS1, and pVSV(+)-G1670A-NS1 respectively.

To prepare DNA vaccine plasmids, the anchor C-prM-E and anchor C-NS1 genes were cloned into pCI vector (Promega) which resulted in the construction of pCI-prM-E and pCI-NS1 respectively. All of the constructs were confirmed by sequencing.

Recovery of recombinant VSV expressing ZIKV antigens. Recovery of recombinant VSV (rVSV) from the infectious clone was carried out. rVSV was recovered by cotransfection of plasmid encoding VSV genome, and support plasmids encoding VSV nucleocapsid complex (pN, pP, and pL) into BSRT7 cells infected with a recombinant vaccinia virus (vTF7-3) expressing T7 RNA polymerase. At 96 h post-transfection, cell culture fluids were collected and filtered through a 0.2-μm filter, and the recombinant virus was further amplified in BSRT7 cells. Subsequently, the viruses were plaque purified as described previously. Individual plaques were isolated, and seed stocks were amplified in BSRT7 cells. The viral titer was determined by a plaque assay performed in Vero cells.

RT-PCR. Viral RNA was extracted from recombinant VSVs by using an RNeasy minikit (Qiagen, Valencia, Calif.) according to the manufacturer's instructions. ZIKV genes were amplified by a One Step RT-PCR kit (Qiagen) using primers annealing to VSV G gene at position 4524 (5'-CGAGTTGGTATTTATCTTTGC-3'; SEQ ID NO: 20) and L gene at position 4831 (5'-GTACGTCATGCGCTCATCG-3'; SEQ ID NO: 21) (numbering refers to the complete VSV Indiana genome sequence). The amplified products were analyzed on 1% agarose gel electrophoresis and sequenced.

Single-cycle growth curves. Confluent BSRT7 cells were infected with individual viruses at a multiplicity of infection (MOI) of 3. After 1 h of absorption, the inoculum was removed, the cells were washed twice with Dulbecco's modified Eagle's medium (DMEM), fresh DMEM (supplemented with 2% fetal bovine serum) was added, and the infected cells were incubated at 37° C. Aliquots of the cell culture fluid were removed at the indicated intervals, and virus titers were determined by plaque assay in Vero cells.

Analysis of the expression of ZIKV antigens by VSV. Confluent BSRT7 cells were infected with rVSV expressing ZIKV protein subunits, parental rVSV, or rVSV-G1670A at an MOI of 3.0. Three hours post-infection, cells were washed with methionine- and cysteine-free (M⁻ C⁻) medium and incubated with fresh M⁻ C⁻ medium supplemented with actinomycin D (15 μg/ml). After 1 h of incubation, the medium was replaced with M⁻ C⁻ medium supplemented with EasyTag $^{35}$S-Express (4 µCi/ml; Perkin-Elmer, Wellesley, Mass.). After 4 h of incubation, cytoplasmic extracts were prepared and analyzed by sodium dodecyl sulfate-polyacrylamide gel electrophoresis (SDS-PAGE). Labeled proteins were detected using a phosphorimager.

Detection of ZIKV antigen by Western blot. BSRT7 cells were infected with each rVSV expressing ZIKV antigen as described above. For DNA vaccine plasmid, HEK293T cells were transfected with pCI, pCI-prM-E, or pCI-NS1 using lipofectimine 2000. At the indicated times post-infection, cell culture medium was harvested and clarified at 3,000 rpm for 15 min and further concentrated at 30,000 rpm for 1.5 h. In the meantime, cells were lysed in lysis buffer containing 5% β-mercaptoethanol, 0.01% NP-40, and 2% SDS. Proteins were separated by 12% SDS-PAGE and transferred to a Hybond enhanced chemiluminescence nitrocellulose membrane (Amersham) in a Mini Trans-Blot electrophoretic transfer cell (Bio-Rad). The blot was probed with rabbit anti-ZIKV E or NS1 antibody (Alpha diagnostic Intl Inc., San Antonio, Tex.) at a dilution of 1:2,000, followed by horseradish peroxidase-conjugated goat anti-rabbit IgG secondary antibody (Santa Cruz) at a dilution of 1:5,000. The blot was developed with SuperSignal West Pico chemiluminescent substrate (Thermo Scientific) and exposed to Kodak BioMax MR film.

Production and purification of ZIKV VLPs by a VSV vector. Recombinant rVSV-E, rVSV-prM-E, or rVSV-prM-E-NS1 was inoculated into 10 confluent T150 flasks of BSRT7 cells at an MOI of 0.01 in a volume of 2 ml of DMEM. At 1 h post absorption, 15 ml of DMEM (supplemented with 2% fetal bovine serum) was added to the cultures, and infected cells were incubated at 37° C. for 24 to 48 h. Cell culture fluids were harvested when extensive cytopathic effect (CPE) was observed. Cell culture fluids were clarified by centrifugation at 3,000 g for 30 min. Virus was concentrated through a 40% (wt/vol) sucrose cushion by centrifugation at 30,000 g for 2 h at 4° C. in a Ty 50.2 rotor (Beckman). The pellet was resuspended in NTE buffer (100 mM NaCl, 10 mM Tris, 1 mM EDTA [pH 7.4]) and further purified through a CsCl isopycnic gradient by centrifugation at 35,000 g for 18 h at 4° C. in an SW55 rotor (Beckman). The final pellet was resuspended in 0.3 ml of NTE buffer. Purified ZIKV VLPs were analyzed by SDS-PAGE, Western blotting, and electron microscopy. The protein concentrations of the VLPs were measured by using the Bradford reagent (Sigma Chemical Co., St. Louis, Mo.).

Purification of ZIKV. Ten confluent T150 flasks of Vero cells were infected with ZIKV Cambodian strain at an MOI of 0.01 in a volume of 2 ml of DMEM. After 1 h of absorption, 20 ml of DMEM (supplemented with 5% fetal bovine serum) was added, and infected cells were incubated at 37° C. for 72 h. When extensive cytopathic effect (CPE) was observed, cell culture fluids were harvested for ZIKV purification, which was the same procedure as VLP purification mentioned above.

Transmission electron microscopy. Negative-staining electron microscopy of purified VLPs was performed. Briefly, 20 μl of VLP suspension was fixed in copper grids (Electron Microscopy Sciences, Inc.) and negatively stained with 1% ammonium molybdate. Virus particles were visualized by using a FEI Tecnai G2 Spirit transmission electron microscope (TEM) at 80 kV. Images were captured on a MegaView III side-mounted charge-coupled-device camera (Soft Imaging System, Lakewood, Colo.), and figures were processed using Adobe Photoshop software (Adobe Systems, San Jose, Calif.).

Animal experiments. Each inoculation group was separately housed in rodent cages under biosafety level 2 (BSL-2) conditions.

Experiment 1: determine whether VSV constructs are immunogenic in BALB/c mice. Sixty 4 to 6-week-old specific-pathogen-free female BALB/c mice were randomly divided into 12 groups (5 mice per group). Mice in group 1 were inoculated with parental rVSV (with no insertion). Mice in groups 2 to 10 were inoculated with nine different rVSVs expressing ZIKV antigens (rVSV-E404, rVSV-E414, rVSV-E415, rVSV-E, rVSV-prM-E404, rVSV-prM-E414, rVSV-prM-E415, rVSV-prM-E, and rVSV-prM-E-NS1). Mice in group 11 were inoculated with DMEM and served as uninfected controls (the normal control). Mice in group 12 were immunized with DNA vaccine pCI-prM-E. For VSV, each mouse was inoculated intranasally at a dose of $1\times10^6$ PFU in a volume of 50 For DNA vaccine, mice were immunized intramuscularly with 50 μg of pCI-prM-E, and boosted with same dose two weeks later. After inoculation, the animals were evaluated twice every day for mortality and the presence of any symptoms of VSV infection. The severity of clinical signs associated with VSV infection was scored based on the following criteria: grade 3 (severe) was characterized by ruffled fur, hyperexcitability, tremors, circling, and paralysis; grade 2 (moderate) was characterized by ruffled fur with neurological symptoms such as circling; grade 1 (mild) was characterized by ruffled fur but no neurological symptoms; grade 0 was defined as no symptoms. The body weight of each mouse was monitored every three days. Blood samples were collected from each mouse weekly by bleeding facial vein, and serum was isolated for antibody detection. At week 5 post-inoculation, all mice were euthanized.

Experiment 2: determine antibody and T cell immune responses triggered by mtdVSV in BALB/c mice. Thirty 6-week-old SPF female BALB/c mice were randomly divided into six groups (5 mice per group). Mice in group 1 were inoculated with DMEM and served as unimmunized controls (normal control). Mice in groups 2-6 were immunized with rVSV, rVSV-G1670A, rVSV-G1670A-E, rVSV-G1670A-prM-E, and rVSV-G1670A-prM-E-NS1. All mice were immunized intranasally at a dose of $1\times10^6$ PFU per mouse. After immunization, the animals were evaluated daily for body weight, mortality, and the presence of any symptoms of VSV infection. Blood samples were collected from each mouse weekly by bleeding facial vein, and serum was isolated for antibody detection. At week 5 post-inoculation, all mice were euthanized, and whole blood and spleens were isolated from each mouse for a T cell assay.

Experiment 3: determine whether mtdVSV vaccine can protect BALB/c mice against viremia until day 24 after ZIKV challenge. Seventy 4-week-old SPF BALB/c mice were randomly divided into 7 groups (10 per group, 5 female and 5 male). Mice in groups 1-5 were immunized with DMEM, rVSV-G1670A, rVSV-G1670A-E, rVSV-G1670A-prM-E, or rVSV-G1670A-prM-E-NS1. Mice in group 6 were immunized with DNA vaccine. Mice in group 7 were served as normal control (immunized with DMEM and unchallenged). For VSV, mice were inoculated intranasally at a dose of $1\times10^6$ PFU per mouse. For DNA vaccine, mice were immunized intramuscularly with 50 μg of pCI-prM-E, and boosted with same dose two weeks later. After immunization, the presence of any VSV symptom induced by mtdVSV-based ZIKV vaccine candidates was evaluated twice per day. At week 5 post-immunization, mice in groups 1-6 were challenged intravenously with ZIKV Cambodian strain at a dose of $1\times10^6$ PFU per mouse. At 24 h prior to ZIKV challenge, mice were intraperitoneally administered 1.8 mg of anti-IFNAR1 (Leinco Technologies, Fenton, Mo.) blocking antibody. After challenge, the animals were evaluated twice daily for mortality and the presence of any symptoms of ZIKV infection. The body weight for each mouse was monitored daily. At day 24 post-challenge, all mice from each group were euthanized. The blood, brain, lungs, liver, and spleen from each mouse were collected for virus quantification and histologic evaluation.

Experiment 4: determine whether mtdVSV vaccine can protect BALB/c mice against viremia until day 7 post-challenge. Mice (6-week-old) in groups 1-5 were immunized with saline, rVSV-G1670A, rVSV-G1670A-aE, rVSV-G1670A-prM-E, or rVSV-G1670A-prM-E-NS1. The mice in group 6 served as a normal control (unimmunized unchallenged). The experimental procedure was identical to Experiment 3 except the mice were euthanized at day 7 after challenge with ZIKV Cambodian strain.

Experiment 5: determine whether mtdVSV vaccine and DNA vaccine can protect A129 mice against ZIKV challenge. Thirty five 6-week-old female A129 mice were randomly divided into 7 groups (5 per group). Mice in groups 1-3 were immunized intramuscularly with pCI, pCI-prM-E, or pCI-NS1 at a dose of 50 μg DNA per mouse. Two weeks later, mice in groups 1-3 were boosted intramuscularly with the same plasmid at the same dose. Mice in groups 4-6 were administered intramuscularly using a single dose ($1\times10^5$ PFU per mouse) of rVSV-G1670A-prM-E-NS1, rVSV-prM-E-NS1, or rVSV-G1670A-prM-E. Mice in group 7 were served as unvaccinated unchallenged control. After immunization, mice were evaluated every three days for body weight. The safety of mtdVSV-based ZIKV vaccine candidates was evaluated twice per day. Blood samples were collected at week 1 and 3 from each mouse for detection of antibody. At week 4 post-immunization, mice in groups 1-6 were intraperitoneally challenged with ZIKV Cambodian strain at a dose of $1\times10^5$ PFU per mouse. After challenge, the animals were evaluated twice every day for mortality and the presence of any symptoms of ZIKV infection. The severity of clinical disease was scored based the following criteria: 1=heathy; 2=mild; 3=moderate; and 4=severe, and early removal is required. The body weight for each mouse was monitored daily. Blood was collected at days 3 and 7 for the detection of viremia. At day 7 post-challenge, all mice from each group were euthanized, and brain, lungs, uterus/ovary, and spleen from each mouse were collected for virus quantification and histologic evaluation.

Experiment 6: determine whether NS1 alone can protect BALB/c mice against viremia. Twenty-five 4-week-old female BALB/c mice were randomly divided into 5 groups (5 per group). Mice in groups 1-5 were immunized with DMEM, pCI, pCI-NS1, rVSV-G1670A-NS1, or rVSV-G1670A-prM-E. For VSV, mice were inoculated intranasally at a dose of $1\times10^6$ PFU per mouse. For DNA vaccine, mice were immunized intramuscularly with 50 μg of plasmid, and boosted with same dose two weeks later. At week 4 post-immunization, mice in groups 2-6 were intravenously challenged with ZIKV Cambodian strain at a dose of $1\times10^6$ PFU per mouse. At 24 h prior to ZIKV challenge, mice were intraperitoneally administered 1.8 mg of anti-IFNAR1 (Leinco Technologies) blocking antibody. At days 3 and 7 post-challenge, blood was collected from each mouse for detection of viremia by real-time RT-PCR.

Experiment 7: validate the safety and immunogenicity of rVSV-G1670A-prM-E-NS1 in A129 mice. There were three groups in this study. Mice in group 1 were immunized intramuscularly with a single dose ($1\times10^5$ PFU per mouse) of rVSV-G1670A-prM-E-NS1. Mice in groups 2 and 3 were served as unimmunized challenged control and normal control (unimmunized unchallenged). Blood was collected from each mouse weekly for antibody detection. At week 4, mice in groups 1 and 2 were intraperitoneally challenged with ZIKV Cambodian strain at a dose of $1\times10^5$ PFU per mouse. After challenge, mice were monitored for body weight changes and viremia every 1 or 3 days for 21 days.

Detection of ZIKV E or NS1-specific antibody by ELISA. Ninety-six-well plates were first coated with 50 μl of highly purified ZIKV E or NS1 protein (MyBioSource, Inc., San Diego, Calif.) (4 μg/ml, in 50 mM Na2CO3 buffer, pH 9.6) per well at 4° C. overnight, and then blocked with Bovine Serum Albumin (BSA, 1% W/V in PBS, 100 μl/well) at 37° C. for 2 h. Subsequently, individual serum samples were tested for ZIKV-specific Ab on antigen-coated plates. Briefly, serum samples were 2-fold serially diluted and added to E or NS1 protein-coated wells. After incubation at room temperature for 2 h, the plates were washed five times with phosphate-buffered saline (PBS)-Tween (0.05%), followed by incubation with 50 μl of goat anti-mouse IgG horseradish peroxidase (HRP)-conjugated secondary Abs (Sigma) at a dilution of 1:2,000 for 1 h. Plates were washed, developed with 100 μl of 3,3',5,5'-tetramethylbenzidine (TMB), stopped by 100 μl of $H_2SO_4$ (2 mol/L), and the optical density (OD) at 450 nm was determined by BioTek microplate reader. Endpoint titers were determined as the reciprocal of the highest dilution that had an absorbance value 2.1 folds greater than the background level (DMEM control). Ab titers were calculated by the geometric mean titers (GMT).

Detection of ZIKV neutralizing Ab. ZIKV-specific neutralizing Ab was determined using a microneutralization (MN) assay. Serum samples were serially diluted twofold in 96-well micro-plates, and 100 μl of virus solution containing 50 PFU of ZIKV-Cambodian strain was added to 100 μl of each serum dilution and incubated at 37° C. for 1 h. The mixtures were then transferred to 24-well plates containing confluent Vero cell monolayers. After incubation for 60 h at 37° C., cells were fixed with 4% (vol/vol) phosphate-buffered paraformaldehyde for 1 h and washed three times with PBS. After permeation by 0.4% (vol/vol) Triton-X 100 at room temperature for 20 min and washed for three times, a ZIKV E monoclonal antibody (MyBioSource, Inc.) was added to each well at a dilution of 1:1,000 and incubated at 37° C. for 2 h, followed by washing with PBS three times. A horseradish peroxidase-conjugated goat anti-rabbit IgG secondary antibody (Santa Cruz) at a dilution of 1:2,000 was added to each well and incubated at 37° C. for 1 h, followed by washing with PBS for three times. The plates were then developed with 3-Amino-9-ethylcarbazole (AEC) substrate for 1 h at room temperature and stained plaques in each well were counted under light microscope. The half maximal inhibitory concentration ($IC_{50}$) of neutralizing antibody in mice serum was calculated based on the number of plaques in each well compared with the average value of DMEM group.

Analysis of ZIKV-specific T cell responses. To determine the nature of T cell responses that supported the development of ZIKV-specific Ab responses by rVSV expressing ZIKV antigens, we analyzed cytokine production by ZIKV E-specific spleen T cells. More specifically, spleen cells were aseptically removed from mice 35 days after immunization, and minced by pressing through a cell strainer. Red blood cells were removed by incubation in 0.84% ammonium chloride and, following a series of washes in RPMI 1640, cells were resuspended in RPMI 1640 supplemented with 2 mM 1-glutamine, 1 mM sodium pyruvate, 10 mM HEPES, 100 U/ml penicillin, 100 µg/ml streptomycin, and 10% fetal calf serum. The cell concentrations were adjusted to $3 \times 10^6$ cells/mL and 100 µl were added into each well of a 96-well microtiter plate and cultured either alone or in the presence of 20 µg/ml of ZIKV E protein for 5 days at 37° C. in a 5% CO2 atmosphere. Culture supernatants were collected from each well and frozen at −80° C. until analysis of secreted cytokines using the Bio-Plex Pro Mouse Cytokine Standard 23-Plex, Group I (Bio-Rad Laboratories Inc, Hercules, Calif.) per manufacturer's instructions. The frequencies of ZIKV-specific Th1 ($IFN-\alpha^+CD4^+CD3^+$ and $TNF-\beta^+CD4^+CD3^+$), Th2 cells ($IL-4^+CD4^+CD3^+$, $IL-5^+CD4^+CD3^+$), Th17 ($IL-17A^+CD4^+CD3^+$), and Tfh ($IL-21^+CD4^+CD3^+$) cells were determined by intracellular staining with the corresponding anti-cytokine Abs (dilution of 1:5,000) after additional incubation in the presence of PMA and ionomycin. Cytokine-specific antibodies including Alexa Fluor 700 anti-CD3 (Cat. No. 100216), Alexa Fluor 750 anti-CD4 (Cat. No. 100460), Alexa Fluor 488 anti-IFNγ (Cat. No. 505813), PerCP Cy5.5 anti-TNFα (Cat. No. 506322), PE anti-IL-5 (Cat. No. 504307), Alexa Fluor 647 anti-IL-21 (Cat. No. 516803), PECy7 anti-IL-10 (Cat. No. 505026), Brilliant Violet 650 anti-IL-17 (Cat. No. 506929), Brilliant Violet 605 anti-IL-4 (Cat. No. 504125) were purchased from Biolegend (San Diego, Calif.). The cells were then analyzed with the aid of an Attune flow cytometer and data were expressed as mean % positive cells±one SD and statistical differences are indicated and as $*p \leq 0.05$.

Measurement of viral burden. At indicated time points after ZIKV challenge, blood was collected and organs were recovered. Organs were weighed and homogenized using a bead-beater apparatus (MagNA Lyser, Roche). The total RNA was extracted from tissue samples and blood by using TRIzol Reagent (Life technologies, Carlsbad, Calif.). Reverse transcription (RT) was conducted using a primer (5'-CTCGTCTCTTCTTCTCCTTCCTAGCATTGA-3; SEQ ID NO: 22) targeting the E gene of ZIKV and the Superscript III transcriptase kit (Invitrogen, Carlsbad, Calif.). The RT products were then used to perform real-time PCR using primers specifically targeting the E gene of ZIKV (forward, 5'-CATCAGGATGGTCTTGGCGATTCTAGC-3' (SEQ ID NO: 23) reverse, 5'-CTCGTCTCTTCTTCTCCTTCCTAG-CATTGA-3' (SEQ ID NO: 24)) in a StepOne real-time PCR system (Applied Biosystems). A standard curve was generated using a ZIKV plasmid encoding E gene or a serial dilution of ZIKV RNA from known quantities of infectious virus. Amplification cycles used were 2 min at 50° C., 10 min at 95° C., and 40 cycles of 15 s at 95° C. and 1 min at 60° C. The threshold for detection of fluorescence above the background was set within the exponential phase of the amplification curves. For each assay, 10-fold dilutions of standard plasmid or viral RNA were generated, and negative-control samples and double-distilled water ($ddH_2O$) were included in each assay. Viral burden is expressed on a log 10 scale as viral RNA equivalents per gram or per milliliter.

Histology. Half of the tissues (brain, lung, uterus/ovary, and spleen) from each experiment were preserved in 4% (vol/vol) phosphate-buffered paraformaldehyde. Fixed tissues were embedded in paraffin, sectioned at 5 and stained with hematoxylin-eosin (HE) for the examination of histological changes by light microscopy.

Quantitative and statistical analyses. Quantitative analysis was performed either by densitometric scanning of autoradiographs or by using a phosphorimager (Typhoon; GE Healthcare) and ImageQuant TL software (GE Healthcare, Piscataway, N.J.). Statistical analysis was performed by one-way multiple comparisons using SPSS 8.0 statistical analysis software (SPSS Inc., Chicago, Ill.). A P value of ≤0.05 was considered statistically significant.

Statement 1. A recombinant vector comprising a polynucleotide sequence encoding a Zika virus nonstructural protein 1 (NS1 protein).

Statement 2. The recombinant vector of statement 1, wherein the Zika virus NS1 protein has at least 90% amino acid sequence identity with SEQ ID NO: 14.

Statement 3. The recombinant vector of statement 1, wherein the Zika virus NS1 protein comprises an amino acid sequence according to SEQ ID NO: 14.

Statement 4. The recombinant vector of any one of statements 1-3, wherein the recombinant vector further comprises one or more polynucleotide sequences encoding a Zika virus envelope (E) protein or truncation mutant thereof, and a Zika virus premembrane (prM) protein.

Statement 5. The recombinant vector of statement 4, wherein: a) the Zika virus E protein has at least 90% amino acid sequence identity with SEQ ID NO: 4; b) the Zika virus E protein truncation mutant has at least 90% amino acid sequence identity with one of SEQ ID NO 10 (E404), SEQ ID NO: 8 (E414), or SEQ ID NO: 6 (E415); and c) the Zika virus prM protein has at least 90% amino acid sequence identity with SEQ ID NO: 12.

Statement 6. The recombinant vector of any one of statements 1-5, wherein the recombinant vector encodes the Zika virus NS1 protein, the Zika virus E protein or truncation mutant thereof, and the Zika virus prM protein.

Statement 7. The recombinant vector of any one of statements 1-6, wherein the recombinant vector comprises a DNA plasmid vector or an RNA viral vector.

Statement 8. The recombinant vector of statement 7, wherein the viral vector is selected from the group comprising adenovirus, adeno-associated virus (AAV), retrovirus, lentivirus, vaccinia virus, cytomegalovirus, Sendai virus, modified vaccinia Ankara virus, and vesicular stomatitis virus (VSV).

Statement 9. The recombinant vector of any one of statements 1-8, wherein the recombinant vector comprises a VSV vector.

Statement 10. The recombinant vector of statement 9, wherein the VSV vector comprises at least one mutation in a methyltransferase-encoding region of an L protein of the VSV vector.

Statement 11. The recombinant vector of statement 10, wherein the at least one mutation is a nucleic acid mutation that results in an amino acid mutation at a position in the VSV vector selected from the group of K1651, G1670, D1762, K1795, and E1833.

Statement 12. The recombinant vector of statement 10 or statement 11, wherein the at least one mutation is a nucleic acid mutation that results in a G1670A mutation or a D1762A mutation in the VSV vector.

Statement 13. The recombinant vector of statement 9, wherein the VSV vector comprises a nucleic acid sequence having at least 90% sequence identity to SEQ ID NO: 16.

Statement 14. The recombinant vector of statement 9, wherein the VSV vector comprises a nucleic acid sequence according to SEQ ID NO: 16, or SEQ ID NO: 16 encoding a G→A mutation at amino acid position 1670 of VSV L protein, or SEQ ID NO: 16 encoding a D→A mutation at amino acid position 1762 of VSV L protein.

Statement 15. An immunogenic composition comprising at least one recombinant vector according to any one of statements 1-14 and a pharmaceutically acceptable excipient.

Statement 16. The immunogenic composition of statement 15, further comprising an adjuvant.

Statement 17. A method for inducing an effective immune response against Zika virus in a subject, the method comprising administering to the subject an immunologically effective dose of the immunogenic composition of statement 15 or statement 16.

Statement 18. The method of statement 17, wherein the subject is human.

Statement 19. The method of statement 18, wherein the subject is pregnant, may be pregnant, or is trying to get pregnant.

Statement 20. The method of any one of statements 17-19, wherein the immunogenic composition is administered to the subject via a route selected from intranasal administration, subcutaneous administration, intramuscular administration, intradermal administration, and oral administration.

Statement 21. The method of any one of statements 17-20, further comprising administering at least one subsequent immunologically effective dose of the immunogenic composition.

Statement 22. A method for inducing an effective immune response against Zika virus in a subject, the method comprising expressing a Zika virus nonstructural protein 1 (NS1 protein) in cells of the subject.

Statement 23. The method of statement 22, wherein the Zika virus NS1 protein has at least 90% amino acid sequence identity with SEQ ID NO: 14.

Statement 24. The method of statement 22, wherein the Zika virus NS1 protein comprises an amino acid sequence according to SEQ ID NO: 14.

Statement 25. The method of any one of statements 22-24, further comprising co-expressing a Zika virus envelope (E) protein or a truncation mutant thereof, and a Zika virus premembrane (prM) protein.

Statement 26. The method of statement 25, wherein: a) the Zika virus E protein has at least 90% amino acid sequence identity with SEQ ID NO: 4; b) the Zika virus E protein truncation mutant has at least 90% sequence identity with one of SEQ ID NO 10 (E404), SEQ ID NO: 8 (E414), or SEQ ID NO: 6 (E415); and c) the Zika virus prM protein has at least 90% amino acid sequence identity with SEQ ID NO: 12.

Statement 27. The method of any one of statements 22-26, wherein the Zika virus protein(s) are expressed from a recombinant vesicular stomatitis virus (VSV) vector.

Statement 28. An expression cassette comprising a promoter operably linked to a polynucleotide encoding a Zika virus nonstructural protein 1 (NS1 protein).

Statement 29. The expression cassette of statement 28, wherein the polynucleotide encoding the Zika virus NS1 protein further encodes a Zika virus envelope (E) protein or a truncation mutant thereof, and a Zika virus premembrane (prM) protein.

Statement 30. The expression cassette of statement 29, wherein the Zika virus NS1 protein has at least 90% amino acid sequence identity with SEQ ID NO: 14, the Zika virus E protein has at least 90% amino acid sequence identity with SEQ ID NO: 4, the Zika virus E protein truncation mutant has at least 90% sequence identity with one of SEQ ID NO 10 (E404), SEQ ID NO: 8 (E414), or SEQ ID NO: 6 (E415), and the Zika virus prM protein has at least 90% amino acid sequence identity with SEQ ID NO: 12.

Statement 31. An immunogenic composition comprising at least one recombinant vector according to any one of statements 1-14 and a pharmaceutically acceptable excipient for use in inducing an effective immune response against Zika virus in a subject, the method comprising administering to the subject an immunologically effective dose of the immunogenic composition.

Statement 32. The immunogenic composition of statement 31, wherein the immunogenic composition further comprises an adjuvant.

Statement 33. The immunogenic composition of statement 31 or statement 32, wherein the subject is human, optionally wherein the human subject is pregnant, may be pregnant, or is trying to get pregnant.

Statement 34. The immunogenic composition of and one of statements 31-33, wherein the immunogenic composition is administered to the subject via a route selected from intranasal administration, subcutaneous administration, intramuscular administration, intradermal administration, and oral administration, and optionally wherein at least one subsequent immunologically effective dose of the immunogenic composition is administered to the subject.

Statement 35. An immunogenic composition comprising at least one recombinant vector according to any one of statements 1-14 and a pharmaceutically acceptable excipient for use in manufacturing a medicament.

The invention claimed is:

1. A recombinant vector comprising a polynucleotide sequence encoding a signal peptide fused to the N-terminus of a Zika virus nonstructural protein 1 (NS1 protein), wherein the signal peptide is selected from the group consisting of: tissue plasminogen activator (tPA), residues 456 to 504 of SEQ ID NO: 4, residues 484 to 504 of SEQ ID NO: 4, and residues 483 to 504 of SEQ ID NO: 4.

2. The recombinant vector of claim 1, wherein the Zika virus NS1 protein comprises:
(a) an amino acid sequence according to SEQ ID NO: 14; or
(b) an amino acid sequence, wherein the amino acid sequence has at least 90% amino acid sequence identity with SEQ ID NO: 14.

3. The recombinant vector of claim 1, wherein the recombinant vector further comprises one or more polynucleotide sequences encoding a Zika virus envelope (E) protein or truncation mutant thereof, and a Zika virus premembrane (prM) protein, wherein the recombinant vector encodes the signal protein fused to the N-terminus of the Zika virus NS1 protein, the Zika virus E protein or truncation mutant thereof, and the Zika virus prM protein.

4. The recombinant vector of claim 3, wherein:
the Zika virus E protein has at least 90% amino acid sequence identity with SEQ ID NO: 4;
the Zika virus E protein truncation mutant has at least 90% amino acid sequence identity with one of SEQ ID NO: 10 (E404), SEQ ID NO: 8 (E414), or SEQ ID NO: 6 (E415); and
the Zika virus prM protein has at least 90% amino acid sequence identity with SEQ ID NO: 12.

5. The recombinant vector of claim 1, wherein the recombinant vector comprises a DNA plasmid vector or an RNA viral vector, wherein the viral vector is selected from the group consisting of: an adenovirus, an adeno-associated virus (AAV), a retrovirus, a lentivirus, a vaccinia virus, a cytomegalovirus, a Sendai virus, a modified vaccinia Ankara virus, and a vesicular stomatitis virus (VSV).

6. The recombinant vector of claim 1, wherein the recombinant vector comprises a VSV vector.

7. The recombinant vector of claim 6, wherein the VSV vector comprises at least one mutation in a methyltransferase-encoding region of an L protein of the VSV vector, wherein the at least one mutation is a nucleic acid mutation that results in an amino acid mutation in the L protein at a position selected from the group of K1651, G1670, D1762, K1795, and E1833.

8. The recombinant vector of claim 7, wherein the at least one mutation is a nucleic acid mutation that results in a G1670A mutation or a D1762A mutation in the L protein.

9. The recombinant vector of claim 6, wherein the VSV vector comprises:
a nucleic acid sequence according to SEQ ID NO: 16, SEQ ID NO: 16 encoding a G→A mutation at amino acid position 1670 of VSV L protein, SEQ ID NO: 16 encoding a D→A mutation at amino acid position 1762 of VSV L protein; or a nucleic acid sequence having at least 90% sequence identity to SEQ ID NO: 16.

10. An immunogenic composition comprising at least one recombinant vector according to claim 1 and a pharmaceutically acceptable excipient.

11. A method for inducing an effective immune response against the Zika virus in a subject, the method comprising administering to the subject an immunologically effective dose of the immunogenic composition of claim 10, wherein the immunogenic composition is administered to the subject via a route selected from intranasal administration, subcutaneous administration, intramuscular administration, intradermal administration, and oral administration.

12. The method of claim 11, wherein the subject is human.

13. The method of claim 12, wherein the subject is pregnant, may be pregnant, or is trying to get pregnant.

14. The method of claim 11, further comprising administering at least one subsequent immunologically effective dose of the immunogenic composition.

15. A method for inducing an effective immune response against a Zika virus in a subject, the method comprising expressing a signal peptide fused to the N-terminus of a Zika virus nonstructural protein 1 (NS1 protein) in cells of the subject, wherein the signal peptide is selected from the group consisting of: tissue plasminogen activator (tPA), residues 456 to 504 of SEQ ID NO: 4, residues 484 to 504 of SEQ ID NO: 4, and residues 483 to 504 of SEQ ID NO: 4, and wherein a recombinant vesicular stomatitis virus (VSV) vector expresses the signal protein fused to the N-terminus of the Zika virus protein.

16. The method of claim 15, wherein the Zika virus NS1 protein comprises:
(a) an amino acid sequence according to SEQ ID NO: 14; or
(b) an amino acid sequence having at least 90% amino acid sequence identity with SEQ ID NO: 14.

17. The method of claim 15, further comprising co-expressing a Zika virus envelope (E) protein or a truncation mutant thereof, and a Zika virus premembrane (prM) protein, wherein the Zika virus E protein has at least 90% amino acid sequence identity with SEQ ID NO: 4; the Zika virus E protein truncation mutant has at least 90% sequence identity with one of SEQ ID NO: 10 (E404), SEQ ID NO: 8 (E414), or SEQ ID NO: 6 (E415); and the Zika virus prM protein has at least 90% amino acid sequence identity with SEQ ID NO: 12.

18. An expression cassette comprising a promoter operably linked to a polynucleotide encoding a signal peptide fused to the N-terminus of a Zika virus nonstructural protein 1 (NS1 protein), wherein the signal peptide is selected from the group consisting of: tissue plasminogen activator (tPA), residues 456 to 504 of SEQ ID NO: 4, residues 484 to 504 of SEQ ID NO: 4, and residues 483 to 504 of SEQ ID NO: 4.

19. The expression cassette of claim 18, wherein the polynucleotide encoding the Zika virus NS1 protein further encodes a Zika virus envelope (E) protein or a truncation mutant thereof, and a Zika virus premembrane (prM) protein, wherein the Zika virus NS1 protein has at least 90% amino acid sequence identity with SEQ ID NO: 14, the Zika virus E protein has at least 90% amino acid sequence identity with SEQ ID NO: 4, the Zika virus E protein truncation mutant has at least 90% sequence identity with one of SEQ ID NO: 10 (E404), SEQ ID NO: 8 (E414), or SEQ ID NO: 6 (E415), and the Zika virus prM protein has at least 90% amino acid sequence identity with SEQ ID NO: 12.

* * * * *